United States Patent
Curiel et al.

(10) Patent No.: US 7,297,542 B2
(45) Date of Patent: Nov. 20, 2007

(54) ADENOVIRUS VECTOR CONTAINING A HETEROLOGOUS PEPTIDE EPITOPE IN THE HI LOOP OF THE FIBER KNOB

(75) Inventors: David T. Curiel, Birmingham, AL (US); Victor N. Krasnykh, Birmingham, AL (US); Igor Dmitriev, Homewood, AL (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

(21) Appl. No.: 09/245,603

(22) Filed: Feb. 5, 1999

(65) Prior Publication Data

US 2002/0081280 A1   Jun. 27, 2002

Related U.S. Application Data

(60) Provisional application No. 60/099,801, filed on Sep. 10, 1998, now abandoned, provisional application No. 60/073,947, filed on Feb. 6, 1998, now abandoned.

(51) Int. Cl.
| | |
|---|---|
| *C12N 15/86* | (2006.01) |
| *C12N 15/63* | (2006.01) |
| *C12P 19/34* | (2006.01) |
| *A61K 48/00* | (2006.01) |
| *A61K 35/00* | (2006.01) |
| *C07H 21/04* | (2006.01) |
| *C12N 9/00* | (2006.01) |
| *C07K 1/00* | (2006.01) |

(52) U.S. Cl. .................. 435/456; 435/320.1; 435/91.1; 435/91.4; 435/183; 424/93.1; 530/412; 536/23.4; 514/44

(58) Field of Classification Search .................. 514/44; 424/93.2, 93.21; 435/320.1, 325, 235, 455, 435/456, 91.4, 91.41; 530/350; 536/23.1
See application file for complete search history.

(56) References Cited

U.S. PATENT DOCUMENTS

| | | | |
|---|---|---|---|
| 5,770,442 A | 6/1998 | Wickham | ................ 435/320.1 |
| 5,846,782 A * | 12/1998 | Wickham et al. | ........... 435/697 |
| 5,885,808 A | 3/1999 | Spooner | ..................... 435/455 |
| 6,824,771 B1 * | 11/2004 | Curiel et al. | ................ 424/93.2 |

FOREIGN PATENT DOCUMENTS

| | | |
|---|---|---|
| WO | WO 96/26281 | 8/1996 |
| WO | WO 98/07865 | 2/1998 |

OTHER PUBLICATIONS

Verma et al. Gene Therapy—Promises, Problems, and Prospects. Nature, vol. 389, pp. 239-242, Sep. 18, 1997.*
Sandhu et al. Human Gene Therapy. Critical Reviews in Biotechnology, vol. 17, No. 4, pp. 307-326, 1997.*
Eck et al. Gene-Based Therapy, Chapter 5. Goodman & Gilman's The Pharmacological Basis of Therapeutics, 9th Edition, 1996.*
Wickham et al. Journal of Virology, 71: 8221-8229, 1997.*
Merriam Webster's Collegiate Dictionary, 10th edition, Merriam-Webster, Incorporated, homogeneous, p. 554, 2001.*
Bergelson et al (Isolation of a common receptor for Coxsackie B viruses and adenoviruses 2 and 5. Science, 275:1320-1323.*
Xia et al., "Crystal Structure of the ReceptorBinding Domain of Adenovirus Type 5 Fiber Protein at 1.7 A Resolution," *Current Biology Ltd.*, vol. 2, No. 12, 1994, pp. 1259-1270.

* cited by examiner

*Primary Examiner*—Daniel M Sullivan
*Assistant Examiner*—Kimberly A. Makar
(74) *Attorney, Agent, or Firm*—Frommer Lawrence & Haug LLP; Thomas J. Kowalski; Deborah L. Lu

(57) ABSTRACT

The present invention provides means to modify the tropism of recombinant adenoviral vectors using genetic methods to alter the adenoviral fiber cell-binding protein. The present invention generates an adenovirus with modified fiber gene such that novel tropism is achieved. This recombinant adenovirus has a fiber gene modified in the HI loop domain.

10 Claims, 39 Drawing Sheets

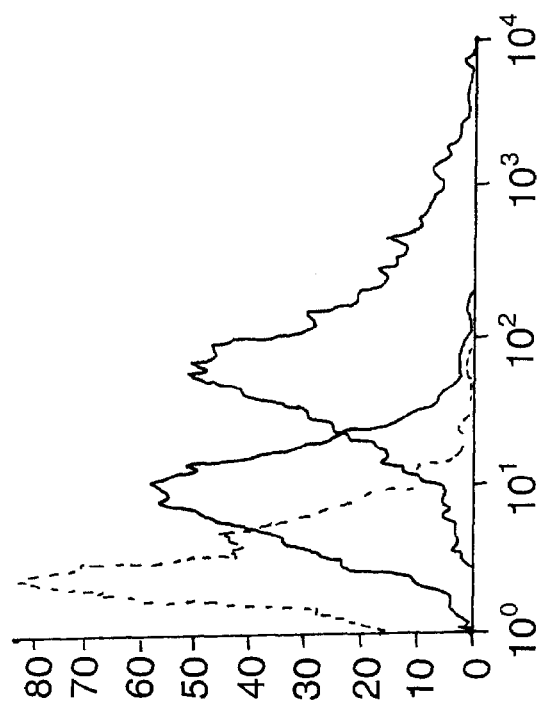
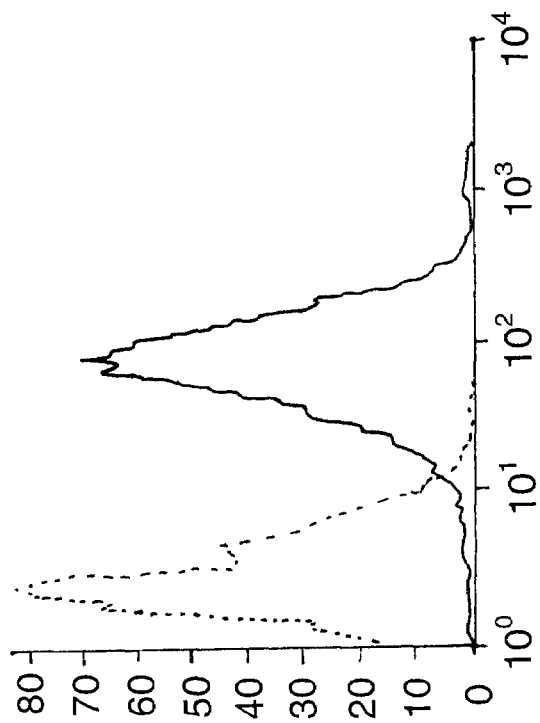
Fig. 11A
Fig. 11B

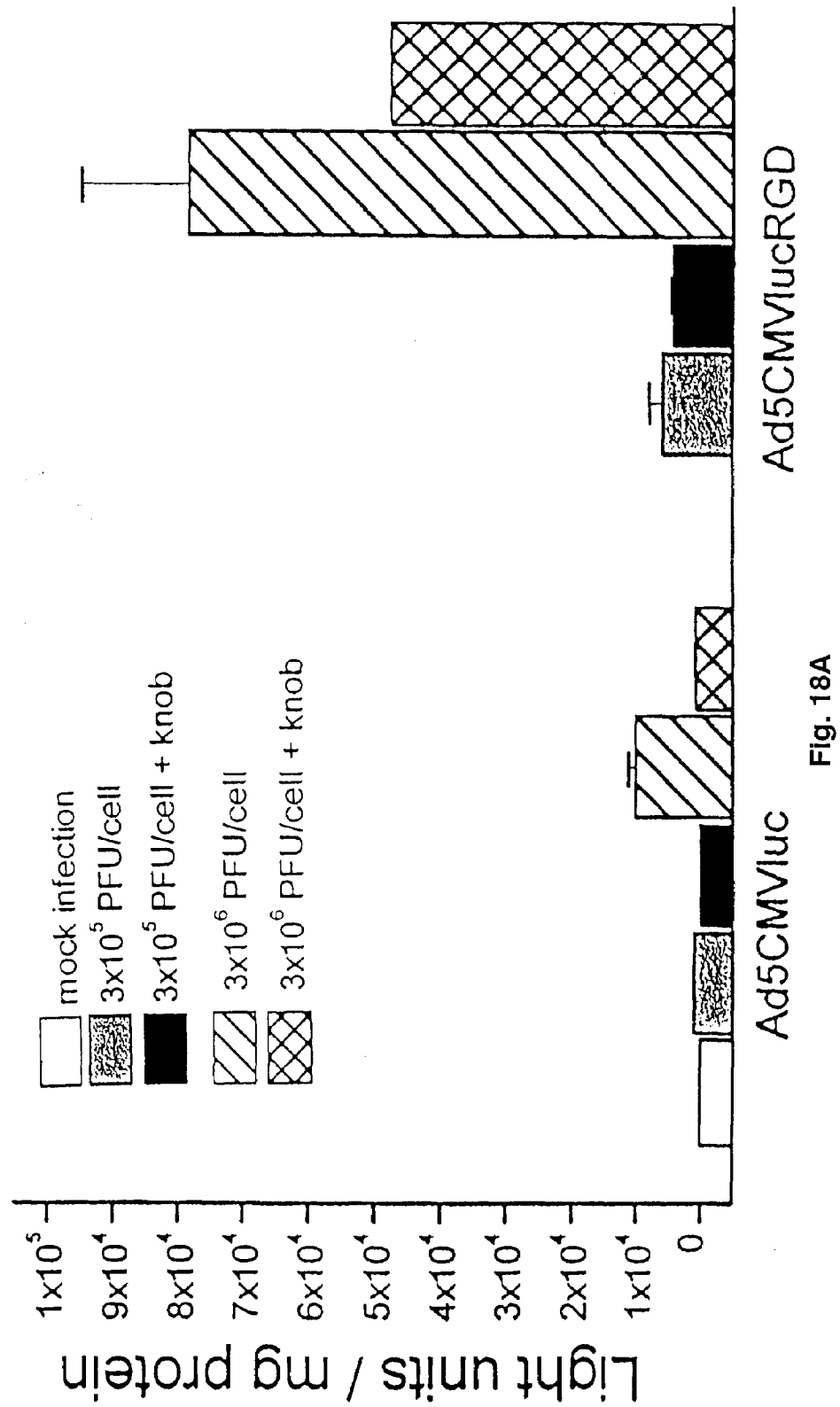

SEQUENCE LISTING

<160> NUMBER OF SEQ ID NOS: 17

<210> SEQ ID NO 1
<211> LENGTH: 38
<212> TYPE: DNA
<213> ORGANISM: artificial sequence
<220> FEATURE:
<221> NAME/KEY: primer_bind
<223> OTHER INFORMATION: Forward primer F1 used to generate a gene encoding the Ad5 fiber knob domain with the HI loop deleted.

```
<400> SEQUENCE: 1
taaggatccg gtgccattac agtaggaaac aaaaataa                              38

<210> SEQ ID NO 2
<211> LENGTH: 43
<212> TYPE: DNA
<213> ORGANISM: artificial sequence
<220> FEATURE:
<221> NAME/KEY: primer_bind
<223> OTHER INFORMATION: Reverse primer R1 used to generate a gene
      encoding the Ad5 fiber knob domain with the HI loop deleted.

<400> SEQUENCE: 2
catagagtat gcagatatcg ttagtgttac aggtttagtt ttg                        43

<210> SEQ ID NO 3
<211> LENGTH: 42
<212> TYPE: DNA
<213> ORGANISM: artificial sequence
<220> FEATURE:
<221> NAME/KEY: primer_bind
<223> OTHER INFORMATION: Forward primer F2 used to generate a gene
      encoding the Ad5 fiber knob domain with the HI loop deleted.

<400> SEQUENCE: 3
gtaacactaa cgatatctgc atactctatg tcattttcat gg                         42

<210> SEQ ID NO 4
<211> LENGTH: 41
<212> TYPE: DNA
<213> ORGANISM: artificial sequence
<220> FEATURE:
<221> NAME/KEY: primer_bind
<223> OTHER INFORMATION: Reverse primer R2 used to generate a gene
      encoding the Ad5 fiber knob domain with the HI loop deleted.

<400> SEQUENCE: 4
cccaagctta caattgaaaa ataaacacgt tgaaacataa c                          41

<210> SEQ ID NO 5
<211> LENGTH: 63
<212> TYPE: DNA
<213> ORGANISM: artificial sequence
<220> FEATURE:
<223> OTHER INFORMATION: Oligonucleotide annealed with SEQ ID NO: 6 to
      form a duplex and cloned into EcoRV-digested pQE.KNOBDHI.

<400> SEQUENCE: 5
tacactaaac ggtacccagg aaacaggaga cacaactgac tacaaggacg acgatgacaa      60
gcc                                                                   63

<210> SEQ ID NO 6
<211> LENGTH: 63
<212> TYPE: DNA
<213> ORGANISM: artificial sequence
<220> FEATURE:
<223> OTHER INFORMATION: Oligonucleotide annealed with SEQ ID NO: 5 to
      form a duplex and cloned into EcoRV-digested pQE.KNOBDHI.

<400> SEQUENCE: 6
ggcttgtcat cgtcgtcctt gtagtcagtt gtgtctcctg tttcctgggt accgtttagt      60
gta                                                                   63

<210> SEQ ID NO 7
<211> LENGTH: 29
```

```
<212> TYPE: DNA
<213> ORGANISM: artificial sequence
<220> FEATURE:
<223> OTHER INFORMATION: Oligonucleotide used in synthetic duplex which
      encodes MetHis6Lys.

<400> SEQUENCE: 7
gatccatgca tcaccatcac catcacaag                                    29

<210> SEQ ID NO 8
<211> LENGTH: 29
<212> TYPE: DNA
<213> ORGANISM: artificial sequence
<220> FEATURE:
<223> OTHER INFORMATION: Oligonucleotide used in synthetic duplex which
      encodes MetHis6Lys.

<400> SEQUENCE: 8
cgcgcttgtg atggtgatgg tgatgcatg                                    29

<210> SEQ ID NO 9
<211> LENGTH: 16
<212> TYPE: DNA
<213> ORGANISM: artificial sequence
<220> FEATURE:
<223> OTHER INFORMATION: An NdeI-SwaI linker ligated to plasmid pTG3602
      after partial digestion of the plasmid with NdeI.

<400> SEQUENCE: 9
tacccattta aatggg                                                  16

<210> SEQ ID NO 10
<211> LENGTH: 66
<212> TYPE: DNA
<213> ORGANISM: artificial sequence
<220> FEATURE:
<223> OTHER INFORMATION: Oligonucleotide in duplex cloned into EcoRV site
      of plasmid pQE.KNOBDHI generating pQE.KNOB.RGDHI.

<400> SEQUENCE: 10
cacactaaac ggtacacagg aaacaggaga cacaacttgt gactgccgcg gagactgttt    60
ctgccc                                                             66

<210> SEQ ID NO 11
<211> LENGTH: 66
<212> TYPE: DNA
<213> ORGANISM: artificial sequence
<220> FEATURE:
<221> NAME/KEY: primer_bind
<223> OTHER INFORMATION: Oligonucleotide in duplex cloned into EcoRV site
      of plasmid pQE.KNOBDHI generating pQE.KNOB.RGDHI.

<400> SEQUENCE: 11
gggcagaaac agtctccgcg gcagtcacaa gttgtgtctc ctgtttcctg tgtaccgttt    60
agtgtg                                                             66

<210> SEQ ID NO 12
<211> LENGTH: 41
<212> TYPE: DNA
<213> ORGANISM: artificial sequence
<220> FEATURE:
<223> OTHER INFORMATION: Oligonucleotide in synthetic duplex used to
      replace 41 bp PacI-ClaI-fragment in pcDNA.Luc,
      generating pcLucPC1.

<400> SEQUENCE: 12
```

```
caaatacaaa ggatatcagg tggcccccgc tgaattggag t                    41
```

<210> SEQ ID NO 13
<211> LENGTH: 45
<212> TYPE: DNA
<213> ORGANISM: artificial sequence
<220> FEATURE:
<223> OTHER INFORMATION: Oligonucleotide in synthetic duplex used to
      replace 41 bp PacI-ClaI-fragment in pcDNA.Luc,
      generating pcLucPC1.

<400> SEQUENCE: 13

```
cgactccaat tcagcgggggg ccacctgata tcctttgtat ttgat             45
```

<210> SEQ ID NO 14
<211> LENGTH: 13
<212> TYPE: PRT
<213> ORGANISM: artificial sequence
<220> FEATURE:
<223> OTHER INFORMATION: Amino acid sequence deleted from the HI loop of
      the fiber knob domain and replaced with a
      unique EcoRV site.

<400> SEQUENCE: 14

```
Thr Leu Asn Gly Thr Gln Glu Thr Gly Asp Thr Thr Pro
                 5                  10
```

<210> SEQ ID NO 15
<211> LENGTH: 8
<212> TYPE: PRT
<213> ORGANISM: artificial sequence
<220> FEATURE:
<223> OTHER INFORMATION: Amino acid sequence of the FLAG octapeptide.

<400> SEQUENCE: 15

```
Asp Tyr Lys Asp Asp Asp Asp Lys
                 5
```

<210> SEQ ID NO 16
<211> LENGTH: 9
<212> TYPE: PRT
<213> ORGANISM: artificial sequence
<220> FEATURE:
<223> OTHER INFORMATION: Amino acid sequence of a RGD peptide
      incorporated into the region of the fiber gene within the HI loop.

<400> SEQUENCE: 16

```
Cys Asp Cys Arg Gly Asp Cys Phe Cys
                 5
```

<210> SEQ ID NO 17
<211> LENGTH: 13
<212> TYPE: PRT
<213> ORGANISM: artificial sequence
<220> FEATURE:
<223> OTHER INFORMATION: Amino acid sequence of peptide replacing the
      RGD coding sequence.

<400> SEQUENCE: 17

```
Thr Leu Asn Gly Thr Gln Glu Thr Gly Asp Thr Thr Pro
                 5                  10
```

ADENOVIRUS VECTOR CONTAINING A HETEROLOGOUS PEPTIDE EPITOPE IN THE HI LOOP OF THE FIBER KNOB

CROSS-REFERENCE TO RELATED APPLICATIONS

This application claims benefit of U.S. provisional application Ser. No. 60/073,947 filed Feb. 6, 1998, now abandoned and U.S. provisional application Ser. No. 60/099,801 filed Sep. 10, 1998, now abandoned.

FEDERAL FUNDING LEGEND

This invention was created in part using funds from the National Institutes of Health under grants RO1-HL50255, RO1-CA68245, RO1-CA74242, R21-CA69343, T32-CA75930 and DAMD 17-94-J4398. The federal government, therefore, has certain rights in this invention.

BACKGROUND OF THE INVENTION

1. Field of the Invention

The present invention relates generally to the fields of virology and gene therapy. More specifically, the present invention relates to the production of recombinant adenoviral vectors with modified fibers for the purpose of cell-specific targeting with the additional advantages of the concomitant elimination of endogenous tropism.

2. Description of the Related Art

Recombinant adenovirus vectors are used in a number of gene therapy applications (21, 35, 38). This fact has derived principally from the high levels of gene transfer achievable with this vector approach both in vitro and in vivo. Recombinant adenovirus vectors are distinguished from other available systems by their unique ability to accomplish in situ gene delivery to differentiated target cells in a variety of organ contexts (5, 6, 9, 10, 12, 20, 25, 27, 29, 31).

One disadvantage to the use of recombinant adenoviruses for gene therapy is related to the virus' reliance on the presence of the coxsackievirus and adenovirus receptor (CAR) to achieve high levels of gene transfer. In certain settings, this may result in sequestration of recombinant virions by nontarget, yet high CAR-expressing cells, whereas the true target cells, if low in CAR, are poorly transduced. In order to compensate for this sequestration, significant escalation in the dose of administered vector is needed, increasing the risk of inducing both direct toxicity and immune responses against the vector and further compromising the overall efficacy of the therapy. Therefore, the utility of the present generation of adenovirus vectors for gene therapy may be significantly improved by achieving targeted transduction of specific cell types by the virus.

Despite this property, specific aspects of the adenovirus biology have prevented the full realization of the potential of such vectors. In this regard, the broad tropism profile of the parent virus for cells of diverse tissues potentially allows unrestricted gene delivery. Thus, for the many gene therapy applications requiring targeted, cell-specific gene delivery, the promiscuous tropism of the adenovirus vector represents a confounding factor. Based on this concept, strategies to modify the native tropism of adenovirus have been developed to allow the derivation of vectors capable of targeted gene delivery.

Strategies to achieve this end are directed at modifying specific steps in the adenoviral infection pathway. Adenoviruses of serotypes 2 and 5 normally achieve initial recognition and binding to target cells by means of interactions between the carboxy-terminal knob domain of the fiber protein and the primary receptor (4, 17, 36). After binding, RGD motifs in the penton base interact with cellular integrins of the $\alpha_v\beta_3$ and $\alpha_v\beta_5$ types (1-3, 37, 39, 40). This interaction triggers cellular internalization whereby the virions achieve localization within the endosome. Acidification of the endosome elicits conformational changes in capsid proteins, allowing their interaction with the endosome membrane in a manner that achieves vesicle disruption and particle escape.

Following endosomolysis, the virion translocates to the nucleus, where the subsequent steps of the viral life cycle occur. This understanding of the key role played by capsid proteins in the viral infectious pathway has suggested strategies to alter this process via modifications of these proteins.

In this regard, genetic retargeting of adenovirus vectors via modification of viral genes encoding coat proteins, if successful, offers a simple way to achieve a significant improvement in the present generation of these gene delivery vehicles. To this end, several groups have reported genetic modifications to the knob domain of adenovirus fiber protein and incorporation of such chimeric fibers into virion. For instance, Stevenson et al. and others reported successful generation of AdS virions containing fibers consisting of the tail and shaft domains of Ad5 fiber and the knob domain of Ad3, respectively. In addition, Michael et al. demonstrated the incorporation of the gastrin-releasing peptide into the carboxy terminus of recombinant Ad5 fiber. This finding was extended by Legrand et al. who achieved rescue of recombinant adenovirus vectors containing such fibers. Wickham et al. described the generation of recombinant virus containing fibers with carboxy-terminal polylysine sequences. These studies have established key feasibility issues with respect to this genetic approach but have also demonstrated a number of limiting factors.

All of these modifications of adenovirus fiber were directed towards the carboxy terminus of the protein. In addition, these efforts were initiated without prior knowledge of the three-dimensional (3D) structure of the fiber knob. Thus, the employment of the carboxy terminus of the fiber represented a choice not fully incorporating all relevant considerations. Clearly, 3D structural information has important bearing upon the placement of heterologous protein sequences within the knob for targeting purposes. Such localization of targeting ligands would ideally be achieved in a manner to allow their surface presentation and to minimally perturb the fiber quaternary structure.

To overcome the limitations imposed by the CAR-dependence of adenovirus infection, the incorporation of small peptide motifs possessing receptor binding specificities into the carboxy terminal of adenovirus fiber protein has been proposed, thus enabling the virus to attach and infect via a novel cell surface receptor. This concept has been developed by Wickham et al., who have proven the feasibility of this approach by generating several recombinant adenoviruses containing fibers with targeting ligands positioned at the carboxy terminal of the fiber molecule.

Although in some cases, genetic modification of the carboxy terminal of adenovirus fiber has proven its utility with respect to vector retargeting, it has failed in some others, suggesting that this locale in the fiber molecule is not an optimal site for incorporation of targeting protein moieties. Published findings strongly suggest that addition of more than 25-30 amino acid residues of heterologous protein sequence to the carboxy terminal of the fiber molecule has dramatic negative effect on the stability of the fiber trimer and, therefore, is incompatible with the fiber functions. In addition, the three-dimensional structure of the fiber knob indicates that the carboxy terminal of the fiber points towards the virion, that is, away from the cell surface, thereby providing suboptimal environment for the incorporation of targeting ligands.

The prior art is deficient in the lack of effective means of incorporating heterologous protein sequences into the fiber knob protein of adenovirus for purposes of retargeting. The present invention fulfills this longstanding need and desire in the art.

SUMMARY OF THE INVENTION

The utility of the present generation of recombinant adenovirus vectors for gene therapy applications could potentially be improved by designing targeted vectors capable of gene delivery to selected cell types in vivo. To achieve such targeting, one can incorporate ligands in the adenoviral fiber protein, which mediates primary binding of adenovirus to its cell surface receptor. Based on the proposed structure of the cell binding domain of the fiber, the HI loop of the fiber knob can be utilized as the locale for incorporation of heterologous ligands. As described herein, recombinant fiber proteins expressed in baculovirus-infected insect cells were utilized to demonstrate that the incorporation of the FLAG octapeptide into the HI loop does not ablate fiber trimerization and does not disturb formation of the cell-binding site localized in the knob. A recombinant adenovirus containing this modified fiber was then generated and the short peptide sequence engineered in the knob was compatible with the biological functions of the fiber. In addition, by using a ligand-specific antibody, the peptide incorporated into the knob remains available for binding in the context of mature virions containing modified fibers. These findings suggest that heterologous ligands can be incorporated into the HI loop of the fiber knob and that this locale possesses properties consistent with its employment in adenovirus retargeting strategies.

The utility of recombinant adenoviruses vectors (Ad) is limited due to the low efficiency of adenovirus-mediated gene transfer to cells expressing marginal levels of the adenovirus fiber receptor, CAR. In order to achieve CAR-independent gene transfer by adenovirus vector in clinically important contexts, modification of viral tropism via genetic alterations to the viral fiber protein is proposed herein. It is shown herein that incorporation of an Arg-Gly-Asp (RGD) containing peptide in the HI loop of the fiber knob domain results in the ability of the virus to utilize an alternative receptor during the cell entry process. It is also demonstrated herein that due to its expanded tissue tropism, this novel vector is capable of efficient transduction of primary tumor cells. Two to three orders of magnitude of increased gene transfer to ovarian cancer cells was demonstrated by the vector, suggesting that recombinant adenoviruses containing fibers with an incorporated RGD peptide may be of great utility for treatment of neoplasms characterized by deficiency of the primary Ad5 receptor.

In an embodiment of the present invention, there is provided a recombinant adenovirus, wherein the adenovirus comprises a fiber gene modified in the HI loop domain of the fiber knob.

In another embodiment, there is provided a method of killing tumor cells in an individual in need of such treatment, comprising the steps of: administering to the individual an effective amount of a recombinant adenovirus comprising a fiber gene modified in the HI loop domain of the fiber knob and a gene encoding the herpes simplex virus-thymidine kinase; and treating the individual with ganciclovir.

In yet another embodiment of the present invention, there is provided a method of providing gene therapy to an individual in need of such treatment, comprising the steps of: administering to the individual an effective amount of a recombinant adenovirus comprising a fiber gene modified in the HI loop domain of the fiber knob and a therapeutic gene.

In still yet another embodiment of the present invention, there is provided a method of increasing the ability of an adenovirus to transduce a cell, comprising the step of: modifying the fiber gene in the HI loop domain of the fiber knob of the adenovirus.

Other and further aspects, features, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 3 shows an analysis of recombinant fiber proteins by polyacrylamide gel electrophoresis. Fiber proteins expressed in insect cells were analyzed by gel electrophoresis to confirm their trimeric configurations. To dissociate trimers to monomers, the proteins were denatured by boiling them in the sample buffer prior to loading them on a 7.5% polyacrylamide gel. The bands were visualized by Coomassie blue staining.

Recombinant Ad5 fiber knob protein was added to cells prior to infection with the virus. Each data point is the average of three independent measurements obtained in one experiment.

Figure 17A:
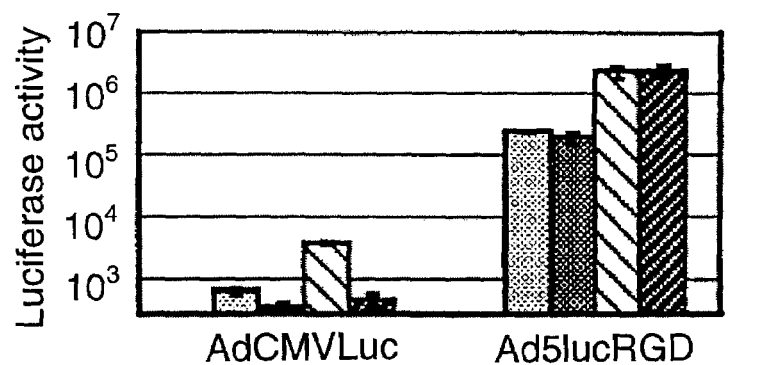
Figure 17B:
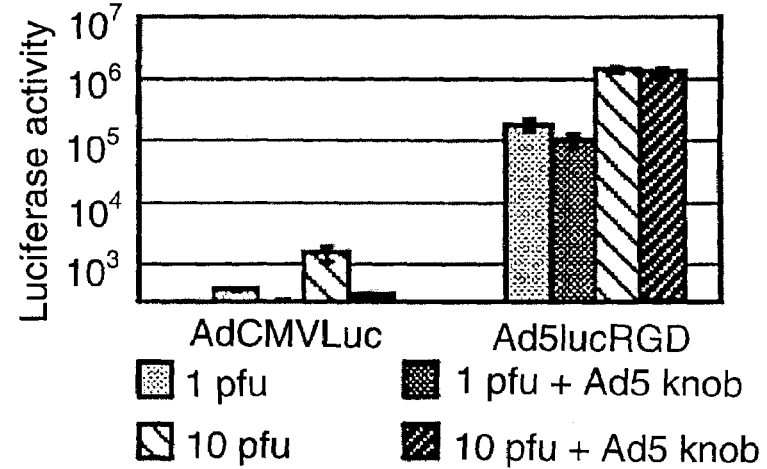

FIG. 17 shows the transduction of primary cells isolated from ascites obtained from ovarian cancer patients. Cells isolated from ascites of two (FIG. 17A and FIG. 17B) ovarian cancer patients were transduced with AdCMVLuc or Ad5lucRGD at an moi of 1 or 10 in the presence or absence of blocking Ad5 fiber knob protein. The data points represent the mean of three independent determinations.

Figure 18B:
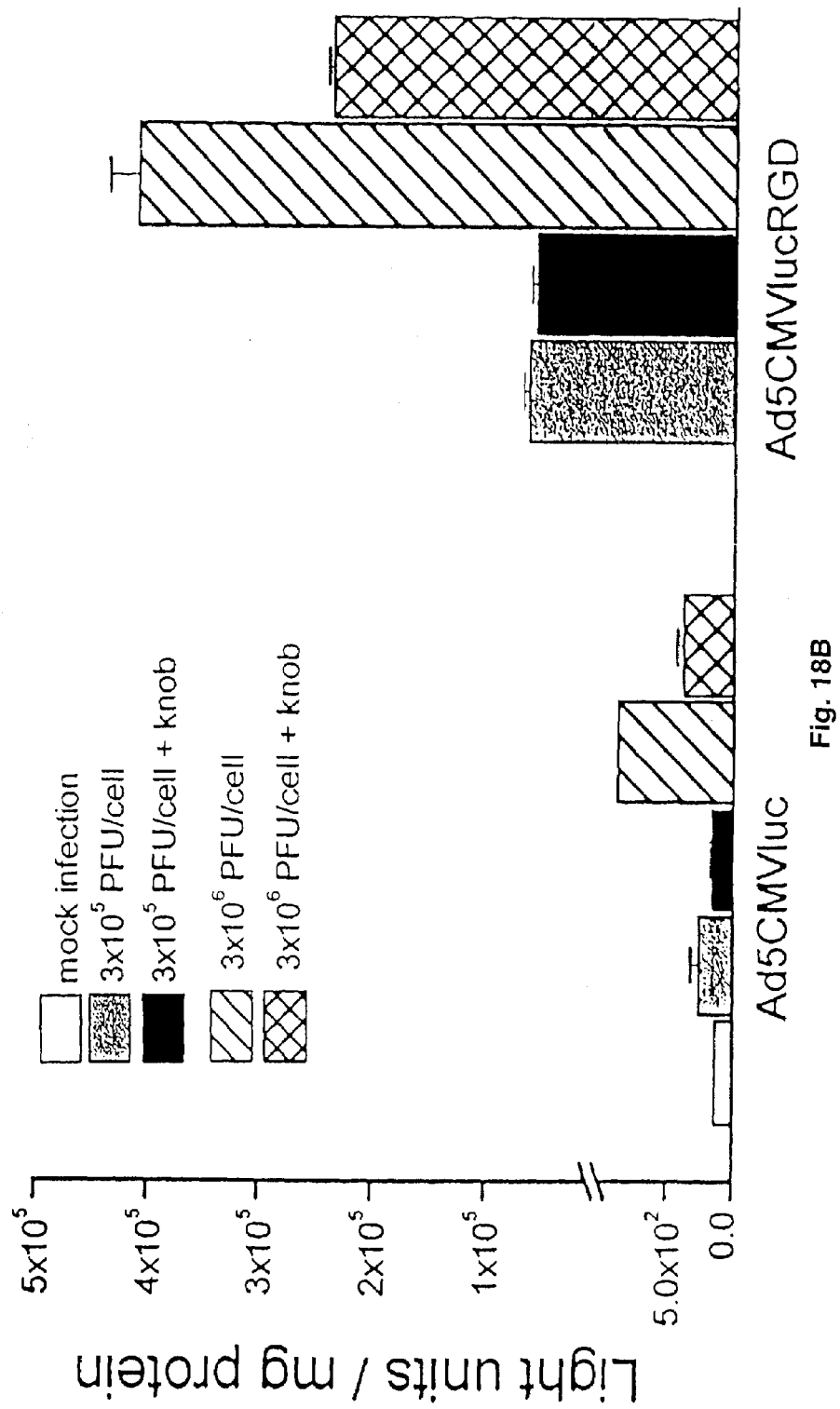
Figure 18C:
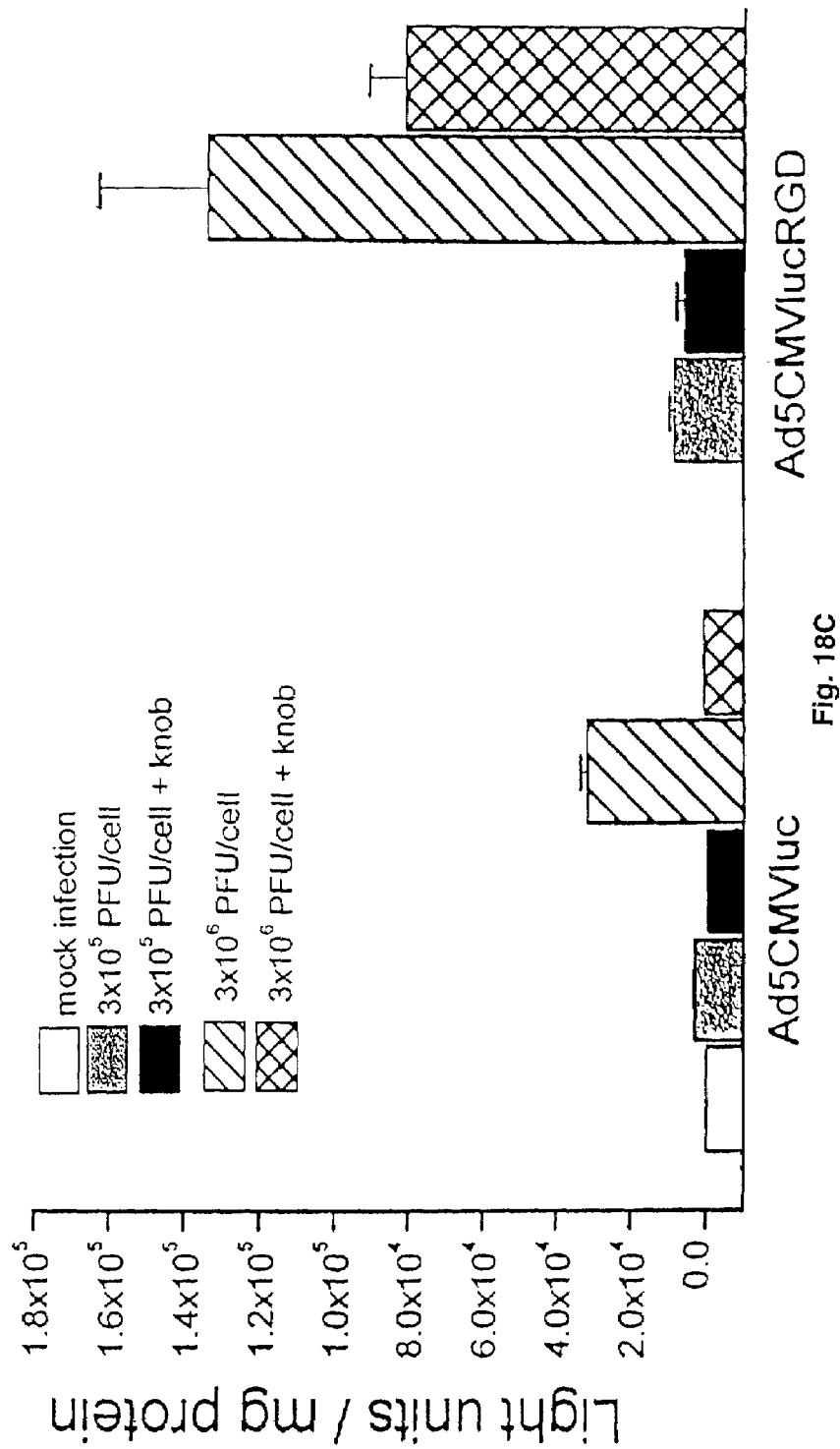

FIG. 18 shows adenoviral vector-mediated gene transfer to human ovarian cancer cell lines. SKOV3.ip1 (FIG. 18A), CaOV-3 (FIG. 18B), and UCI-101 (FIG. 18C) cells were infected with AdCMVLuc or Ad5lucRGD at 1 or 10 pfu/cell after preincubation in normal media (grey box) and (hatched box), or in media containing recombinant Ad5 fiber knob, (black box) and (cross-hatched box), respectively. After incubation at 37° C. for 30 h, the cells were lysed and the luciferase activity was determined. Data normalized for protein concentration are shown. Background luciferase activity in mock-infected cells is also displayed (open box). Each point represents the mean±standard deviation of three determinations.

Figure 19A:
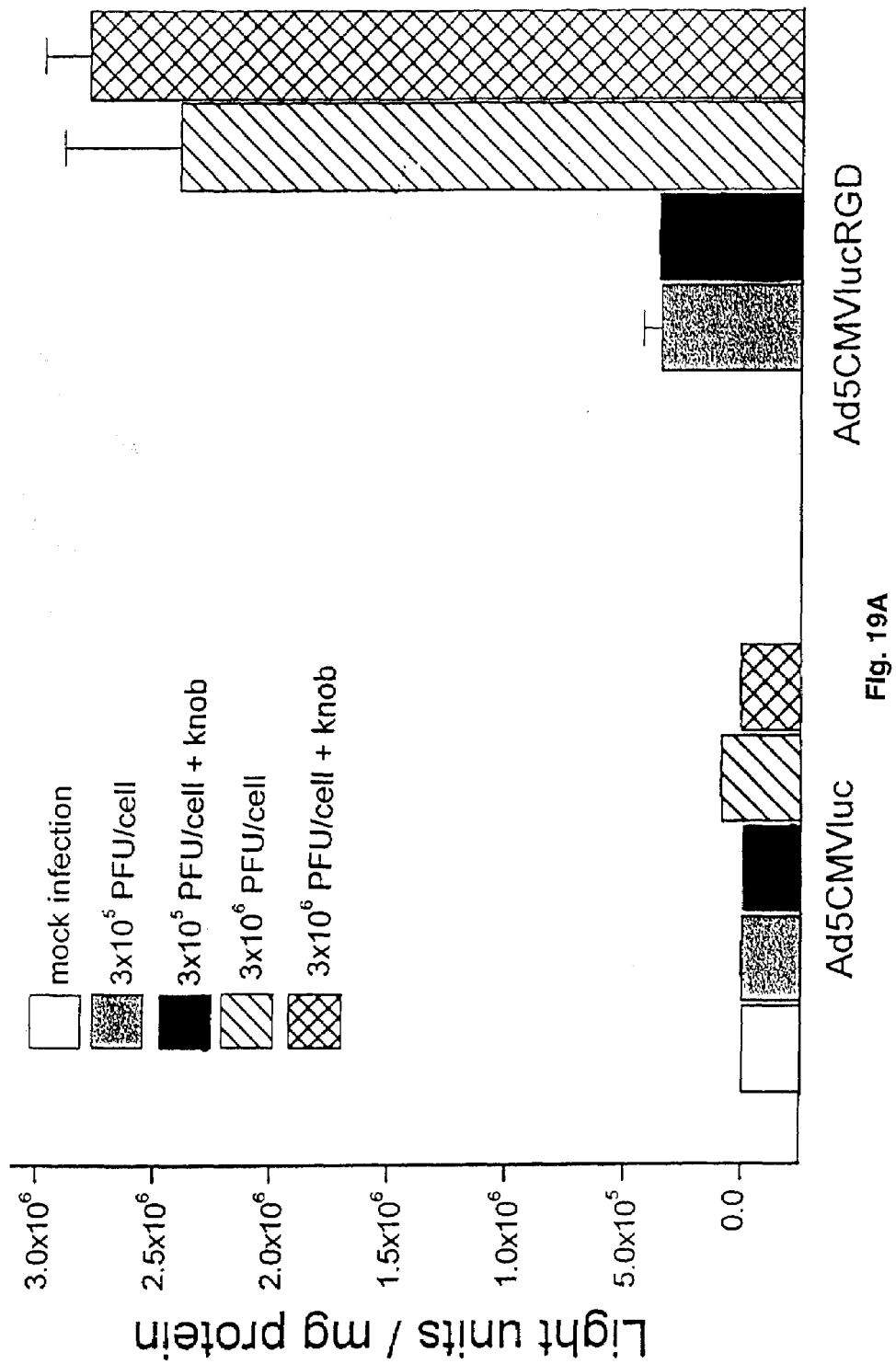
Figure 19B:
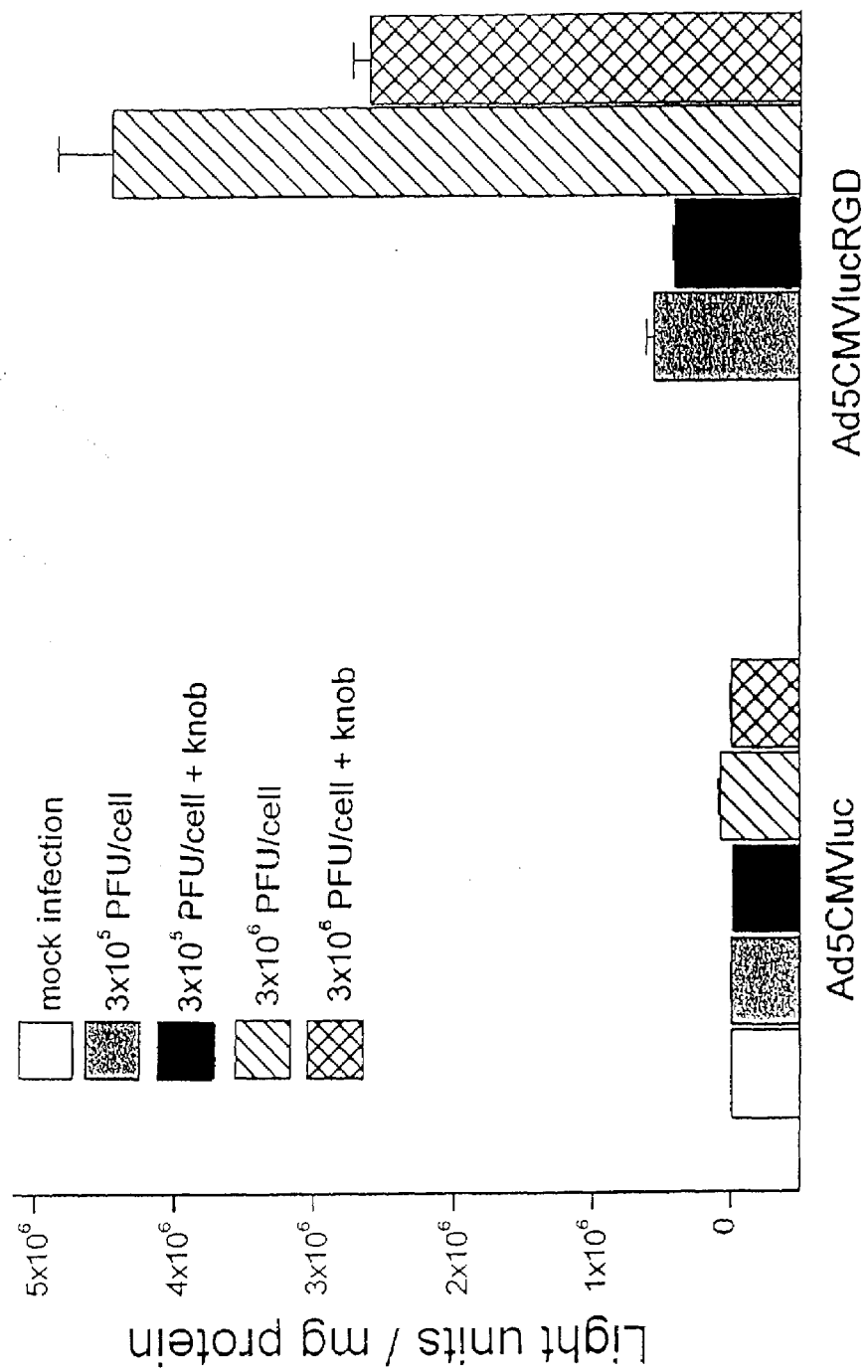

FIG. 19 shows adenoviral vector-mediated gene transfer to human ascites cells from ovarian cancer patients. Primary cells obtained from ascites were infected with AdCMVLuc or Ad5lucRGD at 1 or 10 pfu/cell after preincubation in normal media, (grey box) and (hatched box), or in media containing recombinant Ad5 fiber knob, (black box) and (cross-hatched box), respectively. After incubation at 37° C. for 30 hours, the cells were lysed and the luciferase activity was determined. Data normalized for protein concentration is shown. Background luciferase activity in mock-infected cells is also displayed (open box). Each point represents the mean±standard deviation of three determinations. Data from two representative samples, (FIG. 19A) and (FIG. 19B), are shown.

Figure 20:
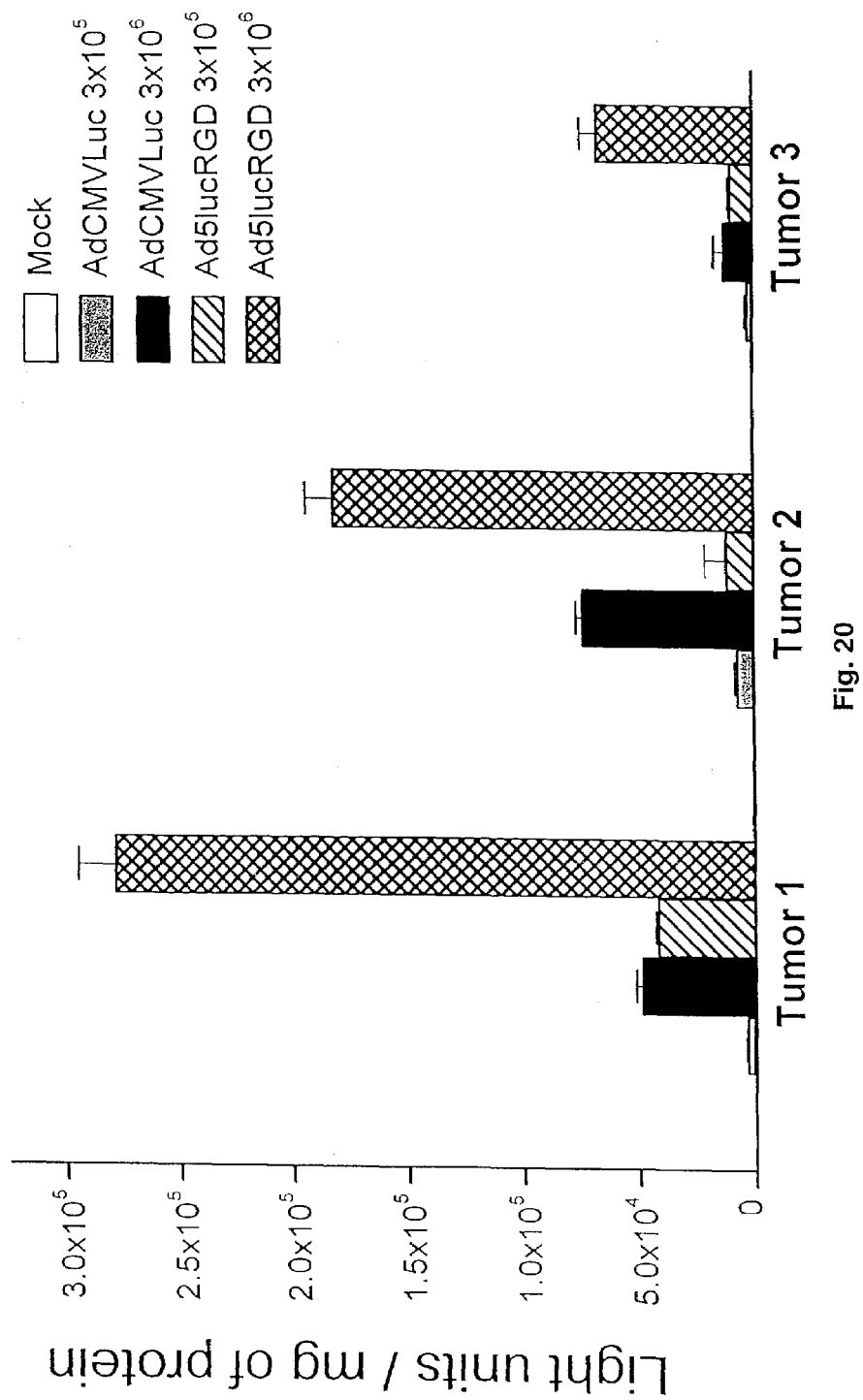

FIG. 20 shows adenoviral vector-mediated gene transfer to primary ovarian tumor explants. Tumoral explants directly obtained from ovarian cancer patients were infected at doses of $3 \times 10^5$ or $3 \times 10^6$ pfu with AdCMVLuc, (grey box) and (black box), or Ad5lucRGD, (hatched box) and (cross-hatched box), respectively. After incubation at 37° C. for 30 h, the tissues were lysed and the luciferase activity was determined. Data normalized for protein concentration is shown. Background luciferase activity in mock-infected tumor explants is also shown (open box). Each point represents the mean±standard deviation of determinations in three explants from the same patient. Data from three representative patients are shown.

Figure 21:
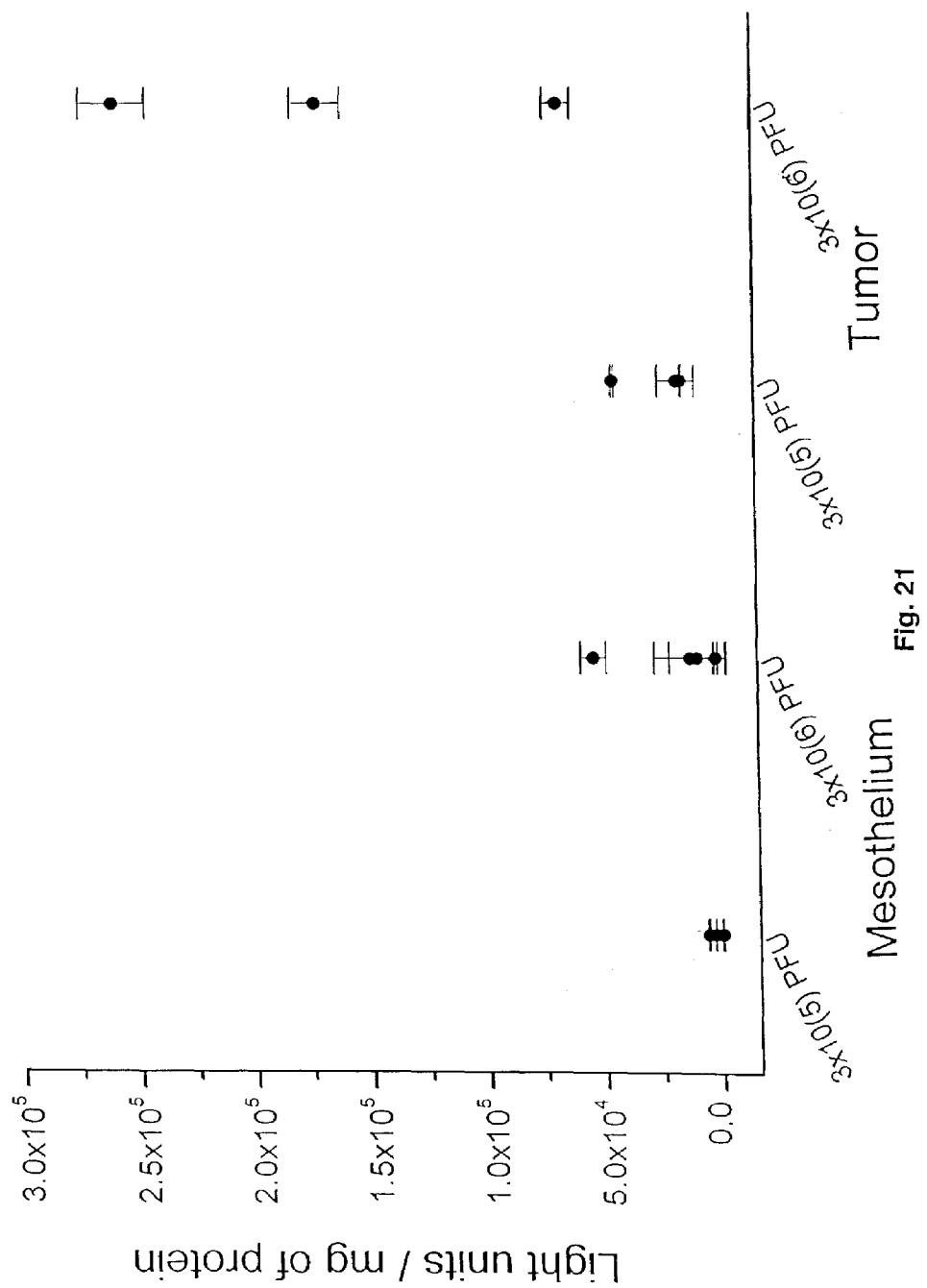

FIG. 21 shows the differential increase in levels of gene transfer in peritoneal mesothelium versus ovarian tumors. Mesothelial strips, taken from patients operated on for benign conditions, were incubated with fiber knob and infected at doses of $3 \times 10^5$ or $3 \times 10^6$ pfu with Ad5lucRGD. After incubation at 37° C. for 30 h, the tissues were lysed and the luciferase activity was determined. Results of similar infections in tumor explants are presented. Data normalized for protein concentration is shown. Each point represents the mean±standard deviation of determinations in three mesothelial explants from the same patient. Data from four representative patients are shown.

Figure 22:
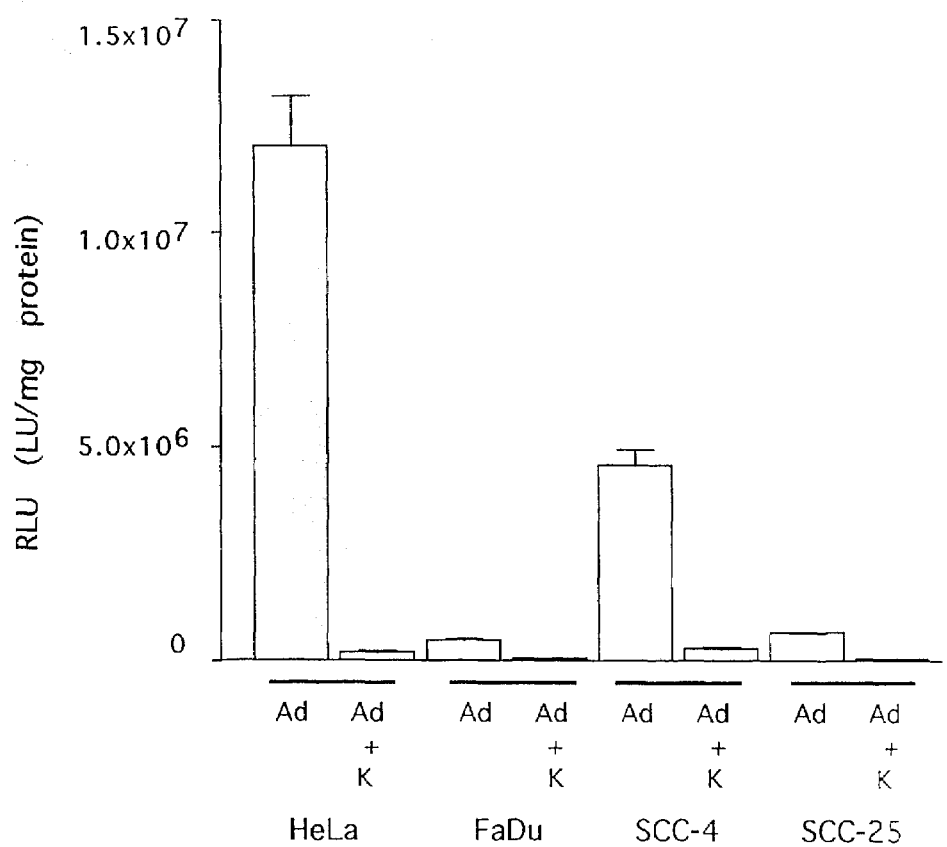

FIG. 22 shows gene transfer to human cell lines via the luciferase expressing replication-defective adenoviral vector AdCMVLuc. Human SCCHN cell lines FaDu, SCC-4 and SCC-25, and the positive control cervical carcinoma cell line HeLa, were infected at an moi of 10 vector particles per cell and analyzed for the product of the luciferase gene after 48 hours. Blocking experiments were also carried out with recombinant fiber knob (K). Results represent the mean±SEM and represent relative light units (RLU) of luciferase per milligram of total cellular protein.

Figure 23:
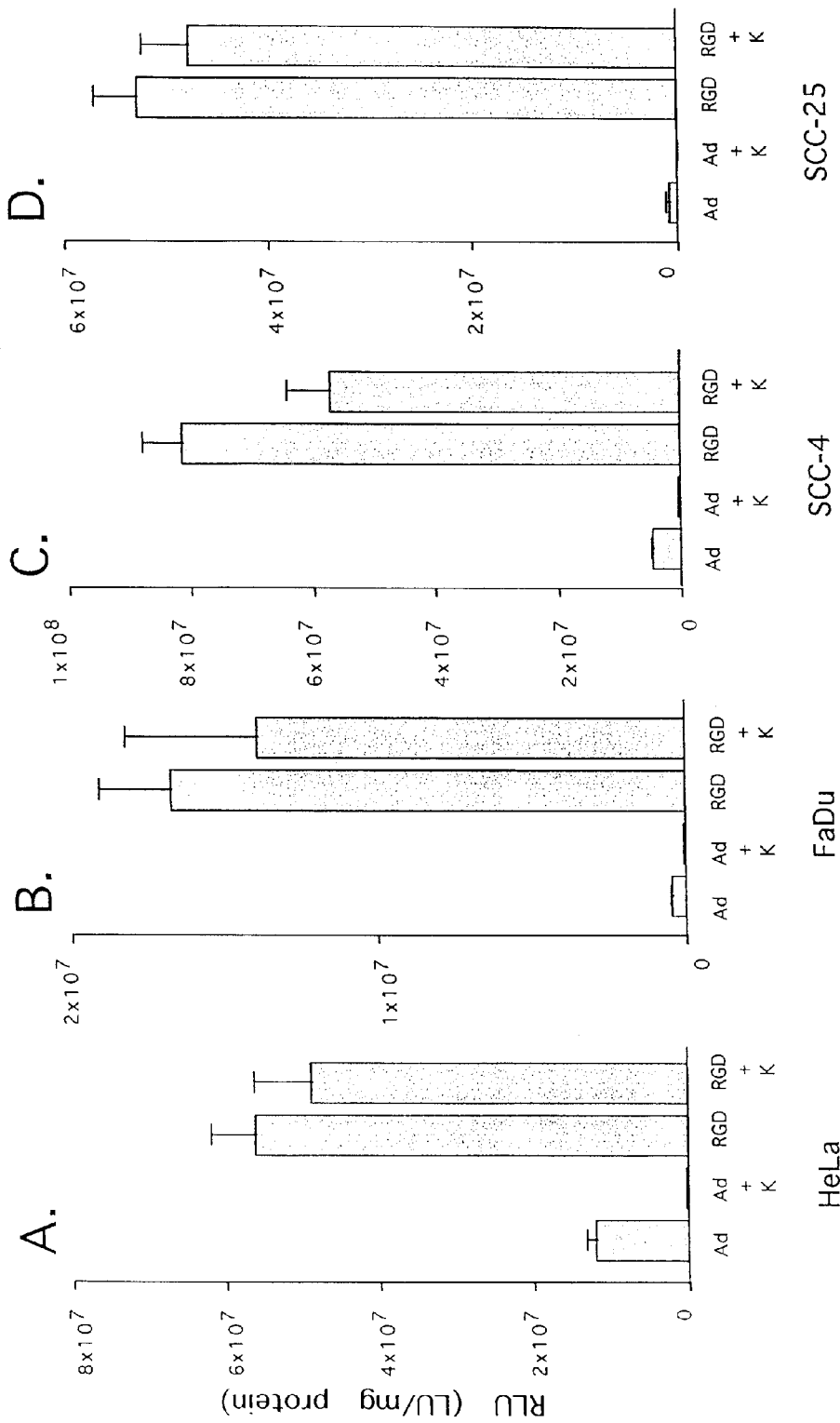

FIG. 23(A-D) shows a comparison of the relative efficiencies of gene transfer with AdCMVLuc and Ad5lucRGD into human SCCHN tumor cell lines. Ad5lucRGD contains an RGD motif in the HI loop of the fiber to targeting to specific integrins. Analysis was carried out as for FIG. 22. Results represent the mean±SEM.

Figure 24:
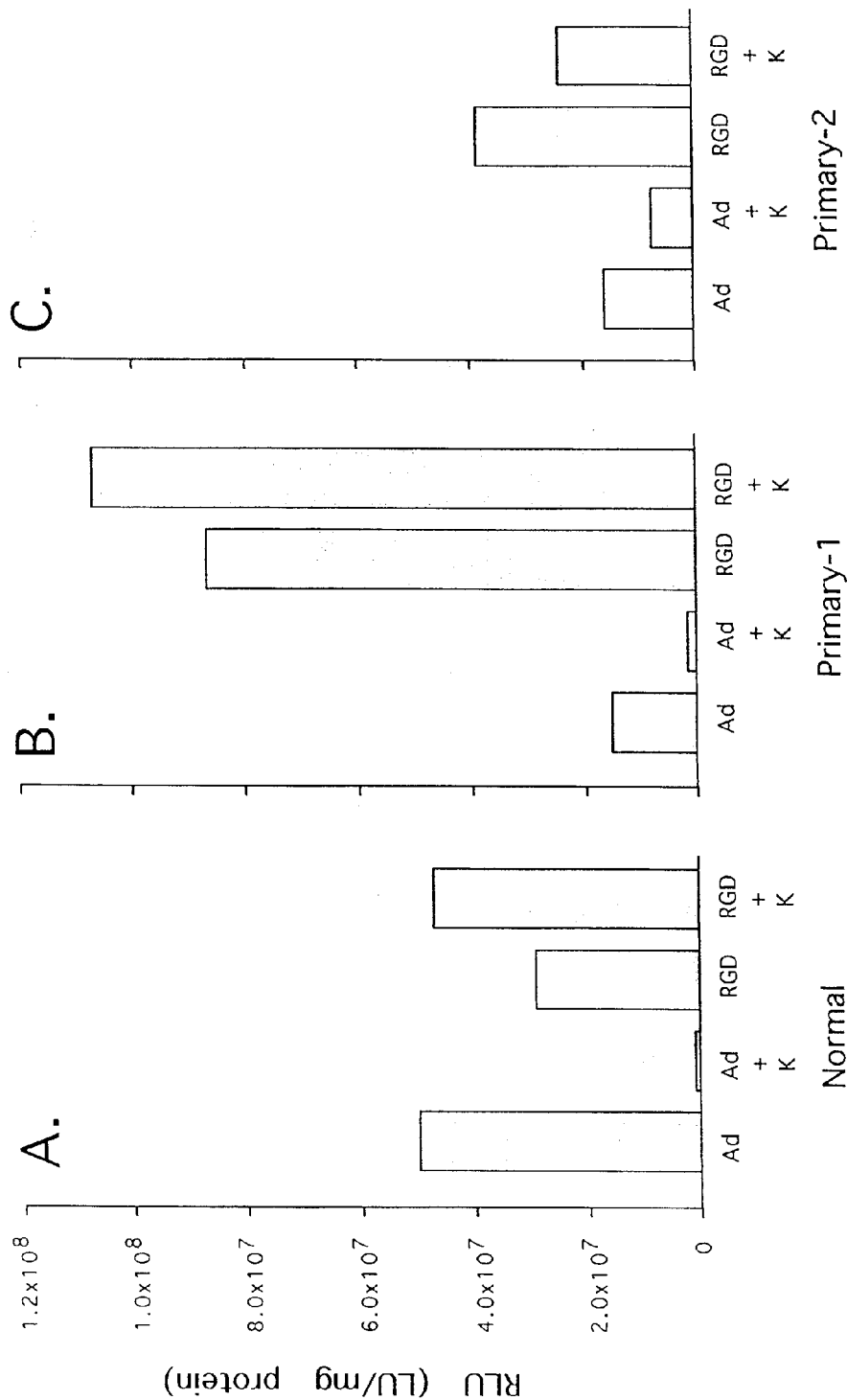

FIG. 24 shows analysis of the relative gene transfer frequency of AdCMVLuc and Ad5lucRGD for SCCHN cell lines. Infection of target cells was at an moi of 250 particles per cell. Forty-eight hours after infection, cells were analyzed for the product of the reporter gene by in situ hybridization with a probe for luciferase mRNA.

Figure 25:
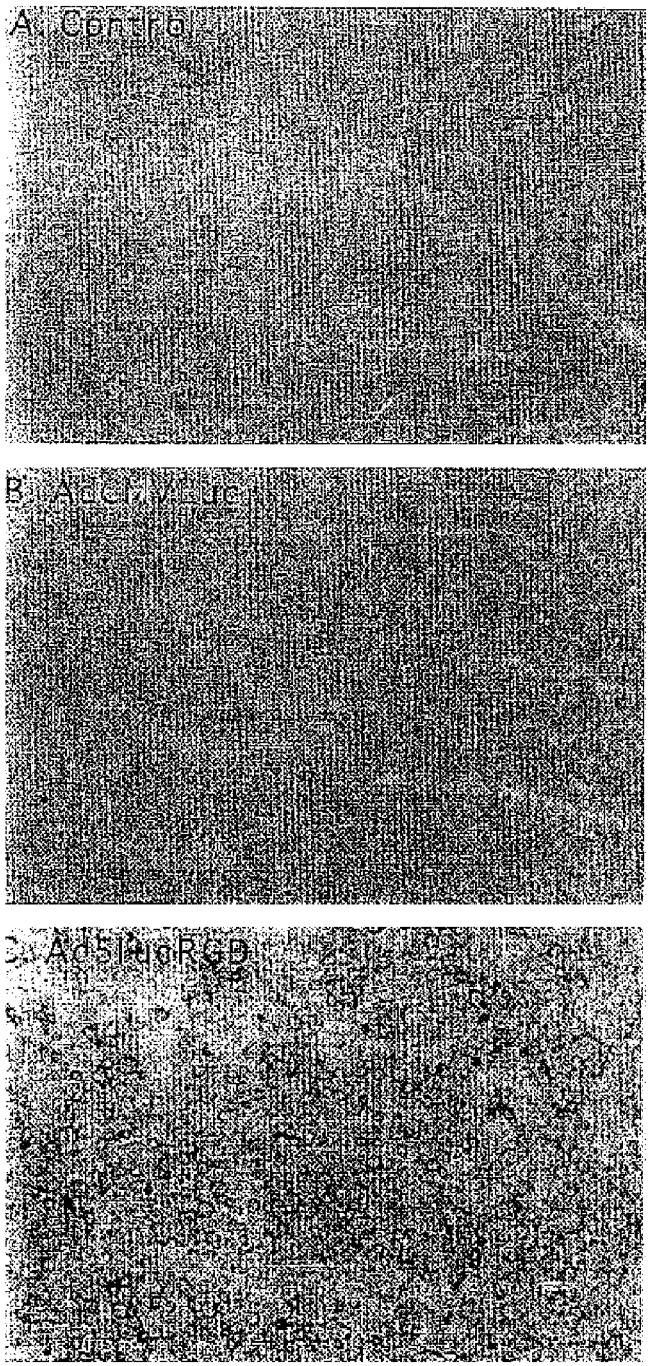

FIG. 25 shows analysis of the differential gene transfer efficiency of AdCMVLuc and Ad5lucRGD for primary SCCHN tumor and normal buccal mucosa. Fresh tissue (10-20 mg) was prepared from patients and infected with the adenoviral vectors ($10^6$ vector particles/mg tissue). Twenty-four hours later, cells were analyzed for the expression of the luciferase gene product.

Figure 26A:
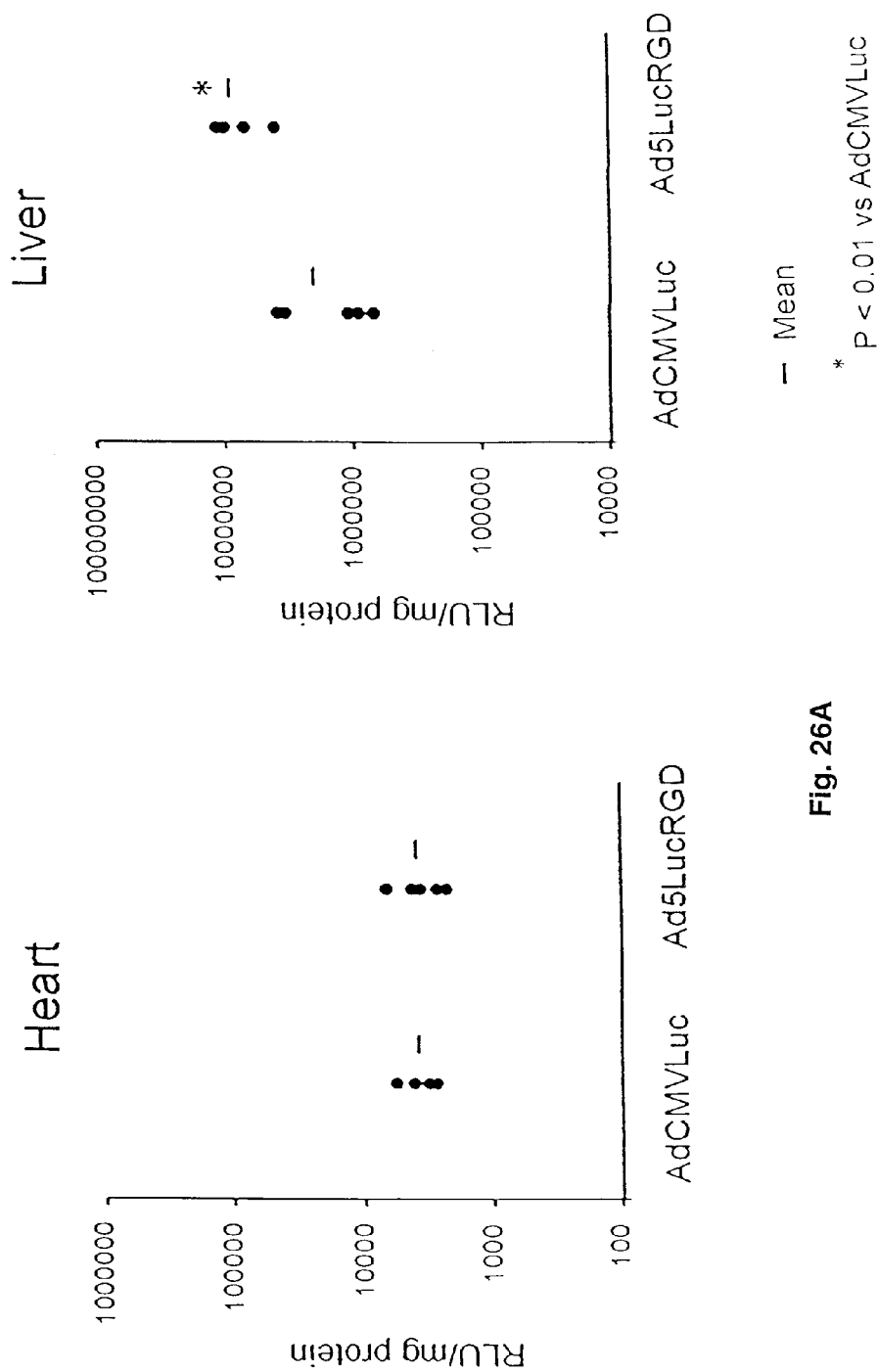
Figure 26B:
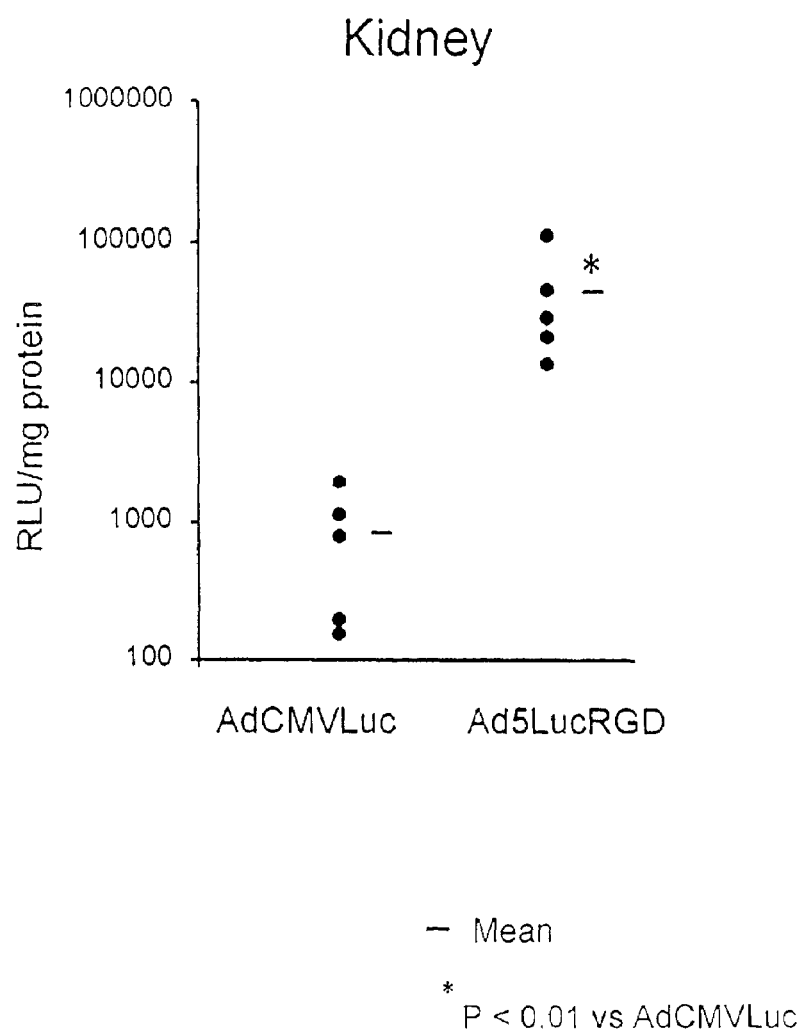
Figure 26C:
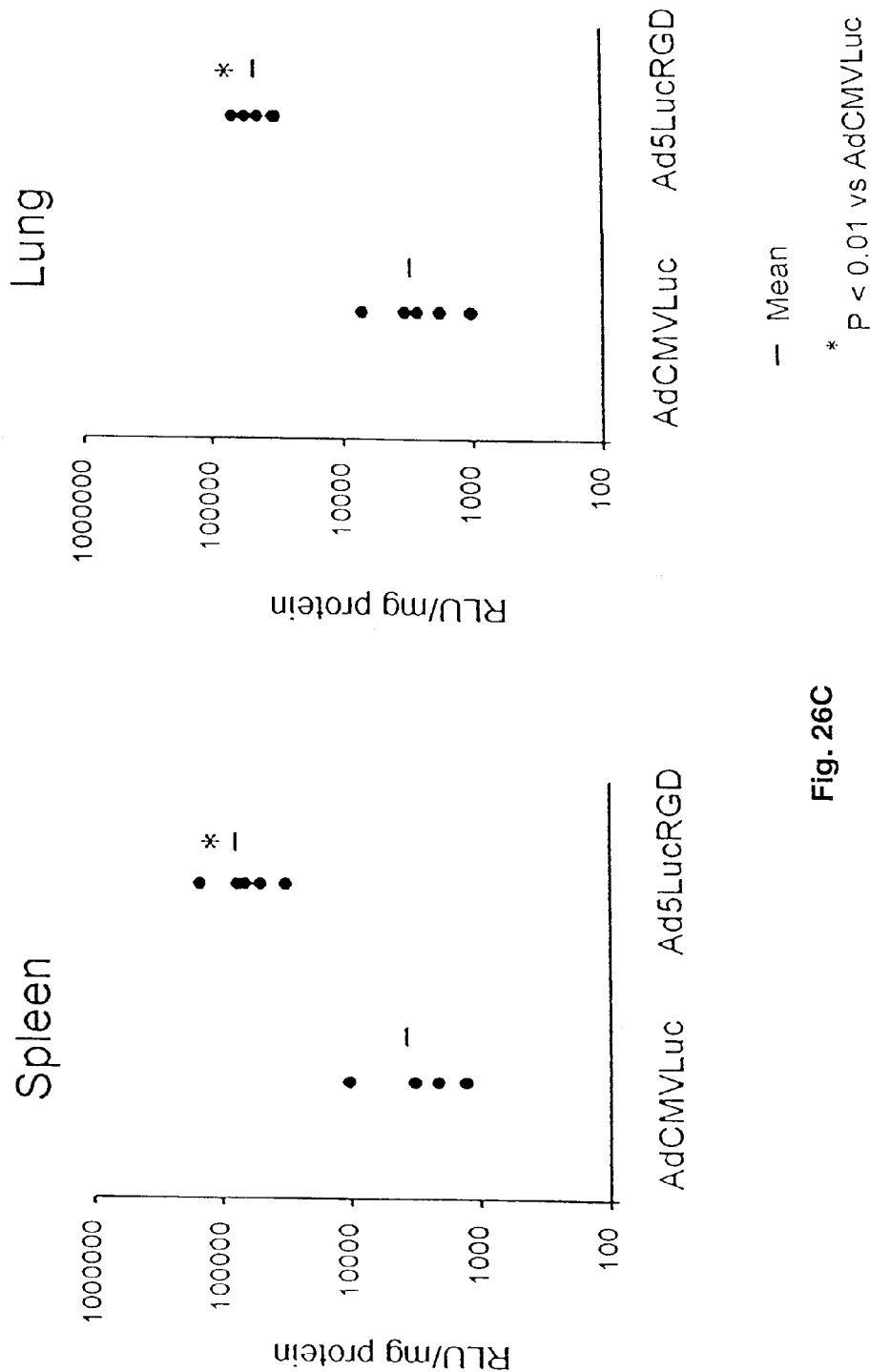

FIG. 26 shows gene expression in various organs following systemic administration of vector. $10^9$ pfu of either AdCMVLuc or AdlucRGD, in a volume of 200 µl of hepes buffered saline, were injected into the lateral tail vein of female C57black6 mice aged 8-10 weeks. Three days later, mice were sacrificed and organs harvested and snap frozen in polypropylene tubes immersed in ethanol and dry ice. Frozen organs (the entire organ in each case) were ground to a fine powder using a mortar and pestle cooled in an ethanol/dry ice bath. Organ powders were lysed using lysis buffer (Promega, Madison, Wis.) at room temperature for 20 min. Lysates were subjected to three freeze-thaw cycles then centrifuged at 14,000 rpm in a microfuge for fifteen minutes. Supernatant luciferase activity was assessed using a Luciferase Assay System kit (Promega) according to the manufacturer's instructions. Relative light units (RLU) were measured using a Berthold luminometer. Protein content of lysates was determined using a BioRad DCprotein assay kit according to manufacturer's instructions. Results are expressed as RLU per mg of protein, with each point representing one mouse, and the mean of 5 mice indicated by a bar. Statistical analysis was performed by analysis of variance of the logarithmically transformed date, with significance accepted $p<0.05$. Data shown is representative of three separate experiments.

Figure 27:
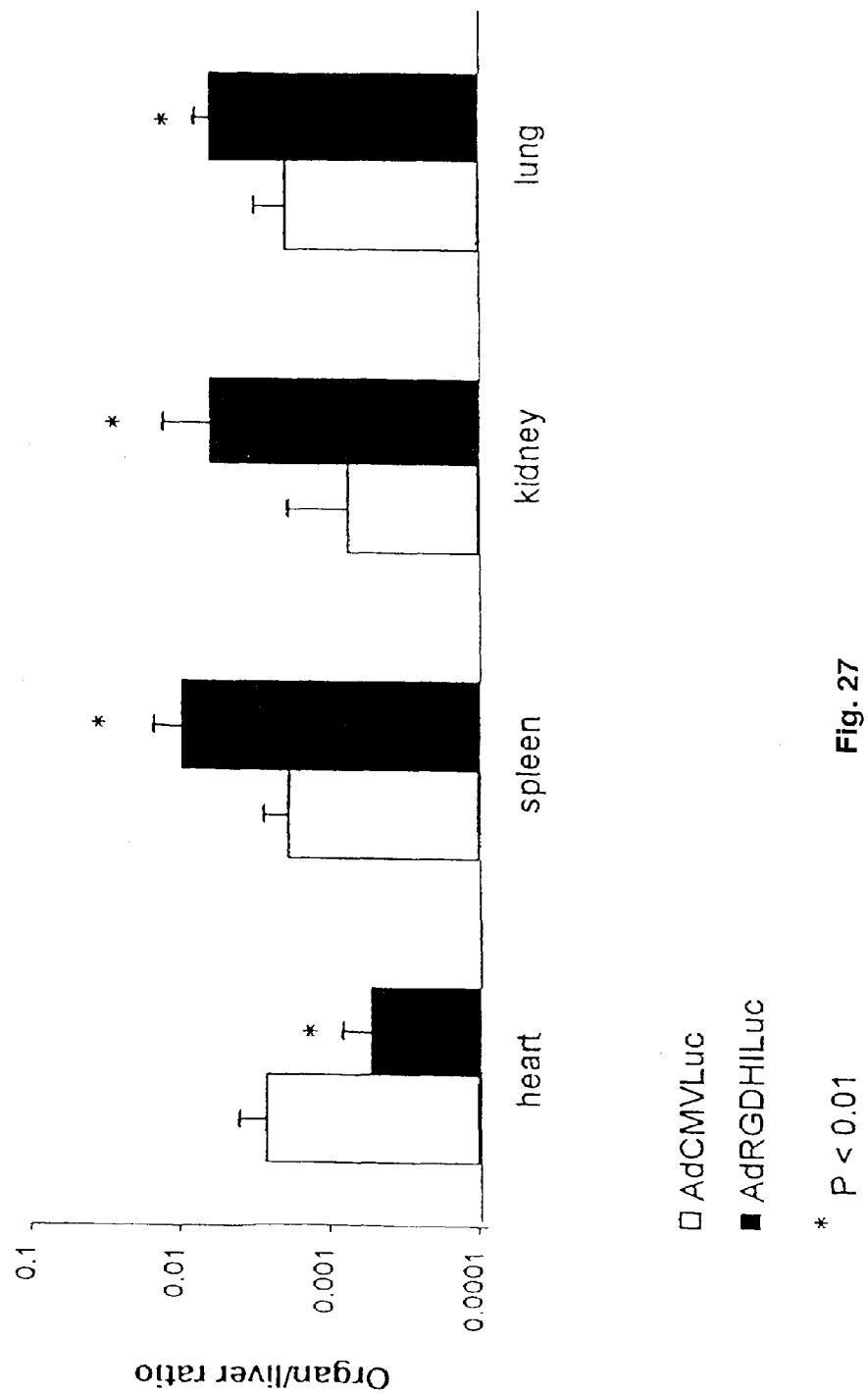

FIG. 27 shows the ratios of luciferase expression in various organs compared to liver expression. Luciferase expression in the various organs was determined as in FIG. 26, then for each individual mouse the indicated organ/liver ratio of expression was determined. Data are mean (±SD) of the ratios.

DETAILED DESCRIPTION OF THE INVENTION

Figure 1:
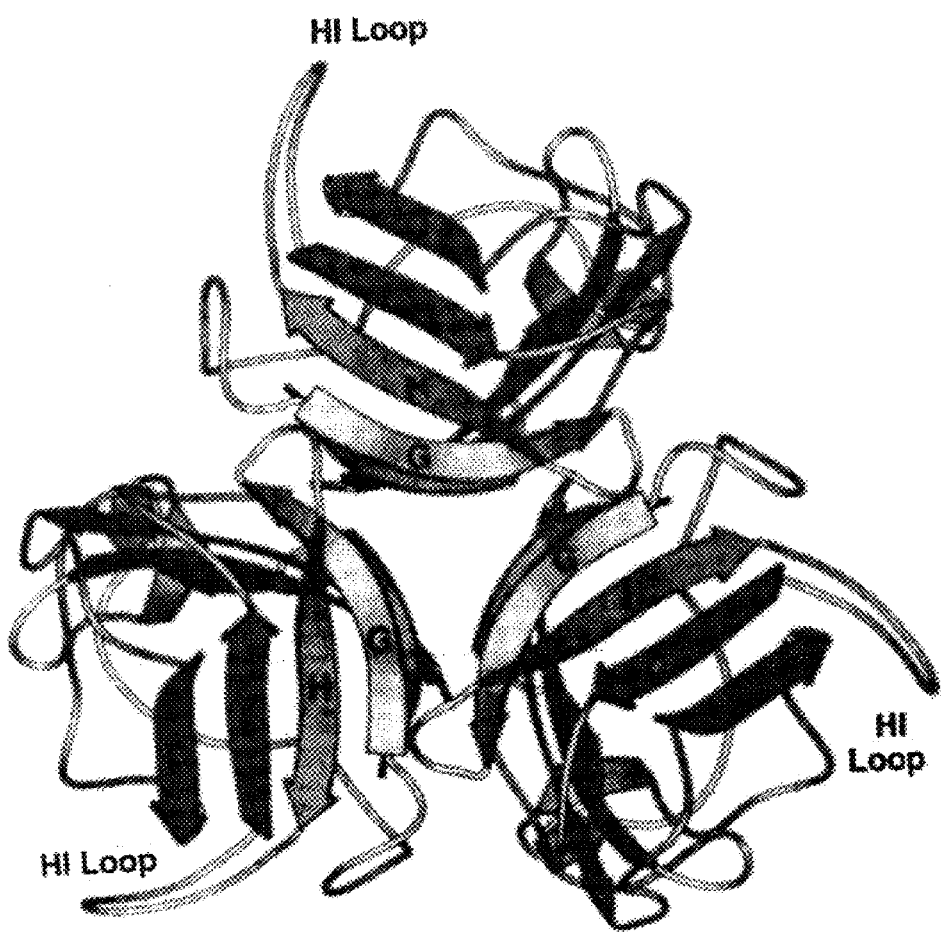
FIG. 1 shows a 3D model of Ad5 fiber knob. The trimer forms a propeller-like structure when it is viewed along the threefold symmetry axis from above. The HI loop, exposed outside the knob, connects the β-strands H and I which are involved in the formation of the cell binding site. (Reproduced from reference 47 by permission).

FIG. 1 shows a schematic 3D model of the fiber knob protein. The HI loop does not contribute to intramolecular interactions in the knob and therefore, incorporation of additional protein sequence should not affect the trimerization of the fiber. In addition, the loop consists mostly of hydrophilic amino acid residues and is exposed outside the knob. It demonstrates a high degree of flexibility, creating an optimal environment for ligand incorporation. Furthermore, the lengths of HI loops vary significantly in knobs of different adenovirus serotypes. This fact suggests that alterations of the original structure of the loop, such as insertions and deletions, should be compatible with the correct folding of the entire knob domain. Finally, the HI loop is not involved in the formation of the putative cell-binding site localized in the knob.

One approach to modifying the adenovirus fiber protein by manipulating the HI loop of the knob has been developed. It is possible to incorporate heterologous amino acid sequences into the HI loop without affecting the correct folding of the fiber polypeptide and its biological functions. Further, these results suggest that the HI loop of the knob locale offers advantages for strategies designed to achieve tropism modification based upon genetic alteration of capsid proteins.

The present invention demonstrates the utility of the HI loop for incorporation of targeting ligands to allow modification of adenovirus tropism. Specifically, incorporation of an RGD motif peptide into the fiber knob allowed the virus to utilize the RGD/integrin interactions as an alternative infection pathway, dramatically improved the ability of the virus to transduce several types of cells, which normally are refractory to Ad infection. To show the utility of the modified virion, this viral vector was employed as a means for efficient gene transfer to primary ovarian cancer cells. Specifically, the recombinant adenovirus vector containing fibers with RGD-motif in the HI loop was capable of dramatically augmenting gene delivery to target cells via the a CAR-independent cell entry mechanism.

In the present invention, there is provided a composition of matter comprising a modified adenoviral vector containing fiber gene variants.

The present invention is directed towards a recombinant adenovirus, wherein the adenovirus comprises a fiber gene modified in the HI loop domain of the fiber knob. Preferably, the recombinant adenovirus can achieve CAR-independent gene transfer. Additionally, the adenovirus may further comprise an additional modification to the fiber knob, thereby ablating the native tropism of the adenovirus. Optimally, the modified fiber knob retains its ability to trimerize and retains its native biosynthesis profile. For instance, the fiber gene may be modified by introducing a ligand into the HI loop domain of the fiber knob, and representative examples of such ligands are physiological ligands, anti-receptor antibodies and cell-specific peptides. Preferred ligands the sequence Arg-Gly-Asp (RGD), more preferably, sequence CDCRGDCFC. Furthermore, the adenoviral vector encoding the adenovirus further comprises a therapeutic gene, such as the herpes simplex virus-thymidine kinase gene.

The present invention is also directed towards a method of killing tumor cells in an individual in need of such treatment, comprising the steps of: administering to the individual an effective amount of the recombinant adenovirus comprising a fiber gene modified in the HI loop domain of the fiber knob and the herpes simplex virus-thymidine kinase gene; and treating the individual with ganciclovir. Preferably, the administration is systemically.

The present invention is further directed towards a method of providing gene therapy to an individual in need of such treatment, comprising the steps of: administering to the individual an effective amount of the recombinant adenovirus comprising a fiber gene modified in the HI loop domain of the fiber knob and a therapeutic gene. Preferably, the administration is systemically. Representative diseases affecting the individual are cancer, cystic fibrosis and Duchene's muscular dystrophy.

The present invention is still further directed towards a method of increasing the ability of an adenovirus to transduce a cell, comprising the step of: modifying the fiber gene in the HI loop domain of the fiber knob of the adenovirus. Preferably, the fiber gene is modified by introducing a ligand into the HI loop domain of the fiber knob and representative ligands are physiological ligands, anti-receptor antibodies and cell-specific peptides. Preferably, the ligand has the sequence Arg-Gly-Asp (RGD), even more preferably the ligand has the sequence CDCRGDCFC. Generally, the cell is a tumor cell, and may be in vitro, in vivo and ex vivo. Optimally, the adenoviral vector encoding the adenovirus further comprises a therapeutic gene.

In accordance with the present invention, there may be employed conventional molecular biology, microbiology, and recombinant DNA techniques within the skill of the art. Such techniques are explained fully in the literature. See, e.g., Sambrook, Fritsch & Maniatis, "Molecular Cloning: A Laboratory Manual (1982); "DNA Cloning: A Practical Approach," Volumes I and II (D. N. Glover ed. 1985); "Oligonucleotide Synthesis" (M. J. Gait ed. 1984); "Nucleic Acid Hybridization" [B. D. Hames & S. J. Higgins eds. (1985)]; "Transcription and Translation" [B. D. Hames & S. J. Higgins eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984). Therefore, if appearing herein, the following terms shall have the definitions set out below.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure herein according to the normal convention of giving only the sequence in the 5' to 3' direction along the nontranscribed strand of DNA (i.e., the strand having a sequence homologous to the mRNA).

A "vector" is a replicon, such as plasmid, phage or cosmid, to which another DNA segment may be attached so as to bring about the replication of the attached segment. A "replicon" is any genetic element (e.g., plasmid, chromosome, virus) that functions as an autonomous unit of DNA replication in vivo; i.e., capable of replication under its own control. An "origin of replication" refers to those DNA sequences that participate in DNA synthesis. An "expression control sequence" is a DNA sequence that controls and regulates the transcription and translation of another DNA sequence. A coding sequence is "operably linked" and "under the control" of transcriptional and translational control sequences in a cell when RNA polymerase transcribes the coding sequence into mRNA, which is then translated into the protein encoded by the coding sequence.

In general, expression vectors containing promoter sequences which facilitate the efficient transcription and translation of the inserted DNA fragment are used in connection with the host. The expression vector typically contains an origin of replication, promoter(s), terminator(s), as well as specific genes which are capable of providing phenotypic selection in transformed cells. The transformed hosts can be fermented and cultured according to means known in the art to achieve optimal cell growth.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence. A "cDNA" is defined as copy-DNA or complementary-DNA, and is a product of a reverse transcription reaction from an mRNA transcript. An "exon" is an expressed sequence transcribed from the gene locus, whereas an "intron" is a non-expressed sequence that is from the gene locus.

Transcriptional and translational control sequences are DNA regulatory sequences, such as promoters, enhancers, polyadenylation signals, terminators, and the like, that provide for the expression of a coding sequence in a host cell. A "cis-element" is a nucleotide sequence, also termed a "consensus sequence" or "motif", that interacts with other proteins which can upregulate or downregulate expression of a specicif gene locus. A "signal sequence" can also be included with the coding sequence. This sequence encodes a signal peptide, N-terminal to the polypeptide, that communicates to the host cell and directs the polypeptide to the appropriate cellular location. Signal sequences can be found associated with a variety of proteins native to prokaryotes and eukaryotes.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site, as well as protein binding domains (consensus sequences) responsible for the binding of RNA polymerase. Eukaryotic promoters often, but not always, contain "TATA" boxes and "CAT" boxes. Prokaryotic promoters contain Shine-Dalgarno sequences in addition to the -10 and -35 consensus sequences.

The term "oligonucleotide" is defined as a molecule comprised of two or more deoxyribonucleotides, preferably more than three. Its exact size will depend upon many factors which, in turn, depend upon the ultimate function and use of the oligonucleotide. The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use the method. For example, for diagnostic applications, depending on the complexity of the target sequence, the oligonucleotide primer typically contains 15-25 or more nucleotides, although it may contain fewer nucleotides.

Primers are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence or hybridize therewith and thereby form the template for the synthesis of the extension product.

As used herein, the terms "restriction endonucleases" and "restriction enzymes" refer to enzymes which cut double-stranded DNA at or near a specific nucleotide sequence.

"Recombinant DNA technology" refers to techniques for uniting two heterologous DNA molecules, usually as a result of in vitro ligation of DNAs from different organisms. Recombinant DNA molecules are commonly produced by experiments in genetic engineering. Synonymous terms include "gene splicing", "molecular cloning" and "genetic engineering". The product of these manipulations results in a "recombinant" or "recombinant molecule".

A cell has been "transformed" or "transfected" with exogenous or heterologous DNA when such DNA has been introduced inside the cell. The transforming DNA may or may not be integrated (covalently linked) into the genome of the cell. In prokaryotes, yeast, and mammalian cells for example, the transforming DNA may be maintained on an episomal element such as a vector or plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or ancestor by mitosis. A "cell line" is a clone of a primary cell that is capable of stable growth in vitro for many generations. An organism, such as a plant or animal, that has been transformed with exogenous DNA is termed "transgenic".

As used herein, the term "host" is meant to include not only prokaryotes but also eukaryotes such as yeast, plant and animal cells. A recombinant DNA molecule or gene can be used to transform a host using any of the techniques commonly known to those of ordinary skill in the art. Prokaryotic hosts may include *E. coli, S. tymphimurium, Serratia marcescens* and *Bacillus subtilis*. Eukaryotic hosts include yeasts such as *Pichia pastoris,* mammalian cells and insect cells, and more preferentially, plant cells, such as *Arabidopsis thaliana* and *Tobaccum nicotiana*.

Two DNA sequences are "substantially homologous" when at least about 75% (preferably at least about 80%, and most preferably at least about 90% or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. In another example, the coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

As used herein, "fragment," as applied to a polypeptide, will ordinarily be at least 10 residues, more typically at least 20 residues, and preferably at least 30 (e.g., 50) residues in length, but less than the entire, intact sequence. Fragments can be generated by methods known to those skilled in the art, e.g., by enzymatic digestion of naturally occurring or recombinant protein, by recombinant DNA techniques using an expression vector that encodes a defined fragment, or by chemical synthesis. The ability of a candidate fragment to exhibit an enzyme characteristic (e.g., binding to a specific antibody, or exhibiting partial enzymatic or catalytic activity) can be assessed by methods described herein. Purified fragments or antigenic fragments can be used to generate new regulatory enzymes using multiple functional fragments from different enzymes, as well as to generate antibodies, by employing standard protocols known to those skilled in the art.

A standard Northern blot assay can be used to ascertain the relative amounts of mRNA in a cell or tissue obtained from plant or other transgenic tissue, in accordance with conventional Northern hybridization techniques known to those persons of ordinary skill in the art. Alternatively, a standard Southern blot assay may be used to confirm the presence and the copy number of the gene in transgenic systems, in accordance with conventional Southern hybridization techniques known to those of ordinary skill in the art. Both the Northern blot and Southern blot use a hybridization probe, e.g. radiolabelled cDNA, either containing the full-length, single stranded DNA or a fragment of the DNA sequence at least 20 (preferably at least 30, more preferably at least 50, and most preferably at least 100 consecutive nucleotides in length). The DNA hybridization probe can be labelled by any of the many different methods known to those skilled in this art.

The labels most commonly employed for these studies are radioactive elements, enzymes, chemicals which fluoresce when exposed to untraviolet light, and others. A number of fluorescent materials are known and can be utilized as labels. These include, for example, fluorescein, rhodamine, auramine, Texas Red, AMCA blue and Lucifer Yellow. A particular detecting material is anti-rabbit antibody prepared in goats and conjugated with fluorescein through an isothiocyanate. Proteins can also be labeled with a radioactive element or with an enzyme. The radioactive label can be detected by any of the currently available counting procedures. The preferred isotope may be selected from $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$.

Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Many enzymes which can be used in these procedures are known and can be utilized. The preferred are peroxidase, β-glucuronidase, β-D-glucosidase, β-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

As used herein, native biosynthesis profile refers to desirable characteristics of the fiber knob retained subsequent to modification (e.g. incorporation of modified fibers into the virion, correct structural association of the modified fiber knob with the adenovirus capsid protein, etc.).

The following examples are given for the purpose of illustrating various embodiments of the invention and are not me ant to limit the present invention in any fashion.

EXAMPLE 1

Cells 293 human kidney cell line transformed with Ad5 DNA was purchased from Microbix (Toronto, Ontario, Canada). HeLa human adenocarcinoma cells, A549 human lung carcinoma cells, human umbilical vein endothelial cells (HU-VEC) and human embryonal rhabdomyosarcoma cells (RD) were obtained from American Type Culture Collection (Manassis, Va.). Human ovarian carcinoma cell lines SKOV3.ip1 and OV-4 were obtained from Janet Price (M.D. Anderson Cancer Center, Houston, Tex.) and Timothy J. Eberlein (Brigham and Women's Hospital, Boston, Mass.), respectively, and were maintained in Dulbecco's modified Eagle's medium (DMEM)-Ham's F12 from Mediatech (Herndon, Va.) supplemented with 10% fetal calf serum (FCS) (Hyclone Laboratories, Logan, Utah), 100 units/ml penicillin, 100 µg/ml streptomycin at 37° C. and 5% $CO_2$. Primary ovarian carcinoma cells were isolated as follows: Malignant ascites of epithelial ovarian carcinoma were collected during surgery at the Hospital of the University of Alabama at Birmingham, Division of the Gynecologic Oncology, and were classified by the pathologist. The materials obtained after the surgical procedure were processed to remove red blood cells and then dead cells. Briefly, lysis buffer was added into small aliquoted primary materials, after incubation for 2 minutes at room temperature, complete medium was added and centrifuged, the cell pellet was resuspended in complete medium and mixed with Ficoll 400 solution (Gibco-BRL, Gaithersburg, Md.), after centrifuge, the cell band was collected. To remove dead cells, the collected cells were resuspended in medium containing 5% FBS, the Ficoll solution was underlaied, after centrifuge, the live cells were harvested and transferred to another tube an stored in FBS supplemented to 2% of Dimethyl Sulfoxide (Fisher Scientific) at −150° C. Three human head and neck tumor cell lines and HeLa cells were obtained from the American Type Culture Collection (Manassis, Va.). Studied cell lines were FaDu pharyngeal squamous cell carcinoma), SCC-4 and SCC-25 (tongue squamous cell carcinoma), and HeLa. FaDu cells were grown in Minimal Essential Medium supplemented with 10% fetal bovine serum (FBS) (Gibco-BRL, Grand Island, N.Y.), 0.1 mM non-essential amino acids and 1.0 mM sodium pyruvate. SCC-4 and SCC-25 cells were grown in Ham's F12/Dulbecco's modified Eagle's medium at a 1:1 ratio by weight (DMEM/F12) with 10% FBS, 2 mM glutamine and 400 ng/ml hydrocortisone (Sigma, St. Louis, Mo.). All cells were cultured at 37° C. in a 5% $CO_2$ atmosphere. Primary human SCCHN tumor samples obtained during surgery (The University of Alabama at Birmingham, Birmingham, Ala.) were transported to the laboratory and processed for experiments. Briefly, tumor or normal tissue was minced finely, distributed into approximately equal aliquots, weighed and then overlaid with 100 μl OptiMEM (GibcoBRL). For all experiments, 10-20 mg/sample of tissue was used.

EXAMPLE 2

Enzymes, Protein Assay and Antibodies

Restriction endonucleases, T4 DNA ligase, T4 polynucleotide kinase, and proteinase K were from either New England Biolabs (Beverly, Mass.) or Boehringer Mannheim (Indianapolis, Ind.).

The concentrations of purified proteins were determined by the Bradford protein assay (Bio-Rad, Hercules, Calif.) with bovine gamma globulin as the standard.

Anti-fiber monoclonal antibodies 4D2 (19) and 1D6.14 (14) were generated at the University of Alabama at Birmingham Hybridoma Core Facility. Anti-FLAG monoclonal antibody M2 and M2-affinity gel were purchased from Scientific Imaging Systems (Eastman Kodak, New Haven, Conn.). Anti-$\alpha_v\beta_3$ integrin monoclonal antibody LM609 and anti-$\alpha_v\beta_3$ integrin monoclonal antibody P1F6 were purchased from Chemicon (Chemicon, Temecula, Calif.) and Gibco-BRL (Gibco BRL, Gaithersburg, Md.), respectively. Anti-CAR monoclonal antibody RmcB was obtained from R. W. Finberg (Dana-Farber Cancer Institute, Harvard Medical School, Boston, Mass.).

Mouse anti-CAR monoclonal antibody (RmcB) prepared as ascites fluid was obtained from Dr. R. L. Crowell (Hahnemann University, Philadelphia, Pa.) (Lee et al., J. Virol. 62:1647, 1988). The anti-αVβ3 mAb, LM609, anti-αVβ3 complex mAb, P1F6, anti-α2β1 mAb, BHA2.1 and anti-α3β1, MAB1992 were purchased from Chemicon International INC (Temecula, Calif.). Control mouse IgG and FITC-conjugated F(ab')2 fragments of anti-mouse IgG were purchased from Sigma (St. Louis, Mo.).

EXAMPLE 3

Flow Cytometry and Indirect Flow Cytofluorometry

Cells grown in T75 flasks were versene released and resuspended in SM buffer (Hepes buffered saline, 0.1% sodium azide, 1% BSA) at $2 \times 10^6$ cell/ml. Two hundred thousand cells were incubated with 5 μgml LM609, P1F6, RmcB, or no primary mAb (negative control) in 200 μl SM for 2 hours at 4° C. Cells were then washed with SM and incubated with 5 μg/ml secondary FITC-labeled goat anti-mouse IgG serum (Jackson Labs, West Grove, Pa.) for 1 hour at 4° C. After SM wash, $10^4$ cells per sample were analyzed by flow cytometry at the UAB FACS Core Facility.

Cultured cells were washed with PBS and harvested with Versene (GibcoBRL) for 15 min. Detached cells were centrifuged and resuspended in PBS containing 1% bovine serum albumin (BSA) and 0.1% sodium azide (1% BSA/PBS) at a concentration of $10^5$ cells/ml. The cells were then incubated with primary antibodies for 1 h on ice. Subsequently, the cells were washed and incubated with FITC-conjugated anti-mouse IgG for an additional 1 h. After washing with 1% BSA/PBS, the cells were analyzed by flow cytometry.

EXAMPLE 4

Expression and Purification of Six-His-Tagged Recombinant Proteins

Recombinant Ad5 fiber knob protein was expressed in *E. coli* and purified by immobilized metal ion affinity chromatography (IMAC) on Ni-nitrilotriacetic acid (NTA)-Sepharose (Qiagen, Valencia, Calif.) as recommended by the manufacturer. Human adenovirus serotype 2 penton base protein was expressed in *Spodoptera frugiperda* Sf9 cells by recombinant baculovirus AcNPV-PbWT (18) provided by P. Boulanger (Institute of Biology, Monpellier, France). The penton base protein was purified from baculovirus infected cells by two step ion-exchange chromatography utilizing DEAE-Sepharose FF column (Pharmacia, Piscataway, N.J.) followed by purification on POROS HQ column (PerSeptive Biosystems, Mass.). Recombinant fiber proteins expressed in baculovirus-infected Sf9 cells were purified by chromatography on Ni-NTA-Sepharose. The protein concentrations were determined by the Bradford protein assay (Bio-Rad, Hercules, Calif.) with bovine gamma globulin as the standard.

EXAMPLE 5

Elisa

The six-His tagged fibers were immobilized on Ni-NTA HiSorb Strips (Qiagen) essentially as described in the Qiagen manual. Briefly, 200 μl of fiber protein solution at a concentration 1 μg/ml was added to each well of an Ni-NTA HiSorb Strip and incubated for 1 hour at room temperature. After incubation the wells were washed four times with phosphate-buffered saline (PBS)-Tween buffer, and 200 gl of anti-fiber antibody (1:2000 dilution) or anti-FLAG antibody (1:140 dilution) was added. Following incubation at room temperature for 2 hours the wells were washed again and incubated with 1:10,000 dilution of goat anti-mouse immunoglobulin G conjugated to horseradish peroxidase (HRP) for 45 minutes. The wells were then washed four times with PBS-Tween buffer and developed with 2',2'-azino-bis(3-ethylbenzthiazoline-6-sulfonic acid) (ABTS) (diammonium salt). The ABTS-HRP reaction was read in a microtiter plate reader set at 405 nm.

Solid-phase binding assay was also performed by the following method (Sharma et al., 1997, Virology. 239:150-7). Briefly, purified fiber proteins or adenoviral virions were diluted in 50 mM carbonate-bicarbonate, pH 9.6 buffer to a concentration of 10 μg of protein per milliliter and 100 μl aliquots were added to the wells of a 96-well Nunc-Maxisorp ELISA plate. Plates were incubated overnight at 4° C. and then blocked for 2 hours at room temperature with 200 μl of blocking buffer (20 mM Tris-HCl, pH 7.5, 150 mM NaCl, 0.5% casein). Wells were then washed three times with the wash buffer (20 mM Tris-HCl, pH 7.5, 150 mM NaCl). Purified integrin ($\alpha_v\beta_3$ (Chemicon International Inc., Temecula, Calif.) diluted in binding buffer (20 mM Tris-HCl, pH 7.5, 150 mM NaCl, 2 mM $CaCl_2$, 1 mM $MgCl_2$, 1 mM $MnCl_2$, 0.5% casein) to concentrations ranging from 0.04 to 0.5 μg/ml, was added to the wells in 100 μl aliquots. After overnight incubation at 4° C. the wells were washed three times with washing buffer containing 2 mM $CaCl_2$, 1 mM $MgCl_2$ and 1 mM $MnCl_2$. Bound integrin was detected with mouse monoclonal anti-human integrin $\alpha_v$-subunit antibody VNR139 (GibcoBRL, Gaithersburg, Md.). VNR139 antibody diluted 1:3000 in binding buffer was added to the wells in 100 μl aliquots, incubation was continued for 1 hour at room temperature and then the wells were washed again. The ELISA plate was then developed with VECTASTAIN kit (Vector Laboratories, Burlingame, Calif.) as recommended by the manufacturer. Color development was stopped by the addition of 1N $H_2SO_4$ and plates were read in a microtiter plate reader set at 490 nm.

EXAMPLE 6

Construction of Recombinant Plasmids

E1-deleted Ad5 vectors, AdCMVLuc and AdCMVLacZ, which express firefly luciferase and bacterial β-galactosidase (18), respectively, were obtained from R. D. Gerard, the University of Texas Southwestern Medical Center, Dallas, Tex.

To generate a gene encoding the Ad5 fiber knob domain with the HI loop deleted, a PCR technique was employed. The following two pairs of primers were used:

F1: (5' TAAGGATCCGGTGCCATTACAGTAGGAAACAAAAATAA 3')    (SEQ ID No. 1);

R1: (5' CATAGAGTATGCAGATATCGTTAGTGTTACAGGTTTAGTTTTG 3')    (SEQ ID No. 2);

F2: (5' GTAACACTAACGATATCTGCATACTCTATGTCATTTTCATGG3')    (SEQ ID No. 3); and

R2: (5' CCCAAGCTTACAATTGAAAAATAAACACGTTGAAACATAAC 3')    (SEQ ID No. 4)

were used to amplify portions of the fiber gene corresponding to positions 1159 to 1451 and 1642 to 1747, respectively. In addition, the second fragment also contains 43 bp of Ad5 DNA adjacent to the 3' end of the fiber gene in the viral genome. The fragments generated were then gel purified, mixed, and joined by the third PCR using primers F1 and R2. The product obtained contains a unique EcoRV restriction site in place of the deleted portion of the sequence encoding the HI loop, as well as BamHI and HindIII sites inserted into the ends of the molecule to facilitate subsequent cloning. This DNA fragment was cleaved with BamHI and HindIII and cloned into the BamHI-HindIII-digested bacterial expression vector pQE30 (Qiagen, Santa Clara, Calif.), resulting in plasmid pQE.KNOBΔHI.

To construct an expression plasmid with the FLAG sequence incorporated into the HI loop of the fiber, oligonucleotides TACACTAAACGGTACCCAGGAAACAG-GAGACACAACTGACTACAAGGACGACGATGACAA-GCC (SEQ ID No. 5) and CGCTTGCATCGTCGTCCT-TGTAGTCAGTTGTGTCTCCTGTTTCCTGGGTACCGT-TTAGTGTA (SEQ ID No. 6) were annealed to form a duplex and cloned into EcoRV-digested pQE.KNOBΔHI. The plasmid containing the duplex in the correct orientation was designated pQE.KNOB$_{HI}$FLAG.

The transfer plasmids for the generation of recombinant baculoviruses expressing chimeric fibers were made as follows: a BglII-MfeI fragment from PQE.KNOB$_{HI}$FLAG was utilized to replace the BglII-MfeI fragment in the vector pBS.F5.UTR which has been described previously (25), thereby generating pBS.F5$_{HI}$FLAG. A BssHII-XhoI fragment from pBS.F5$_{HI}$FLAG was then cloned into the BssHII-XhoI-digested baculovirus transfer vector pFastBac1 (Life Technologies, Gaithersburg, Md.), resulting in pFB.F5$_{HI}$FLAG. To introduce the six-His purification tag into the amino terminus of the chimeric fiber, the BamHI-BssHII fragment of pFB.F5$_{HI}$FLAG was replaced with a synthetic duplex made with oligonucleotides GATCCATG-CATCACCATCACCATCACAAG (SEQ ID No. 7) and CGCGCTTGTGATGGTGATGGTGATGCATG (SEQ ID No. 8), which encodes MetHis$_6$Lys. The resultant plasmid, pFB6H.F5$_{HI}$FLAG, contains the gene coding for a fiber with an amino-terminal six-His tag and FLAG peptide inserted into the HI loop. To derive a similar plasmid containing the fiber gene with the HI loop coding sequence unmodified, the BssHII-MfeI fragment in pFB6H.F5$_{HI}$FLAG was replaced with homologous fragment from pNEB.PK3.6 (25), generating pFB6H.F5. In order to clone the gene encoding the fiber with the FLAG sequence in the HI loop into the fiber shuttle vector pNEB.PK3.6, a BstXI-MfeI fragment of the wild type fiber gene contained in this plasmid was replaced with a BstXI-MfeI fragment from pQE.KNOB$_{HI}$FLAG, thereby creating pNEB.F5$_{HI}$FLAG.

To facilitate the generation of recombinant adenovirus genomes by homologous recombination in *Escherecia coli*, plasmid pTG3602 (7), obtained from Transgene (Strasbourg, France), was engineered to create a specialized vector suitable for modifications of the fiber gene. To accomplish this end, an NdeI site localized in the fiber gene was employed. Plasmid pTG3602 was partially digested with NdeI and ligated with an NdeI-SwaI linker, TACCCATT-TAAATGGG (SEQ ID No. 9). This plasmid, containing a SwaI site in the fiber gene was designated pVK50.

A recombinant adenovirus genome containing a gene encoding the fiber-FLAG protein was generated by homologous DNA recombination in *E. coli* BJ5183 between pVK50 linearized with SwaI and the 3-kb EcoRI fragment from pNEB.F5$_{HI}$FLAG containing the gene of interest, as described by Chartier et al. (7). The newly generated genome was then excised from the resultant plasmid, pVK300, and employed to rescue the virus.

In order to generate a recombinant Ad5 fiber gene encoding the fiber with the RGD-4C peptide within the HI loop of the knob domain, a duplex made of oligos CAC ACT AAA CGG TAC ACAGGA AAC AGG AGA CAC AAC TTG TGA CTG CCG CGG AGA CTG TTT CTGCCC (SEQ ID No. 10) and GGG CAG AAA CAG TCT COG CGG CAG TCACAA GTT GTG TCT CCT GTT TCC TGT GTA CCG TTT AGT GTG (SEQ ID No. 11) was cloned into EcoRV site of previously designed plasmid pQE.KNOBΔHI (21), thereby generating pQE.KNOB.RGD$_{HI}$.

To make a shuttle vector suitable for the generation of the viral genome of interest, a BstXI-MunI-fragment of the modified fiber gene containing RGD-4C coding sequence was subcloned from pQE.KNOB.RGD$_{HI}$ into the fiber shuttle vector pNEB.PK3.6 (Krasnykh, et al., 1996, J. Virol. 70:6839-46) cleaved with BstXI and MunI. In order to obtain Ad5 genome containing fiber-RGD gene, the resultant plasmid, pNEB.PK.F$_{HI}$RGD, was then utilized for homologous DNA recombination with SwaI-digested pVK50 in *Escherichia coli* BJ5183 as previously described. The plasmid obtained as a result of this recombination was designated pVK503.

Firefly luciferase gene was excised from plasmid pGEM$^R$-luc (Promega, Madison, Wisc.) as 1.7 kb BamHI-XhoI-fragment and cloned into BamHI-XhoI-digested pcDNA3 (Invitrogen, Carlsbad, Calif.), resulting in pcD- NA.Luc. To destroy PacI and ClaI sites in the luciferase ORF, a synthetic duplex consisting of oligos CAA ATA CAAAGG ATA TCA GGT GGC CCC CGC TGA ATT GGA GT (SEQ ID No. 12) and CGA CTC CAA TTC AGC GGG GGC CAC CTG ATA TCC TTT GTA TTT GAT (SEQ ID No. 13) was used to replace 41 bp PacI-ClaI-fragment in pcDNA.Luc, thereby generating pcLucPC1.

In order to make a shuttle vector containing this modified luciferase gene in the context of expression cassette, the gene was cloned in pACCMVpLpA (Becker, et al. 1994, Meth. Cell Biol. 43:161-89) as follows. Plasmid pcLucPC1 was cleaved with BamHI, treated with Klenow enzyme to fill-in the ends, and then cut with XhoI. The cloning vector, pACCMVpLpA, was cut with EcoRI, treated with Klenow enzyme and then cleaved with SalI. The ligation of these two DNA molecules resulted in pACCMV.LucΔPC. This plasmid was then used for homologous DNA recombination with ClaI-linearized pVK503 in order to generate pVK703, containing the genome of Ad5lucRGD.

To derive a recombinant baculovirus expressing fiber-RGD, the transfer vector pFB.F5$_{HI}$FLAG was modified in a following way. First, EcoRI linker, CGG CGA ATT CGC, was incorporated into ClaI site of pFB.F5$_{HI}$FLAG, resulting in pFB.F5.RI. Then, NcoI-MunI-fragment of pNEB.PK.F$_{HI}$RGD containing 3' portion of the fiber-RGD gene was used to replace an NcoI-MunI-fragment in pFB.F5.RI, generating pFB.F5$_{HI}$RGD. This plasmid was then used to generate recombinant baculovirus genome via site-specific transposition by utilizing Bac-to-Bac kit (Gibco BRL, Gaithersburg, Md.) according to manufacturer recommendations.

Adenoviruses were propagated on 293 cells and purified by centrifugation in CsCl gradients according to a standard protocol (15). Determination of virus particle titer was accomplished spectrophotometrically by the method described by Maizel et al. (28), with a conversion factor of $1.1 \times 10^{12}$ viral particles per absorbance unit at 260 nm. To determine the titer of infectious viral particles on 293 cells, a plaque assay was employed as described by Mittereder et al. (32). Recombinant baculoviruses expressing chimeric fibers were generated with a Bac-to-Bac expression kit from Gibco-BRL (Life Technologies) according to the manufacturer's protocol.

EXAMPLE 7

Adenovirus Infection Assay

To assess adenoviral infection, $10^5$ cells of each cell line were plated in triplicate into each well of 12-well plates in the presence of 1 ml of culture media. The cells were then incubated overnight to allow adherence. Initially, the cells were incubated in 300 μl/well of the media containing 2% FBS, with or without knob protein at 20 μg/ml of the final concentration, for 15 min. To each well was then added infection complexes mixed in a final volume of 300 μl containing: a) AdCMVLuc or Ad5lucRGD at 10-250 pfu/cell, or b) AdCMVLuc/knob protein or Ad5lucRGD/knob protein at 20 μg/ml. The cells were incubated at 37° C. in 5% $CO_2$ for 1 h, then were washed with phosphate buffered saline pH 7.4 (PBS) and then supplemented with 1 ml of complete media. Forty-eight hours after infection, the cells were rinsed with PBS and assayed for luciferase expression by enzyme assay or in situ hybridization of luciferase mRNA. For all luciferase enzyme assays, the cells were lysed in 200 μl of Promega Madison, Wisc.) lysis buffer. Ten μl of each sample was subsequently mixed with 50 μl of Promega luciferase assay reagent according to the manufacturer's instructions and duplicate determinations of triplicate samples were assayed in a Berthold luminometer. For primary tissues, the minced aliquots of tissue were incubated in 1 ml of OptiMEM, with or without 20 μg/ml of knob protein, for 30 min and then transduced by AdCMVLuc or Ad5lucRGD ($5 \times 10^7$ pfu/10 mg tissue) for 1 h. After replacing the media (OptiMEM containing antibiotics), the tissue was incubated for an additional 24 h. The tissue was then homogenized and centrifuged. The collected supernatant was then employed for the luciferase assay and measurement of protein concentration.

EXAMPLE 8

In Situ Hybridization of Luciferase mRNA

A protocol for the in situ hybridization technique is described (Bucy et al., J. Exp. Med. 180:1251, 1994; Panoskaltsis-Martari & Bucy, BioTechniq. 18:300, 1995). Briefly, cells were plated into each well of 12-well plates in the presence of 1 ml of culture media. After the cells reached subconfluency, they were transduced by AdCMVLuc or Ad5lucRGD at 250 pfu/cell for 1 h. After an additional 48 h incubation, the cells were rinsed with PBS and resuspended in Versene (GibcoBRL). After centrifugation, the cells were resuspended in DEPC-treated PBS at a concentration of $10^6$ cells/ml. Cells in 100 μl of each sample were attached to the slide glass by a cytospin. The cells were then rinsed with PBS and fixed for 1 h in 3% paraformaldehyde at room temperature. Fixed cells were treated with 0.2 M HCl to inhibit endogenous alkaline phosphatase activity, acetylated with 0.1 M triethanolamine and acetic anhydride to decrease background staining, and hybridized overnight at 50° C. with 400 pg/ml/kb of relevant riboprobe in hybridizing solution. The hybridization solution consisted of 50% formamide, 4×SSC, 1× Denhardt's solution (Sigma), 500 mg/ml heat-denatured herring sperm DNA, 250 mg/ml yeast transfer RNA, and 10% dextran sulfate. After hybridization, the cells were rinsed with 2×SSC followed by sodium chloride-Tris-EDTA buffer and treated with RNase A (20 mg/ml in sodium chloride-Tris-EDTA) for 30 min at 37° C. to remove excess nonhybridized probe. Next, a series of progressive stringency washes were performed with 2×SSC, 1×SSC, 0.5×SSC and Tris-NaCl (0.15 M), pH 7.5, with normal horse serum. The cells were then stained with alkaline phosphatase-conjugated anti-digoxigenin antibody at a concentration of 1:5,000 for 1 h. The cells were next washed with Tris-NaCl, and transferred to a basic Tris buffer with $MgCl_2$ (pH 9.5). Finally, the slides were incubated with the enzyme substrate solution (nitroblue tetrazolium/BCIP, Boehringer-Mannheim) overnight in dark, humid chambers at 4° C. The color reaction was stopped by rinsing the slides in Tris-EDTA buffer, pH 8.0.

EXAMPLE 9

FLAG Accessibility Assay

To demonstrate the binding of the FLAG-tagged fiber protein incorporated into intact virions of Ad5F$_{HI}$FLAG to anti-FLAG M2 monoclonal antibody, an immunoprecipitation assay was employed. Ad5F$_{HI}$FLAG or AdCMVLuc purified on CsCl gradients were dialyzed against HEPES buffer (10 mM HEPES, 1 mM $MgCl_2$, 10% glycerol, [pH 7.4]) and absorbed onto M2-affinity gel (Eastman Kodak) as follows. Fifty microliters of dialyzed virus containing $10^{11}$ viral particles was mixed with 100 μl of M2-affinity gel equilibrated with HEPES buffer containing 50 mM NaCl and 0.5% bovine serum albumin (BSA) and then incubated overnight at 4° C. on a rotating wheel. Following incubation, the gel was spun down by brief centrifugation in a microcentrifuge. The supernatant was collected for further analysis and the gel was washed with 0.5 ml of Tris-buffered saline (TBS). Virus was eluted at 4° C. with 50 μl TBS containing 400 μg of FLAG peptide per ml. The supernatant containing unbound material, the wash, and the eluate were then employed to detect the presence of the virus. For this, aliquots of these fractions were treated for 1 hour at 37° C. with sodium dodecyl sulfate, EDTA, and proteinase K at final concentrations of 1%, 10 mM and 100 μg/ml, respectively. The samples were analyzed by agarose gel electrophoresis to detect viral DNA.

EXAMPLE 10

Purification of the Fiber-FLAG Protein by Immunoprecipitation

The recombinant fiber-FLAG protein was expressed in baculovirus infected Sf9 cells as follows. For large scale expression of the fiber-FLAG protein, monolayers of Sf9 cells in T75 flasks were infected with recombinant baculovirus at multiplicity of infection of 5 to 10 and then were incubated at 28° C. until a complete cytopathic effect was observed. At 2 to 3 days postinfection, the cells were scraped, pelleted by low speed centrifugation, and resuspended in lysis buffer (50 mM Tris-HCl pH 8.0, 150 mM NaCl, 1% Nonidet P40, 0.1% SDS, 0.02% sodium azide, 100 μg/ml phenylmethylsulfonyl fluoride, 1 μg of aprotinin per ml). The cells were then incubated on ice for 30 minutes. The lysate was cleared by centrifugation at 12,000×g for 5 minutes in a microcentrifuge. The cleared lysate was mixed with the slurry of M2 affinity gel, and the rest of the procedure was performed as described above for immunoprecipitation of Ad5F$_{HI}$FLAG.

EXAMPLE 11

Trimerization Assay of Recombinant Proteins

To determine whether the fiber proteins expressed in baculovirus infected insect cells could form trimers, these proteins were analyzed by SDS-polyacrylamide gel electrophoresis as described (30). Proteins were either boiled prior to electrophoresis, to dissociate the trimers, or loaded on the gel without denaturation. The trimeric or monomeric configuration of these molecules was thus determined based on their mobilities in the gel.

EXAMPLE 12

Inhibition of Virus Mediated Gene Transfer by Recombinant Fiber Proteins

The ability of the fiber-FLAG chimera to block adenovirus-mediated gene transfer was evaluated in infection inhibition experiments similar to those described previously (17, 24, 34, 36). Briefly, monolayers of HeLa cells grown in a 24-well plate were preincubated at room temperature with serial 10-fold dilutions of either wild type fiber or fiber-FLAG protein prior to infection with a replication defective recombinant adenovirus expressing firefly luciferase, AdCMVLuc. Unbound virus was washed, and the cells were incubated at 37° C. to allow internalization of AdCMVLuc and expression of the luciferase gene. A luciferase assay of the lysates of infected cells was performed 30 hours postinfection with a luciferase assay system from Promega (Madison, Wis.).

EXAMPLE 13

Virus Binding Assay

Human lung carcinoma A549 cells grown in T75 flasks and then harvested with EDTA, washed once with PBS, pelleted and resuspended to a final concentration of $10^7$ cells/ml in DMEM-Ad medium (DMEM, 20 mM Hepes, 0.5% BSA) as described by Wickham et al (45). One-hundred-microliter aliquots of the cells were transferred to 5 ml test tubes and incubated for 1 hour at 4° C. with 100 μl of recombinant fiber diluted in DMEM-Ad medium.

The recombinant adenoviruses AdCMVlacZ and Ad5F$_{HI}$FLAG were purified on a CsCl gradient and dialyzed against buffer containing 10 mM HEPES, 1 mM MgCl$_2$, 10% glycerol [pH 7.4]. Aliquots of both viruses containing 50 mg of viral protein were labeled with $^{125}$I using IODO-BEADS iodination reagent (Pierce, Rockford, Ill.) as described (20). Labeled viruses were purified from unincorporated $^{125}$I by gel filtration on PD-10 columns (Pharmacia, Piscataway, N.J.). Fifty-microliter aliquots of labeled virions with total radioactivities of $10^5$ cpm were then added to A549 cells preincubated with fiber dilutions or PBS and incubated at 4° C. for another hour. The samples were diluted with 4 ml of PBS containing 0.1% BSA, and the cells were pelleted by centrifugation. Supernatant containing unbound virus was aspirated and the radioactivities of cell pellets were determined in a gamma counter.

EXAMPLE 14

Characterization of Recombinant Fibers Expressed in Baculovirus Infected Insect Cells To demonstrate the suitability of using the HI loop of the fiber knob for incorporation of heterologous protein sequences, recombinant fiber proteins expressed in a baculovirus expression system were first employed. This system has already proved its utility for the expression of functional Ad2, Ad3, and Ad5 fiber proteins, as well as Ad3-Ad5 and Ad5-Ad3 fiber chimeras (13, 26, 33, 37).

Figure 2:
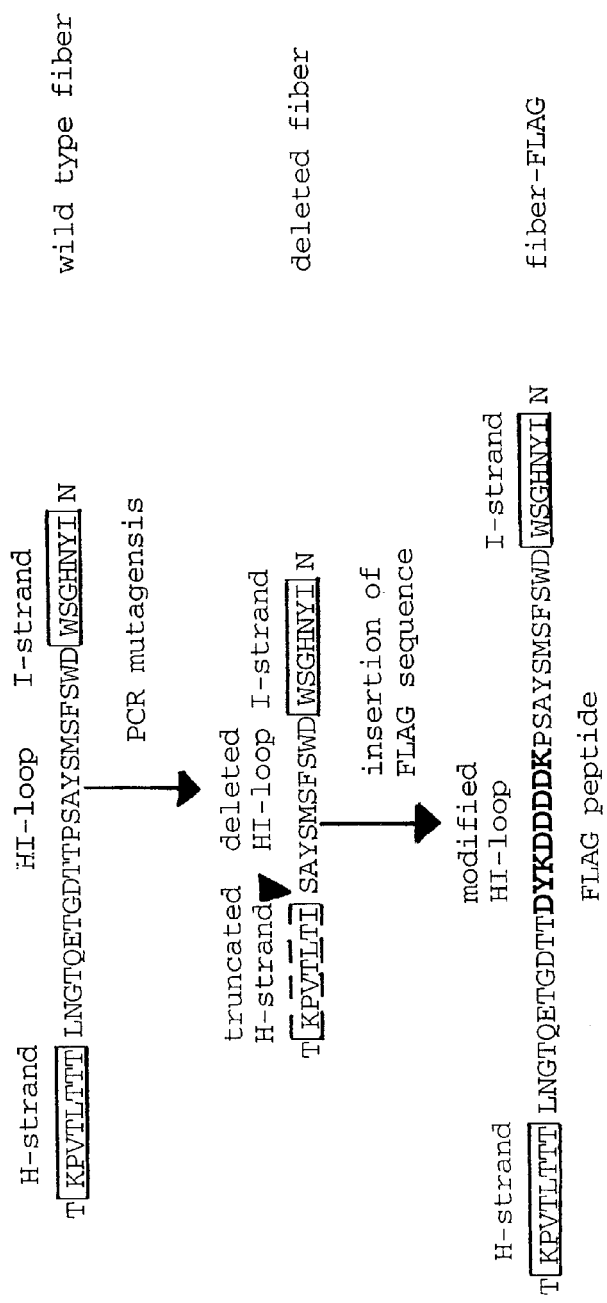
FIG. 2 shows the modifications of the HI loop of the fiber knob. PCR-based mutagenesis was employed to delete a portion of the fiber gene encoding the hypervariable region of the HI loop. A unique EcoRV restriction site was incorporated in place of the deletion to allow the cloning of segments of DNA coding for heterologous protein sequences. In the fiber-FLAG protein, deleted amino acids of the HI loop were restored, and FLAG octapeptide was incorporated between threonine-546 and proline-547. The site of deletion is indicated by a filled triangle.

To achieve this aim, a PCR approach was used to derive a gene encoding the Ad5 fiber knob with a partial deletion in the HI loop. This deletion was engineered to remove amino acids TLNGTQETGDTTP (SEQ ID No. 14) from the HI loop of the fiber knob domain and to introduce a unique EcoRV site in place of the deleted sequence, thereby facilitating the cloning of alternative sequences in this region (FIG. 2). The deletion removed the portion of the HI loop which varies most significantly in the fiber knobs of different serotypes of human adenoviruses. The sequence generated by PCR contained an open reading frame corresponding to two segments of the fiber protein including amino acids glycine-387 through isoleucine-534 and serine-548 through glutamine-581 (coordinates given are according to those of the wild type Ad5 fiber protein sequence). This sequence was cloned into the plasmid vector pQE30.

The newly generated plasmid, pQE.KNOBΔHI, was then utilized as a cloning vector to incorporate a fragment of DNA encoding the FLAG octapeptide (DYKDDDDK (SEQ ID No. 15)), which has been widely used as a detection and purification tag. Thus, this FLAG peptide was exploited in the fiber constructs as a probe to determine whether a heterologous peptide sequence incorporated into the HI loop of the knob was accessible in the context of a trimeric fiber molecule. By incorporating this sequence into the open reading frame of the knob, the previously deleted codons was also restored. Therefore, in the newly generated plasmid, PQE.KNOB$_{HI}$FLAG, the FLAG coding sequence was introduced a s insertions between threonine-546 and proline-547. This plasmid was then employed to construct a full-size recombinant fiber gene in a baculovirus transfer vector. A similar transfer plasmid containing the wild type fiber gene was designed for control purposes. In order to facilitate subsequent purification of the expression products, a sequence encoding an amino-terminal six-His tag was introduced into the designs of both genes. These plasmids were then utilized to generate two recombinant baculoviruses containing fiber genes encoding wild type Ad5 fiber and a fiber protein containing FLAG peptide in the HI loop of the knob domain.

Figure 3A:
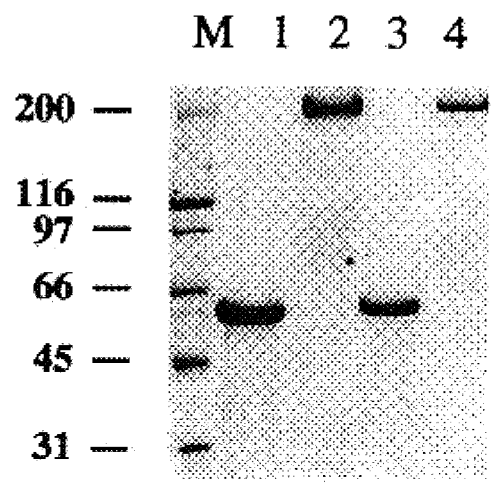
FIG. 3A shows six-histidine-tagged fiber proteins purified on an Ni-NTA-Sepharose column. Lane 1, wild type fiber, boiled; lane 2, wild type fiber, unboiled; lane 3, fiber-FLAG, boiled; lane 4, fiber-FLAG, unboiled; lane M, broad-range protein standards.

Recombinant fibers were recovered from the lysates of baculovirus-infected insect cells with Ni-NTA-Sepharose designed for purification of the six-His-tagged proteins. The yield of purified fibers was in the range of 10 µg of protein per $10^6$ infected cells. Analysis by SDS-polyacrylamide gel electrophoresis of both recombinant proteins showed that they formed stable trimers which, when boiled in the gel loading buffer, dissociated into monomers of the expected molecular mass of 63 kDa (FIG. 3A). This result demonstrated that the incorporation of a short peptide sequence in the HI loop of the knob does not ablate trimerization of the fiber. Therefore, by using the baculovirus expression system one can obtain preparative amounts of the recombinant fibers which were suitable for subsequent assays.

EXAMPLE 15

Accessibility of the FLAG Peptide in the Context of Trimeric Fiber

Figure 3B:
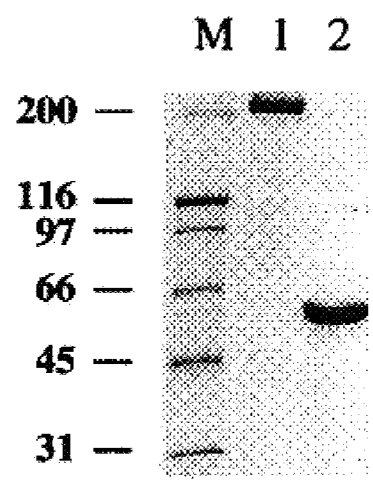
FIG. 3B shows Fiber-FLAG protein purified by immunoprecipitation with anti-FLAG M2 affinity gel. Lane 1, unboiled protein; lane 2, boiled protein; lane M, broad-range protein standards. The numbers on the left indicate molecular masses of marker proteins in kilodaltons.

To find out whether the FLAG peptide introduced into the HI loop of the fiber was available for binding, an assay based on the specific interaction of the FLAG-tagged proteins with an affinity matrix containing anti-FLAG monoclonal antibody was used. For these experiments, the recombinant fiber protein with the FLAG sequence in the HI loop (fiber-FLAG) was purified on an Ni-NTA-Sepharose column and then immunoprecipitated with M2-affinity gel. Protein bound to the matrix was then specifically eluted with FLAG peptide and analyzed on an SDS containing polyacrylamide gel (FIG. 3B). According to this analysis, the fiber-FLAG protein efficiently bound to M2-affinity gel, demonstrating the availability of the FLAG epitope for interaction with an anti-FLAG monoclonal antibody in the context of the trimeric fiber molecule. Importantly, this interaction did not affect the stability of the trimer, suggesting that a recombinant virion containing a novel ligand incorporated in the HI loop of the fiber knob will maintain its structural integrity throughout the binding step of the infection.

EXAMPLE 16

Adenovirus Infection Inhibition by Recombinant Fiber-FLAG Protein

Since it was not known whether the FLAG peptide would possess the ability to target adenovirus to a novel cellular receptor, it was necessary to determine whether the incorporation of this peptide in the HI loop affected proper folding of the cell-binding site localized in the fiber knob. If the HI loop was not involved in the formation of this site and if fiber-FLAG could not bind to the fiber receptor on the cell surface, further attempts to rescue the virus containing this recombinant fiber would inevitably fail. To address these issues a fiber-FLAG recombinant protein was employed to block adenovirus infection in the in vitro setting. This established assay was based on the fact that recombinant adenovirus fiber proteins were capable of blocking infection by the adenovirus from which they were derived. In addition, this inhibition of viral infection takes place in a dose dependent manner.

Figure 4B:
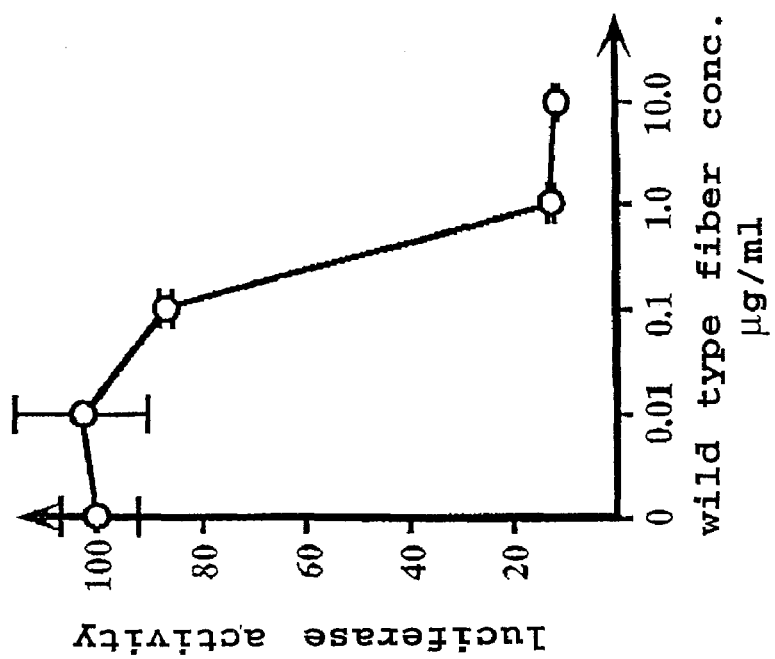
FIG. 4 shows inhibition of adenovirus infectivity by recombinant fiber proteins. HeLa cells were preincubated with either the wild-type (wt) fiber (FIG. 4A) or fiber-FLAG (FIG. 4B) at the indicated concentrations for 10 minutes at room temperature. AdCMVLuc was then added at a multiplicity of infection of 10, and incubation was continued for another 30 minutes at room temperature. The unbound virus was aspirated, complete medium was added, and the cells were transferred to 37° C. After 30 hours the cells were lysed and luciferase activity was determined. Luciferase activities are given as percentages of the activity in the absence of blocking fiber protein. Each point represents the mean of four determinations obtained in one experiment.
Figure 4A:
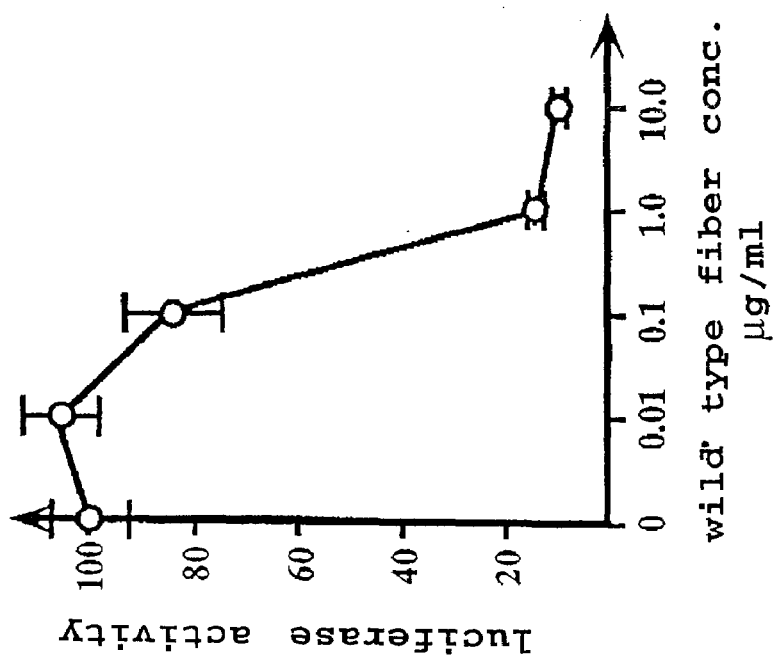

HeLa cells seeded in 12-well tissue culture plates were preincubated with various concentrations of the wild-type Ad5 fiber or fiber-FLAG protein prior to infection with the recombinant Ad5 vector AdCMVLuc, which expresses firefly luciferase as a reporter. Previously, this assay, based on gene transfer by the viral vector, generates data correlating well with a classic binding assay accomplished with radiolabeled virus (24). Thirty hours postinfection, the cells were lysed and the lysates were utilized for the luciferase activity assay (FIG. 4). According to this assay, both fiber proteins blocked infection by AdCMVLuc in a dose dependent manner and demonstrated identical profiles of infection inhibition. Incorporation of heterologous peptide sequences into the HI loop of the fiber knob does not affect the correct folding of the cell-binding site formed by the carboxy-terminal portion of the fiber protein.

EXAMPLE 17

Characterization of the Fiber-FLAG Protein by ELISA

To obtain additional evidence supporting the functional utility of the fiber-FLAG protein, this recombinant protein w as analyzed by ELISA, employing several monoclonal antibodies specific for the FLAG epitope and different conformations of the Ad5 fiber. To achieve this end, wild type fiber and fiber-FLAG proteins expressed in insect cells were absorbed on HisSorb ELISA strips covered with Ni-NTA (Qiagen) and probed with anti-fiber antibody 4D2 or 1D6.14 or anti-FLAG antibody M2. Antibody 4D2 reacts with Ad5 fiber monomers and trimers and was used in this assay as a positive control, whereas antibody 1D6.14 binds to an as yet unidentified conformational epitope in the fiber knob and is trimer specific. The ELISA strips were then developed with goat anti-mouse antibody-HRP conjugate.

Both fiber proteins efficiently reacted with anti-fiber antibodies 4D2 and 1D6.14, thereby suggesting that the 3D structure of the knob in the fiber-FLAG molecule was identical to that of the wild type fiber. In addition, the fiber-FLAG chimera specifically reacted with anti-FLAG antibody M2, confirming the availability of this epitope for binding in the context of a trimeric fiber molecule. Thus, these results validated the data generated earlier by gel electrophoresis analysis of Ni-NTA- or M2-affinity gel purified fiber-FLAG protein, providing the rationale for the incorporation of the fiber-FLAG chimera into the adenovirus virion for further characterization.

EXAMPLE 18

Generation of Ad5F$_{HI}$FLAG

Despite the fact that the data obtained with the recombinant fiber-FLAG protein supported the concept of its functional utility in the context of the adenovirus virion, successful generation of the recombinant virus would support the hypothesis regarding the compatibility of the modifications of the HI loop of the fiber knob with viral functions. Therefore, the fiber-FLAG chimera was incorporated into the adenovirus virion.

In order to derive this virus, a novel genetic method based on homologous DNA recombination in *E. coli* cells was utilized (7). In brief, this method involves recombination between two linear DNA molecules cotransformed into bacterial cells to generate a recombinant adenovirus genome. One of these molecules is plasmid pTG3602, or its derivative, containing the full-size adenovirus genome cloned in the bacterial vector and flanked with two PacI sites. The second partner in this recombination schema is the genetic construct of interest flanked with two segments of adenovirus genomic DNA which dictate the localization of this construct in the adenovirus genome generated as a result of the recombination. This DNA sequence can be either a transgene or the original Ad5 gene, modified by traditional methods of genetic engineering in the context of small recombinant plasmids.

Figure 5:
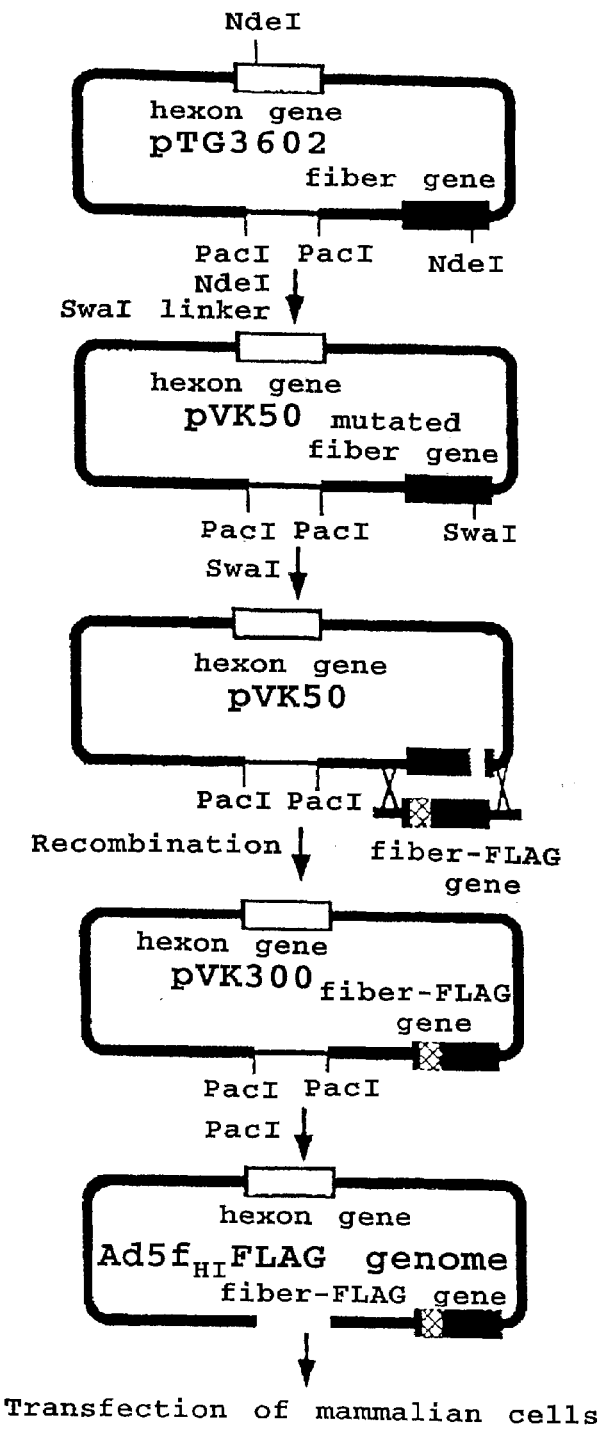
FIG. 5 shows the generation of Ad5F$_{HI}$FLAG. The master plasmid, pTG3602, was modified to incorporate a unique SwaI restriction site in the fiber gene, thereby creating plasmid pVK50, suitable for fiber modifications. The genome of Ad5F$_{HI}$FLAG was generated by homologous DNA recombination in E. coli between the DNA fragment containing the fiber-FLAG gene and plasmid pVK50 linearized by SwaI digestion. To rescue the virus, the resulting plasmid, pVK300, which contains the complete adenoviral genome with a modified fiber gene, was cleaved with PacI and w as then used to transfect 293 cells.

To reduce the nonrecombinant background generated by pTG3602, prior to transformation this plasmid was cleaved with a restriction enzyme within or near the region of the genome where the final construct was going to be inserted. Although this method has numerous advantages compared to traditional generation of recombinant adenovirus genomes by homologous recombination in mammalian cells, it requires the existence of unique restriction sites within the regions of the adenovirus genome to be modified. However, Ad5 genomic DNA in pTG3602 does not contain any unique restriction sites in the fiber gene, which limits its utility for modifications of fiber. Thus, to overcome this limitation, this plasmid was modified by inserting a unique cleavage site for the restriction endonuclease SwaI into the fiber gene. To this end, one of the two NdeI sites present in Ad5 DNA and localized 47 bp downstream from the fiber gene's 5' end was converted into SwaI site by insertion of an SwaI-linker (FIG. 5). The plasmid generated, pVK50, was then utilized for homologous recombination with the fragment of DNA containing the gene encoding fiber-FLAG flanked with viral DNA adjacent to the fiber gene in the Ad5 genome. As a result of this recombination, a plasmid, pVK300, containing a modified fiber gene in the context of the complete adenovirus genome was derived. Adenovirus DNA was released from pVK300 by PacI digestion and used for transfection of 293 cells to rescue the virus as described (7).

DNA isolated from CsCl gradient-purified virions of the newly generated virus, Ad5F$_{HI}$FLAG, was subjected to PCR analysis and cycle sequencing to confirm the presence of the FLAG coding sequence in the fiber gene incorporated in the genome. According to both analyses, Ad5F$_{HI}$FLAG indeed contained the fiber gene of interest.

EXAMPLE 19

Characterization of Ad5F$_{HI}$FLAG by a Cell-Binding Assay

The yield of this virus grown on 293 cells, approximately $10^{11}$ PFU per preparation obtained from 20 75 cm$^2$ tissue culture flasks, was comparable to what was normally obtained when growing the wild-type Ad5. Also, there was no delay in plaque formation dynamics either when rescuing the virus or when expanding it. These observations suggested that the introduction of the FLAG peptide in the HI loop of the knob did not significantly affect the correct folding of the fiber molecule and its biological functions.

Figure 6A:
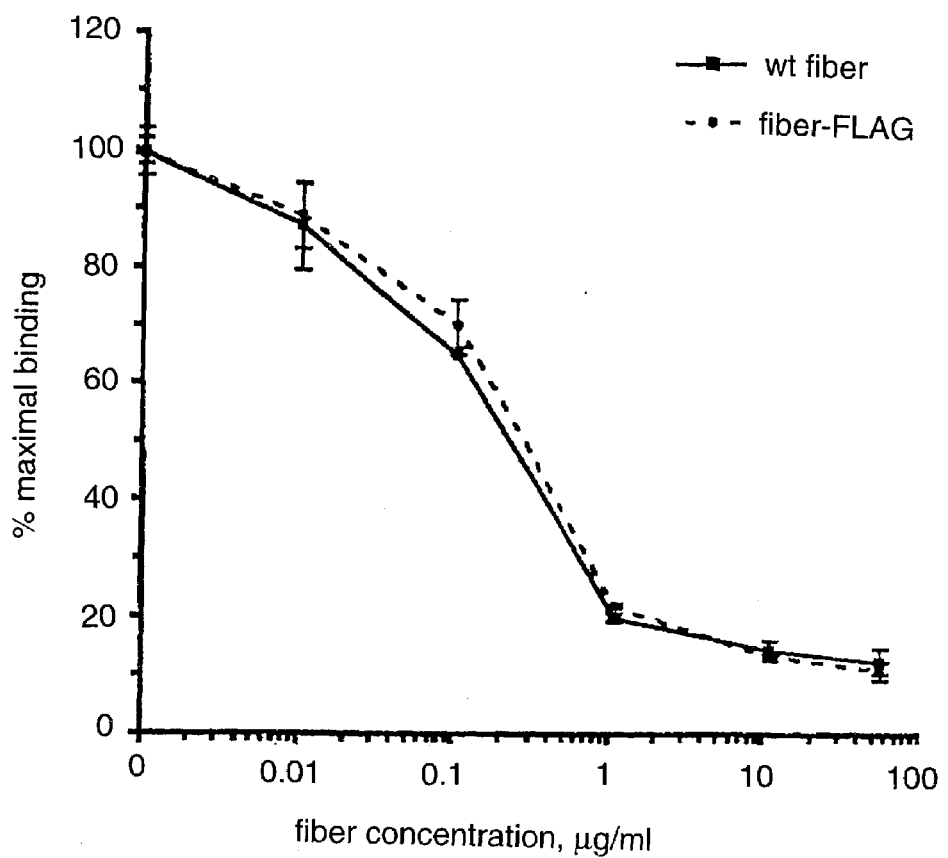
FIG. 6 shows an adenovirus binding assay. Aliquots of A549 cells containing $10^5$ cells per sample were incubated for 1 hour at 4° C. with serial dilution of either wild-type (wt) Ad5 fiber or fiber-FLAG. Virions of Ad5CMVLacZ (FIG. 6A) and Ad5F$_{HI}$FLAG (FIG. 6B) labeled with $^{125}$I were added to samples, and incubation was continued for an additional hour. The cells were washed with 4 ml of PBS containing 0.1% BSA and pelleted by low-speed centrifugation. Radioactivities of samples were determined with a gamma counter. Each point represents the mean of two determinations obtained in one experiment.
Figure 6B:
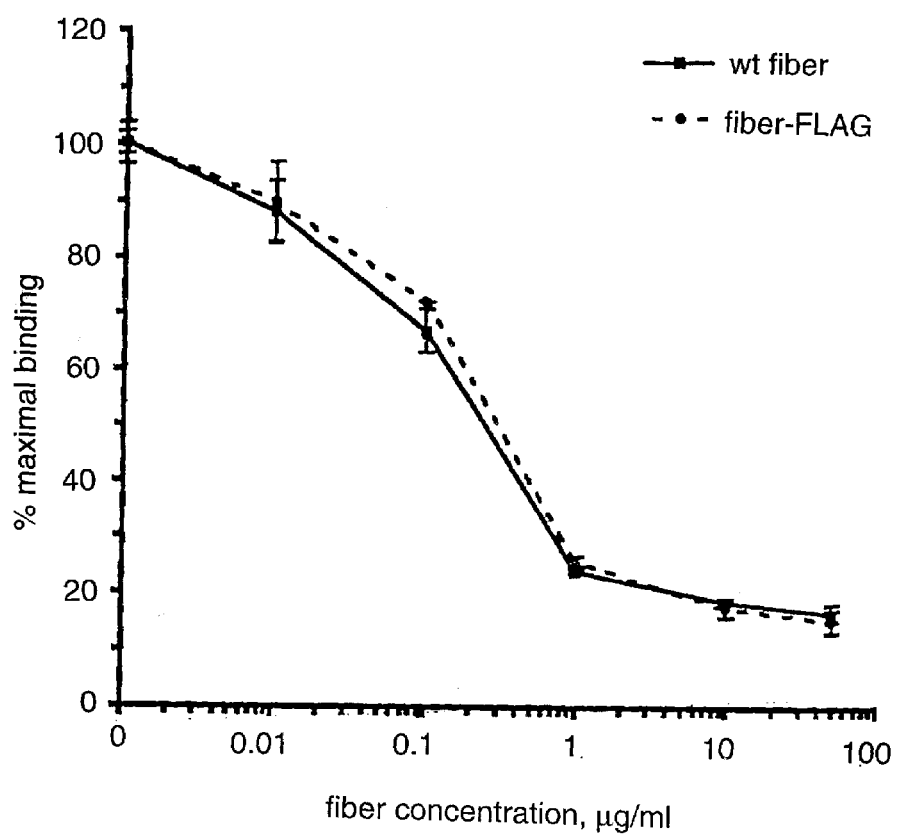

In order to prove this, radiolabeled Ad5F$_{HI}$FLAG was employed to investigate its ability to bind the fiber receptors on the cell surface. In this assay $^{125}$I-labeled Ad5F$_{HI}$FLAG was allowed to bind A549 human lung carcinoma cells, which are known to express high levels of AdS fiber receptors. Baculovirus expressed wild type AdS fiber and fiber-FLAG were used as competitors to selectively block cellular receptors and inhibit virus binding. The recombinant adenovirus vector Ad5CMVLacZ containing wild type fibers was used as a control. FIGS. 6A and 6B clearly show that, as expected, both viruses demonstrate identical dose responses when competing with fibers of either type. Thus, incorporation of the heterologous peptide in the HI loop of the fiber-FLAG protein did not have any negative effect on the formation of the cell binding site localized in the knob and, therefore, did not affect virus infectivity.

EXAMPLE 20

FLAG Accessibility in the Context of the Ad5F$_{HI}$FLAG Virion

As the insertion of a targeting ligand into the knob was desired, it was necessary to determine whether such a ligand would be available for interaction with its target cell surface receptor after incorporation into the adenovirus virion. To this end, the FLAG sequence incorporated into the fiber of Ad5F$_{HI}$FLAG was employed to test the accessibility of the HI loop of the knob in the context of an intact adenovirus particle. This was accomplished in an assay similar to the one used to evaluate FLAG accessibility in the recombinant fiber-FLAG protein expressed in insect cells.

Figure 7:
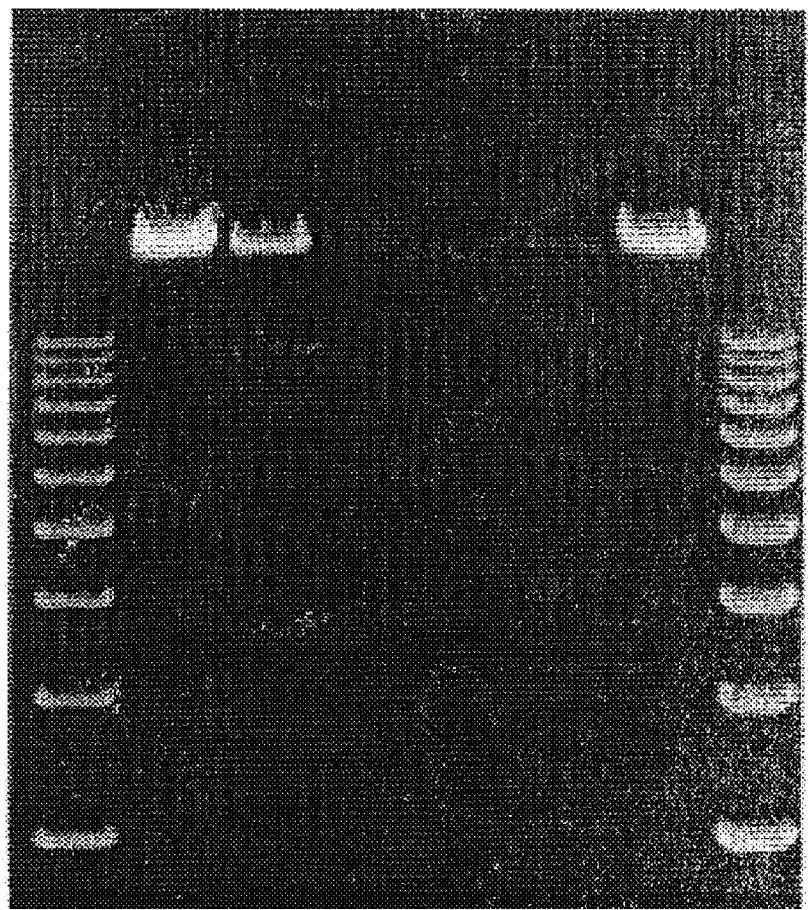
FIG. 7 shows the accessibility of the FLAG peptide in the context of intact Ad5F$_{HI}$FLAG virions. Virions of Ad5F$_{HI}$FLAG purified on a CsCl gradient were dialyzed, immunoprecipitated with anti-FLAG M2-affinity gel as described below, and eluted from the gel with free FLAG peptide. Recombinant adenovirus vector Ad5CMVLuc containing unmodified fiber was used as a negative control for binding. Aliquots of all the fractions collected throughout the purification procedure were treated with DNase I to digest traces of the cellular DNA and then treated with SDS, EDTA, and proteinase K to release adenovirus DNA from the virions. The samples obtained were analyzed on a 0.8% agarose gel, and DNA was detected by ethidium bromide staining. Lanes 1 through 3, AdCMVLuc in the supernatant containing unbound material, buffer wash, and FLAG-eluate, respectively; lanes 4 through 6, Ad5F$_{HI}$FLAG in the supernatant, buffer wash, and FLAG-eluate, respectively. Lane M, DNA molecular weight standards (the bands corresponding to marker fragments ranging from 3 to 12 kb are seen on the gel).
Figure 8A:
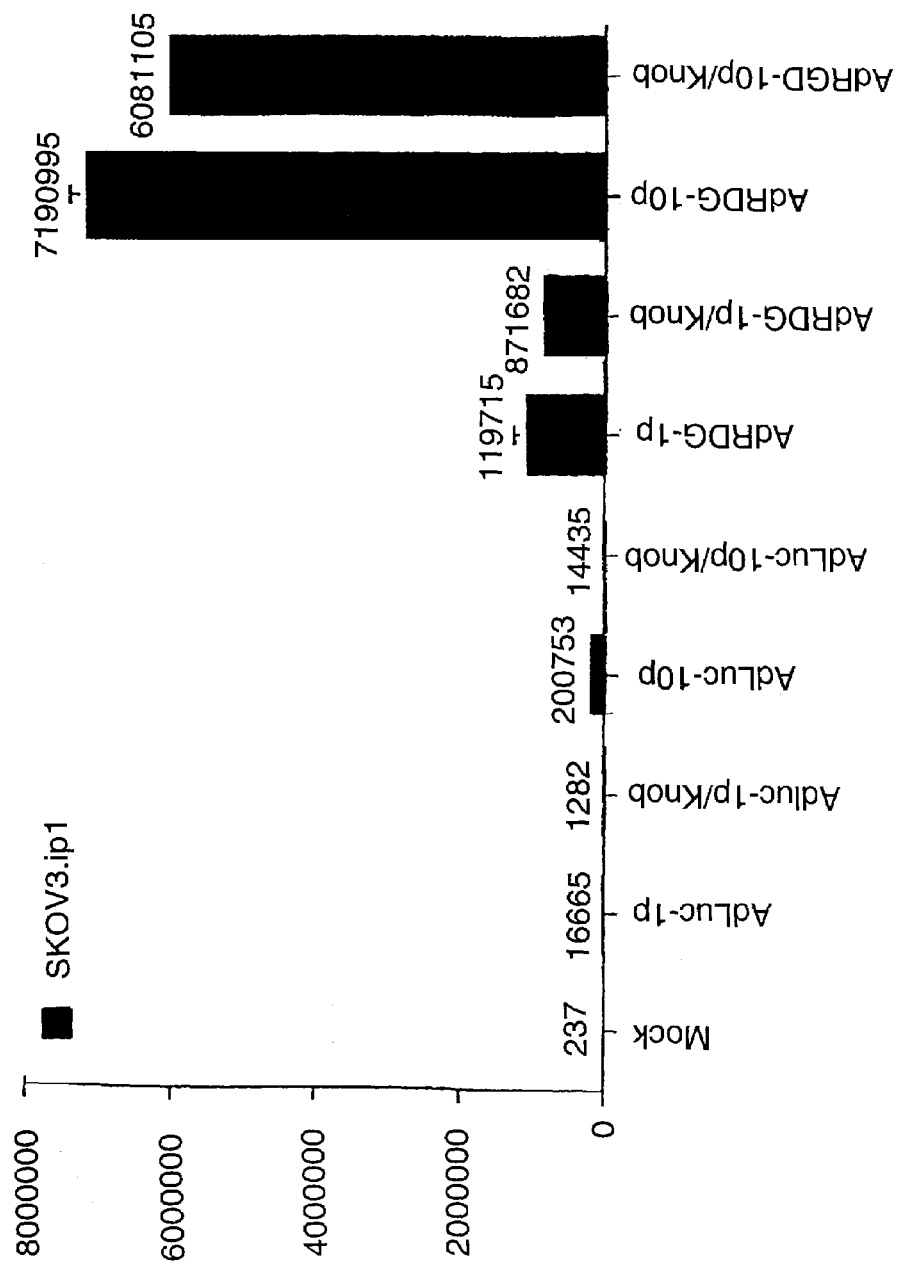
FIG. 8(A-D) shows the ability of genetically modified adenovirus, which contains the targeting epitope RGD in the HI loop of the knob, to infect two human ovarian cell lines (SKOV3.ip1 and OV-4) and two primary human ovarian cancer cell lines and the results of the inhibition of transduction by the presence of recombinant knob protein. Each point represents the mean of four determinations obtained in one experiment. Error bars show standard deviations.
Figure 8B:
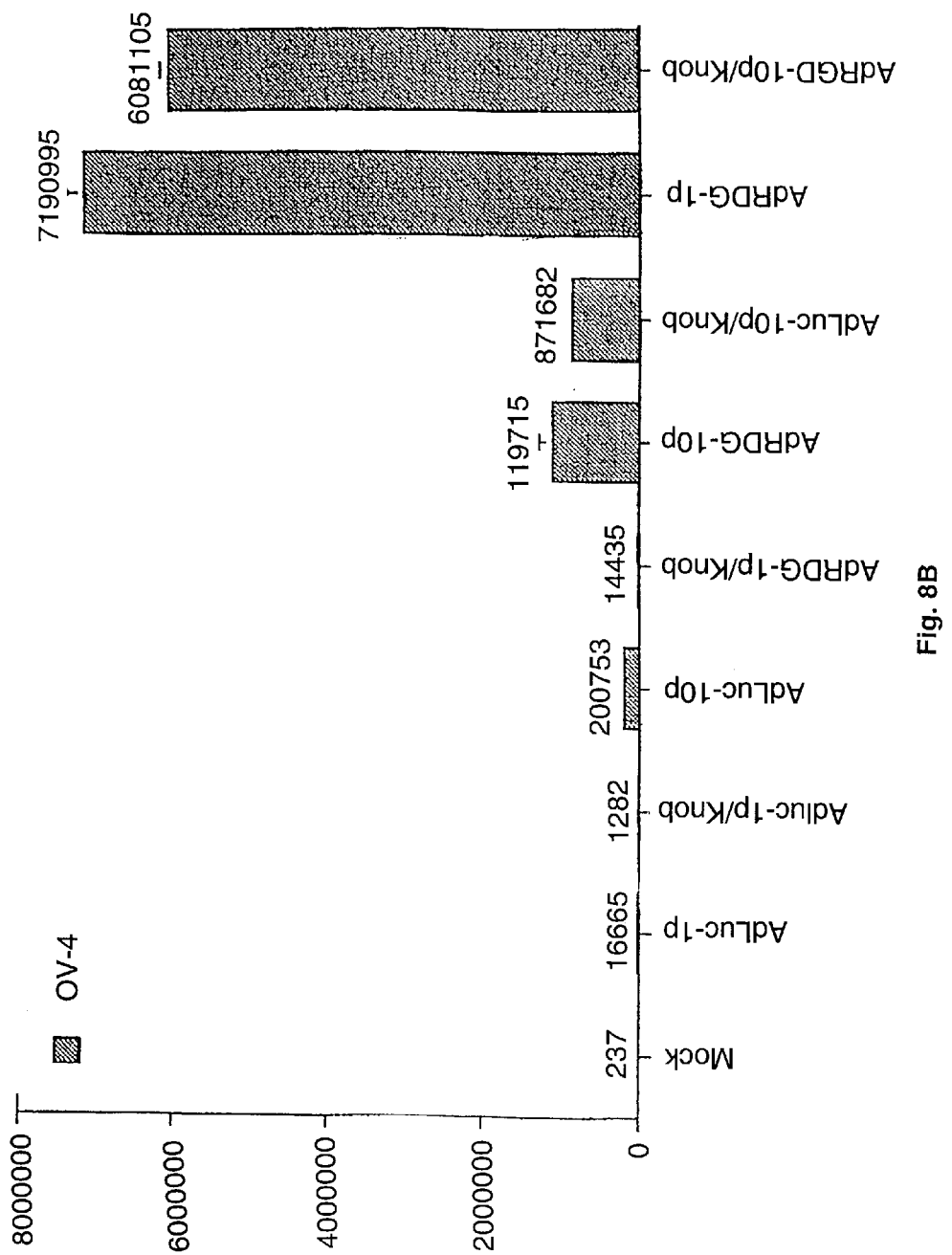
Figure 8C:
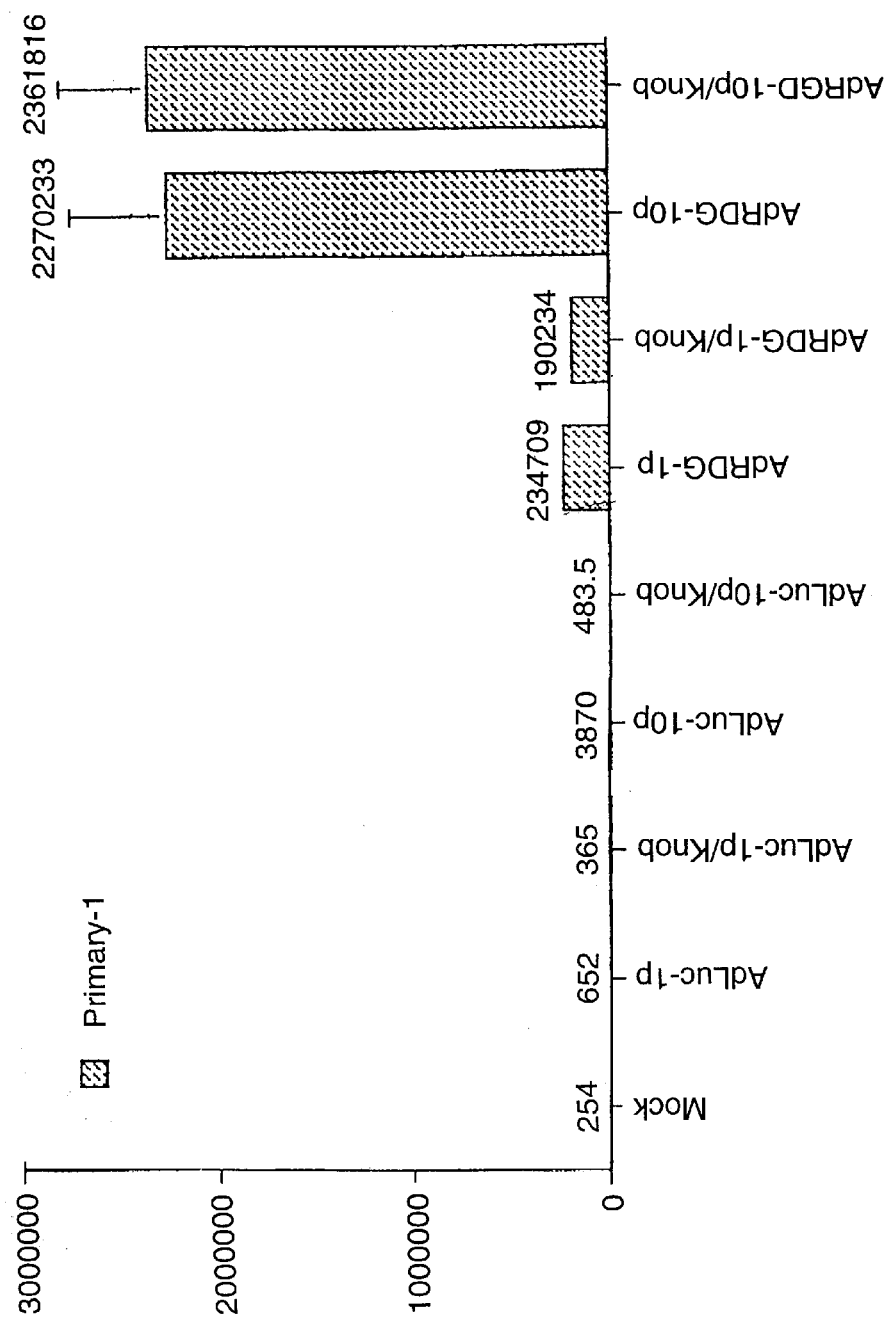
Figure 8D:
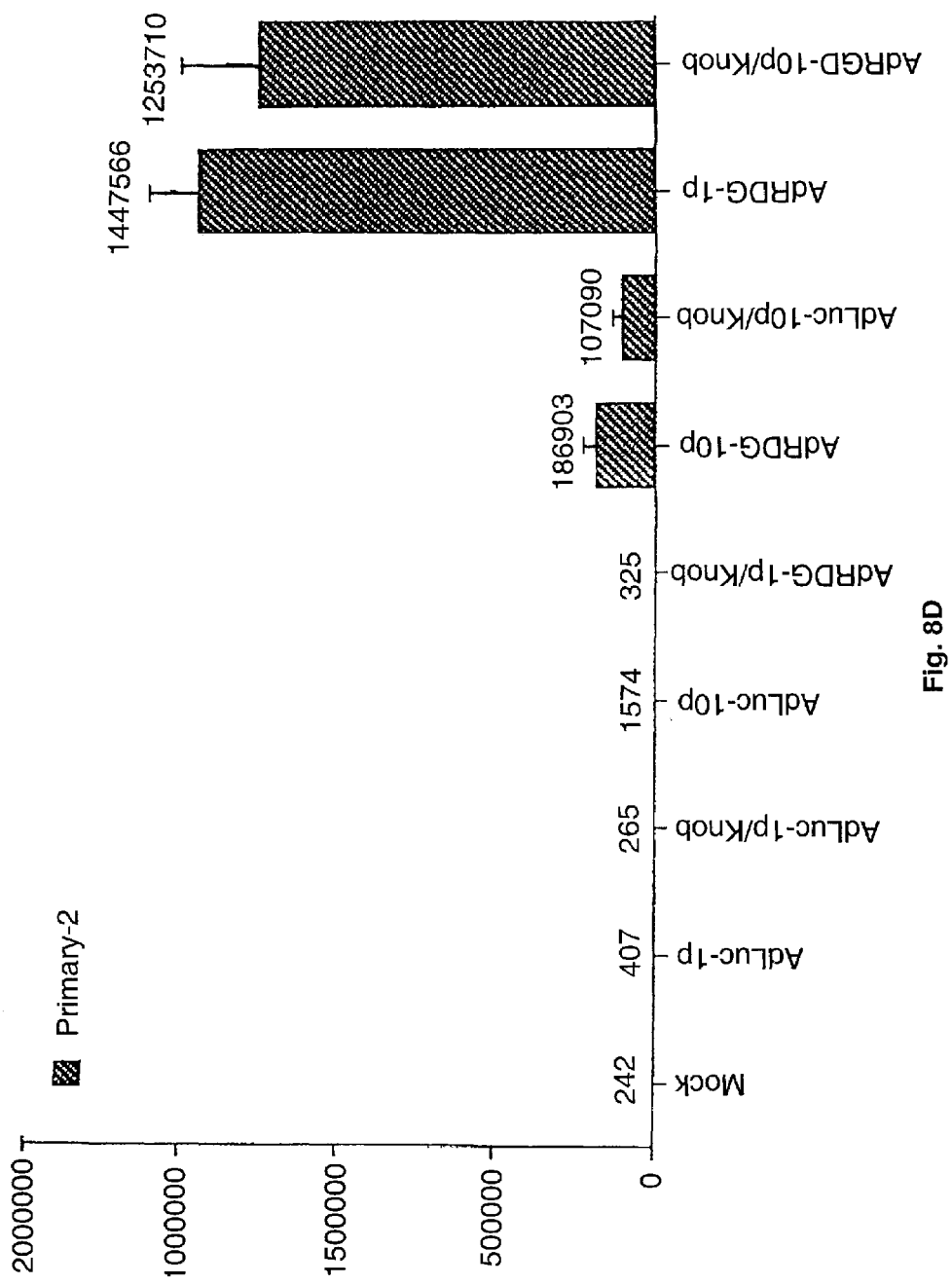

Virions purified on a CsCl gradient were dialyzed against HEPES buffer and incubated with M2-affinity gel to allow interaction between the FLAG peptide and an anti-FLAG monoclonal antibody conjugated to the gel matrix. Similarly prepared virions of AdCMVLuc containing wild-type fibers were utilized in this experiment as a negative control. After incubation, the buffer containing unbound material was collected and the gel was washed with the buffer to remove the traces of free virus. Finally, the viruses were eluted from the gel with soluble FLAG peptide. Aliquots of the samples collected were treated with proteinase K to release viral DNA from virions, which was then visualized by agarose gel electrophoresis (FIG. 7). As expected, virions of AdCMV-Luc did not react with M2 antibody and were detected only in the fraction containing unbound virus and in the wash. In marked contrast, Ad5F$_{HI}$FLAG particles efficiently bound to the M2-affinity gel, since viral DNA was present primarily in the FLAG peptide eluate. Thus, these findings have established that the heterologous ligand sequence engineered into the HI loop of the knob domain of the fiber incorporated in the intact Ad5 virion remains accessible for interaction with the relevant receptor structure, thereby providing the rationale for the generation of genetically targeted adenovirus vectors on this basis.

EXAMPLE 21

Transduction Efficiencies of Recombinant-Fiber-Protein Adenoviruses

The cell lines used were plated into 12-well tissue culture plates at a density of $2 \times 10^5$ cells/well in complete media with appropriate control. The seeded cells were allowed to attach overnight at 37° C. On day 2, the cells were washed once with 1×PBS and preincubated with 250 µl of PBS (control) or 250 µl of recombinant AdS knob (100 µg/ml) in 1×PBS for 10 minutes at room temperature. The cells were then infected by AdSCMVLuc or Ad5LucRGD at two multiplicities of infection: 1 PFU/cell or 10 PFU/cell (250 μl/well in DMEM/F12 with 4% FBS), respectively. After 30 minutes incubation at 37° C., the knob solution and infectious medium were removed from each well. The wells were washed once with 1×PBS, then 1 ml of fresh complete medium was added to each well. The cells were cultured for 48 hours when the luciferase assay was performed.

The two primary cells were thawed an aliquoted into 15 ml centrifuge tubes. PBS was, knob treatment and viral infection procedures were carried out in suspension. After infection cell suspensions were centrifuged, medium was aspirated and the cells were resuspended in complete medium, plated into the wells of 12 well plates an incubate at 37° C. for 48 hours. For the luciferase activity assay, lysates of Ad-transduced cells were prepared and luciferase assay was done according to recommendations for Promega's "Luciferase Assay System".

Despite numerous attempts to improve adenovirus as a vector for gene therapy applications, it still suffers from a number of important disadvantages, one of them being the promiscuous tropism of this virus. Genetic modification of adenovirus coat proteins to target novel cell surface receptors is the most radical and, if successful, potentially the most efficient way to overcome this limitation. In this regard, fiber, penton base, and hexon proteins are candidates for such genetic modifications. While modifications of the penton base (42, 46) and the hexon (8, 11) have been reported, these alterations were limited to the introduction of short peptide sequences into the exterior domains of these components of the adenovirus virion. In contrast, a larger number of studies have attempted functional modifications of the fiber protein. These attempts to modify the fiber protein have an obvious explanation: in contrast to the hexon and penton base proteins, the fiber protein mediates the primary interaction of the virus with its cognate cellular receptor and therefore dictates the tropism of the virus. In addition, due to its rod-like structure, the fiber can optimally expose a novel binding ligand engineered into its structure, thus providing efficient binding to an alternative cellular receptor. Thus, alterations to the carboxy-terminal knob domain of the fiber normally containing the cell binding site is a logical approach to modifying viral tropism.

Since the time this idea was originally employed (31), several groups of investigators have proved its utility. To this end, recombinant adenoviruses containing chimeric Ad5-Ad3 (25, 37) fiber were derived, demonstrating the possibility of creating functional fiber chimeras. In addition, it was shown that by replacing the knob domain of the fiber one can alter the receptor specificity of the virus. Furthermore, Wickham et al. (45) showed that addition of a carboxy-terminal polylysine sequence to the fiber polypeptide resulted in expanded tropism of the adenovirus vector. Recently, recombinant adenoviruses with fibers containing carboxy-terminal gastrin releasing peptide (30a), somatostatin, E-selectin binding peptide, and six-His sequence (24a) have been generated. However, none of these efforts related to ablating the native tropism of the adenovirus vector; in these approaches, novel tropism distinct from the pre-existing natural tropism of the vector was engineered.

Until recently, the ability to accomplish the practical design of retargeted adenovirus vectors was limited by two major problems: lack of knowledge of the structure of the fiber knob domain and difficulty in manipulating the fiber gene in the context of the adenovirus genome. In this regard, publication of the 3D model of the Ad5 fiber knob by Xia et al. (47, 48) and the development of a genetic method by Chartier et al. (7), which allow modification of virtually any region of the adenovirus genome, facilitates efforts to retarget the adenovirus via alterations to the knob domain of the fiber. The present study is a unique attempt to generate recombinant adenovirus genomes and derive adenovirus vectors with modified fibers containing novel peptide ligands.

The methods of the present invention describe the utilization of the HI loop of the fiber knob as a site for incorporation of heterologous peptide sequences. According to the 3D model of the Ad5 fiber knob, the HI loop does not contribute to interactions within the knob which stabilize its trimeric configuration and is not involved in the formation of the receptor binding site. Importantly, due to the prevalence of hydrophilic amino acid residues in its primary sequence, the HI loop is exposed outside the knob, thereby facilitating the interaction of potential ligand with the cellular receptor.

For proof of the concept, a FLAG coding sequence was incorporated into the region of the fiber gene corresponding to the HI loop and this modified gene was expressed in baculovirus infected insect cells. An amino terminal six-His tag incorporated into the design was used for simple chromatographic purification of recombinant fiber protein. Baculovirus-directed expression of this recombinant full size fiber was efficient, and according to the gel analysis and ELISA with the trimer-specific anti-fiber monoclonal antibody, the product of expression was trimeric.

To further characterize the fiber-FLAG protein produced in insect cells, the accessibility of FLAG in the context of the fiber trimer was demonstrated. An assay based on the specific interaction of FLAG-tagged proteins with M2-affinity gel containing anti-FLAG monoclonal antibody was employed. This analysis confirmed that the FLAG peptide was localized on the surface of the trimeric knob and was available for binding, thereby supporting the hypothesis about surface localization of the HI loop. By employing the fiber-FLAG chimera to block adenovirus infection it was also shown that insertion of the FLAG peptide into the HI loop of the knob does not affect the correct folding of the cell binding domain localized in the knob. This is a significant finding considering that the HI loop connects β-strands H and I, which are hypothesized to be involved in binding to the cellular receptor (47, 48).

To incorporate fiber-FLAG chimeras into the adenovirus virion, a recombinant adenovirus genome was generated by using a method described recently (7). To reach this end, a master plasmid, pTG3602, obtained from Transgene was modified to engineer a vector which greatly facilitates modifications of the fiber gene in the adenovirus genome. By using this plasmid, recombinant genome was generated and the virus of interest, Ad5F$_{HI}$FLAG was rescued. Importantly, this new virus was produced in high yields and demonstrated dynamics of infection identical to those of the wild type Ad5. Successful rescue of Ad5F$_{HI}$FLAG, as well as subsequent characterization of the virion, confirmed the conclusions based on the results obtained with fiber-FLAG protein expressed in baculovirus-infected insect cells, thereby making baculovirus an expression system of choice for further fiber-modeling experiments.

For further proof of the concept, a RGD peptide (CDCRGDCFC (SEQ ID No. 16)) coding sequence was incorporated into the region of the fiber gene within the HI loop and replacing the amino acids TLNGTQETGDTTP (SEQ ID No. 17). The RGD peptide has an affinity for integrins. To incorporate fiber-RGD chimeras into the adenovirus virion, a recombinant adenovirus genome was generated by using a method described recently (7). The RGD peptide is a known ligand of intigrins of various types including α$_v$β5 and α$_v$β3

(Ruoslahti, E. 1996 RGD and other recognition sequences for integrins, Annu. Rev. Cell. Dev. Biol. 12: 697-715). Adenovirus containing the RGD peptide within the HI loop were tested for their ability to infect ovarian cancer cell lines and primary ovarian cancer cells. The adenovirus containing the RGD peptide were found to infect both the ovarian cell lines and the primary ovarian cancer cells something wild-type adenovirus is unable to do. Furthermore, adenovirus containing the RGD peptide within the HI loop were tested for their ability to infect 293 cells. The modified adenovirus was not able to infect these cells while wildtype adenovirus was infected. Thus, the insertion and replacement of the HI loop both introduced novel tropism and ablated wildtype tropism.

The present invention demonstrates that the HI loop of the fiber knob is a convenient site for incorporation of heterologous peptide ligands which may be successfully utilized in order to target adenovirus vectors for gene therapy applications. This location in the knob can be used either as an alternative site or in addition to carboxy-terminal modifications of the fiber protein, offering a unique loop-like environment, which may be required for proper biological functioning of some ligand sequences. For example, this structure may be beneficial for peptide ligands obtained from phage display libraries containing random peptide sequences flanked with two cysteine residues forming a disulfide bridge (23, 24). In addition, ligands with the loop-like configuration may be less susceptible to degradation by cellular carboxypeptidases than ligands positioned at the carboxy terminus of the fiber. To realize the full potential of the HI loop for ligand incorporation, one can make recombinant adenoviruses containing different targeting moieties in this locale. Generation of recombinant adenoviruses containing fibers with targeting ligands incorporated into the HI loop of the knob will facilitate efforts towards an improved adenovirus vector for gene therapy applications. Although the development of novel methods for the purification of adenoviruses was not the focus, successful use of the FLAG epitope in binding experiments suggests that this or a similar purification tag can be incorporated into an adenovirus virion to facilitate its purification. This simple purification technique does not require expensive laboratory equipment such as ultracentrifuges or high pressure liquid chromatography systems and can be easily scaled up if needed.

EXAMPLE 22

Adenovirus-Mediated Gene Transfer Assay

Adenovirus-mediated transduction experiments utilizing cell lines were done as described above. Primary cells from ascites obtained from ovarian cancer patients were prepared for this analysis as follows. First, the erythrocytes present in the samples were lysed by addition of buffer containing 150 mM $NH_4Cl$, 1 mM $KHCO_3$ and 0.1 mM $Na_2EDTA$. Then, the cell debris and dead cells were separated from the live cells by slow-speed centrifugation on a step gradient of Ficoll-Hypaque (Media Preparation Shared Facility, UAB Comprehensive Cancer Center, Birmingham, Ala.). The cells were washed twice with Dulbecco's Modified Eagle's Medium/F12 (DMEM/F12) (Cellgro, Herndon. Va.) containing 10% fetal bovine serum (FBS) (Hyclone Laboratories, Logan, Utah), 100 units/ml penicillin and 100 μg/ml streptomycin. Binding of $^{125}I$-labeled adenovirus to 293, HUVEC or RD cells was assayed.

EXAMPLE 23

Fiber-RGD Protein Efficiently Interacts with Integrins Via RCD Tripeptide

As demonstrated above, FLAG octapeptide incorporated in the HI loop of Ad5 fiber does not interfere with correct folding of the cell-binding site localized in the knob and is available for binding to FLAG-specific antibody in immunoprecipitation assay. To utilize these findings for the purposes of adenovirus retargeting, a RGD-4C peptide, CDCRGDCFC (SEQ ID No. 16), known to bind with high affinities to several types of integrins present on the surface of mammalian cells was introduced in the HI loop of the fiber knob. This effort was undertaken in an attempt to generate an adenoviral vector, which would be able to bind to cells by utilizing fiber-RGD/integrin interaction. Therefore, the infection by such virus would not be dependent on the presence of CAR receptor on a cell membrane.

For this, the RGD-4C containing fiber protein, fiber-RGD, was expressed in a baculovirus expression system in order to characterize the protein with respect to its ability to perform the targeting functions. The sequence encoding the amino terminal six-His tag was incorporated in the fiber-RGD gene in order to facilitate downstream purification of the product.

Figure 9:
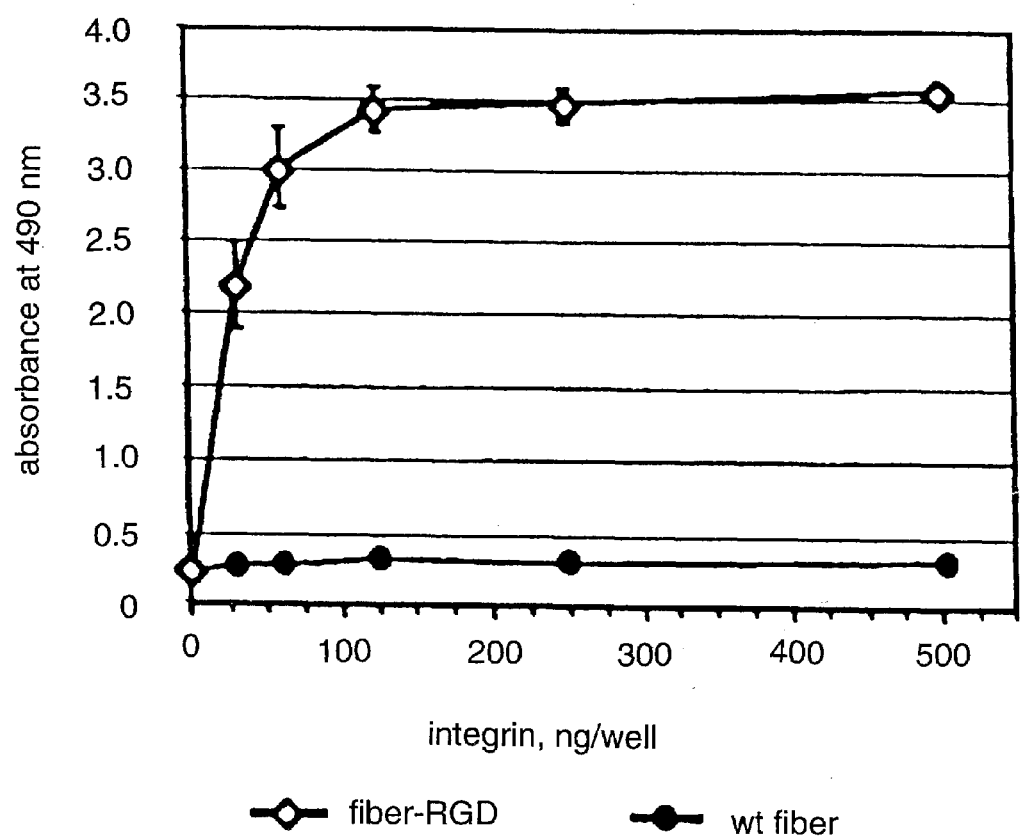
FIG. 9 shows an analysis of interaction between recombinant fiber proteins and $\alpha_v\beta_3$ integrin. Baculovirus expressed fiber proteins absorbed on an ELISA plate were incubated with various concentrations of purified integrin $\alpha_v\beta_3$. Integrin bound to fiber proteins was then detected with anti-α-subunit monoclonal antibody VNR139. Each point represents a mean of three readings obtained in one experiment. Some SDs are smaller than symbols.

Electrophoresis of IMAC-purified fiber-RGD protein showed that the fiber retains its native trimeric structure (data not shown), which is known to be crucial for association of the fiber with the penton base during virion assembly. In order to assess the ability of the fiber-RGD to bind to integrins, this fiber protein was employed for an ELISA assay utilizing purified integrin $\alpha_v\beta_3$. This assay showed that, in contrast to the wild type fiber protein used as a negative control, the fiber-RGD binds $\alpha_v\beta_3$ integrin very efficiently (FIG. 9). Therefore, these experiments confirmed the functional utility of the modified fiber and provided a rationale for generation of recombinant adenovirus containing such fibers.

The virus was derived by the method described by Chartier et al. To simplify the downstream gene transfer assays, an expression cassette containing the firefly luciferase gene driven by cytomegalovirus promoter was introduced in place of E1 region of the adenoviral genome. The genome of the new virus designated Ad5lucRGD was generated in E. coli via a two step protocol utilizing homologous DNA recombination between the plasmid pVK50 and fragments of DNA isolated from two shuttle vectors, PNEB. PK.F$_{HI}$RGD and pACCMV.LucΔPC, which contain the fiber gene and the luciferase expression cassette flanked with adenoviral DNA sequences, respectively.

Utilization of this method requires the digestion of the resultant recombinant plasmid containing the newly generated adenoviral genome with restriction endonuclease PacI to release inverted terminal repeats (ITR) of Ad5 DNA from the plasmid backbone. In order to be able to use the firefly luciferase gene, which contains an internal Pacd site, in the context of this method, this site was eliminated by introducing into the gene a silent mutation. The plasmid obtained as a result of aforementioned DNA recombinations, pVK703, was then utilized for transfection of 293 cells to rescue Ad5lucRGD. The identity of the virus was confirmed by PCR as well as by cycle sequencing of viral DNA isolated from CsCl-purified virions of Ad5lucRGD.

Figure 10:
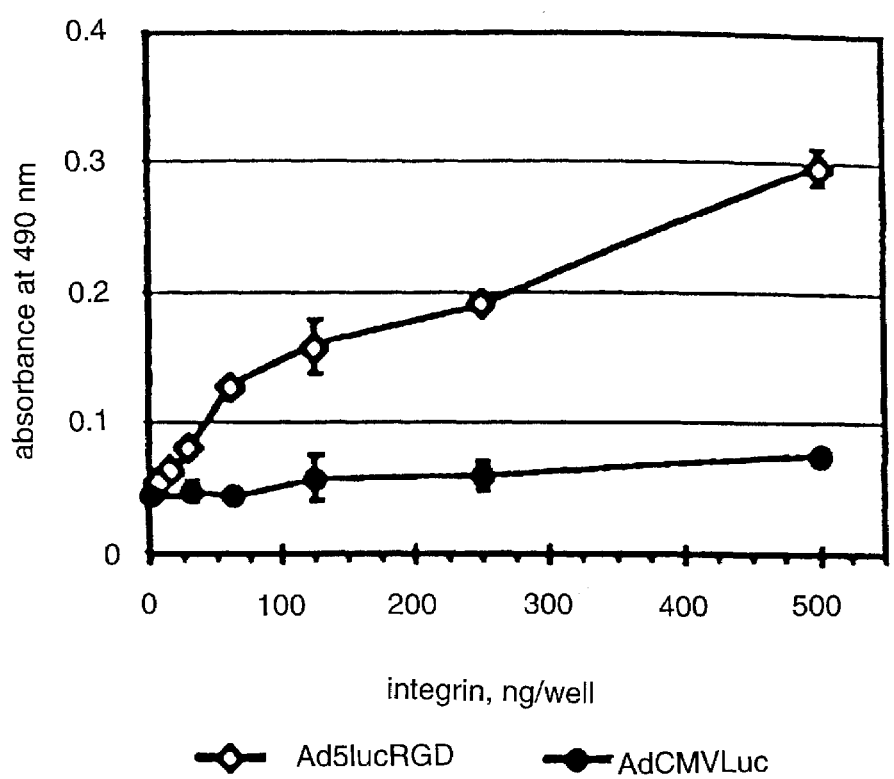
FIG. 10 shows an ELISA assay of $\alpha_v\beta_3$ integrin binding to immobilized Ad5CMVluc and Ad5lucRGD virions. CsCl purified virions of Ad5CMVluc and Ad5lucRGD immobilized in the wells of an ELISA plate were incubated with affinity purified $\alpha_v\beta_3$ integrin, followed by incubation with monoclonal antibody VNR139. Data shown are means±SD from an experiment performed in triplicate.

To demonstrate the accessibility of the RGD tripeptide incorporated in the fiber of Ad5lucRGD, this virus was utilized for an ELISA assay analogous to the one used previously for purified fiber protein. This analysis clearly showed efficient binding of the $\alpha_v\beta_3$ integrin to immobilized particles of Ad5lucRGD, while binding of $\alpha_v\beta_3$ to a control virus was at the background level at all concentrations of integrin used (FIG. 10). Based on these results, it appears that Ad5lucRGD is able to interact in vitro and in vivo with various types of RGD-binding integrins, thereby utilizing this interaction at early steps of infection in order to attach to target cells.

EXAMPLE 24

Ad5lucRGD is Capable of Mediating a CAR-Independent Gene Delivery

Next, whether introduction of the RGD-motif in the fiber of Ad5lucRGD resulted in any changes with respect to this virus ability to infect cells was examined. In order to investigate the infection pathway utilized by Ad5lucRGD, this virus was employed for gene transfer to several cell lines, expressing various levels of CAR as well as integrins $\alpha_v\beta_3$ and $\alpha_v\beta_3$. For this, a panel of the cell lines including the 293 human kidney cells, human umbilical cord endothelial cells, HUVEC, and human embryonal rhabdomyosarcoma cells, RD, was employed for a series of flow-cytometry assays. While 293 cells readily support adenovirus infection, HUVECs bind adenovirus poorly, whereas CAR expression in RD cells is passage-dependent.

Figure 11D:
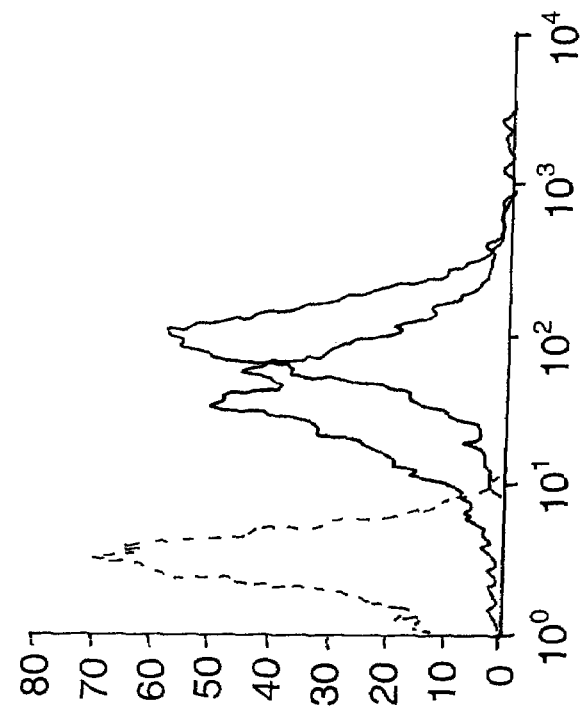
FIG. 11 shows a flow cytometric analysis of CAR and integrins expression in 293, HUVEC and RD cells. Cells were incubated with anti-CAR (RmcB), anti-$\alpha_v\beta_3$ (LM609) or anti-$\alpha_v\beta_5$ (P1F6) integrin monoclonal antibodies, washed with SM to remove unbound monoclonals and incubated with secondary FITC-labeled goat anti-mouse IgG serum. After removal of the FITS-labeled antibodies, aliquots of $10^4$ cells were analyzed by flow cytometry. CAR expression in 293 (11A), HUVEC (11C) and RD (11E) cells. Expression of $\alpha_v\beta_3$ (thin line) and $\alpha_v\beta_5$ (heavy line) integrins in 293 (11B), HUVEC (11D) and RD (11F) cells. Dotted line shows negative control.
Figure 11C:
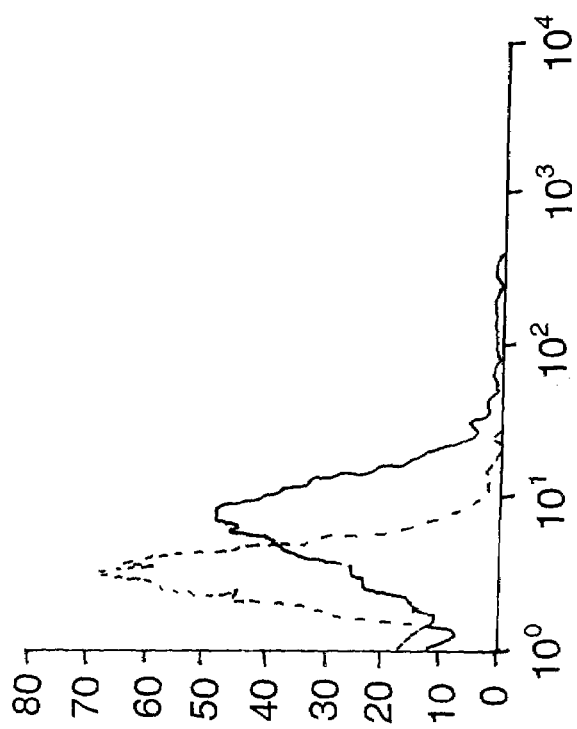
Figure 11F:
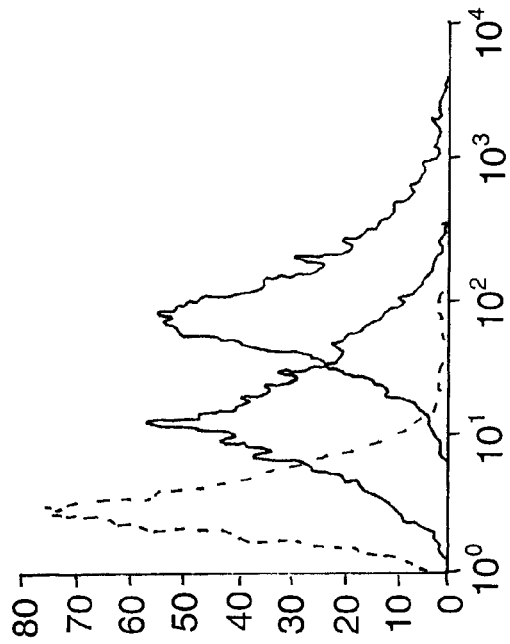
Figure 11E:
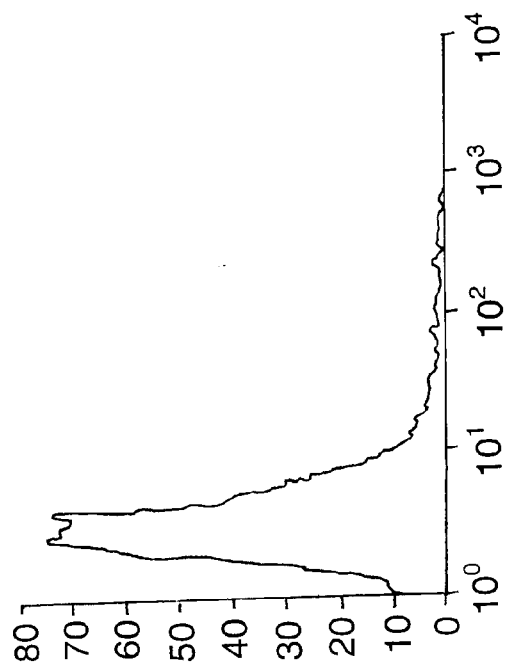

The flow cytometry assay showed that 293 cells express high levels of CAR (FIG. 11A) and $\alpha_v\beta_3$ integrin, while expression of $\alpha_v\beta_3$ is moderate (FIG. 11B). HUVECs demonstrated moderate levels of CAR expression (FIG. 11C), whereas both integrins were present at the cell surface in rather high amounts (FIG. 11D). Rhabdomyosarcoma cells RD were CAR-negative (FIG. 11E), while being high $\alpha_v\beta_3$ and moderate $\alpha_v\beta_3$ expressors (FIG. 11F). Therefore, for the subsequent gene transfer experiments, a set of cell lines covering a full range of CAR expression profiles was established, while having moderate-to-high levels of integrins $\alpha_v\beta_3$ and $\alpha_v\beta_3$ present on their cytoplasmic membranes. Ad5lucRGD was then utilized for an assay based on competitive inhibition of adenovirus-mediated gene delivery by recombinant Ad5 fiber knob protein, known to efficiently block virus binding to CAR receptor.

Figure 12A:
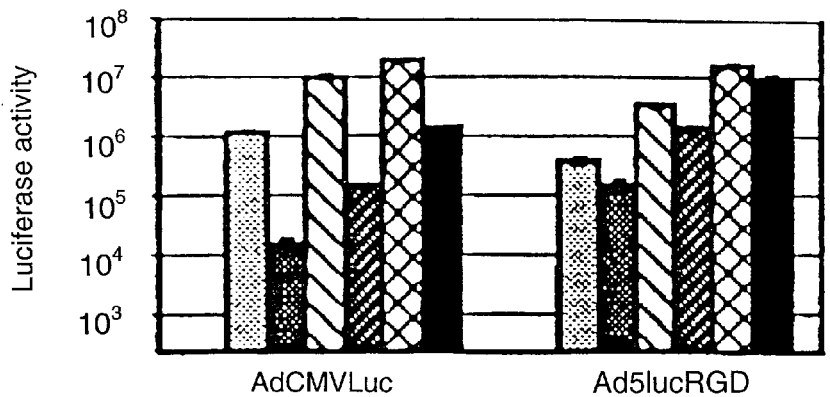
FIG. 12 shows adenovirus-mediated gene transfer to various human cell lines. 293 (12A), HVEC (12B) or RD (12C) cells preincubated for 10 min at room temperature in either DMEM/F12 or DMEM/F12 containing recombinant Ad5 fiber knob at 100 µg/ml were then exposed for 30 min at room temperature to AdCMVLuc or Ad5lucRGD in DMEM/F12 at 1, 10 or 100 pfu/cell. The unbound virus was aspirated and complete medium was added. After incubation at 37° C. for 30 hours, the cells were lysed and the luciferase activity in relative light units (RLU) was determined. Background luciferase activities detected in mock infected cells were 261, 223 and 163 rlu for 293, HUVEC and RD cells, respectively. These activities were subtracted from all readings obtained with the corresponding cell line. Each point represents the mean of three determinations±SD.

As shown in FIG. 12A, luciferase expression in 293 cells mediated by the control virus, AdCMVLuc, was efficiently blocked by recombinant knob protein. Depending on the multiplicity of infection (MOI) used, knob protein blocked 85% to 93% of luciferase activity in AdCMVLuc-transduced cells.

In marked contrast, the same concentration of knob was able to block only 40% to 60% of Ad5lucRGD-mediated gene expression in 293 cells, thereby indicating that in addition to well characterized fiber-CAR interaction utilized by the wild type Ad5, Ad5lucRGD was capable of using an alternative, CAR-independent, cell entry pathway. Of note, the contribution of that alternative mechanism of cell binding was quite significant, providing 40% to 60% of overall gene transfer to 293 cells.

Figure 12B:
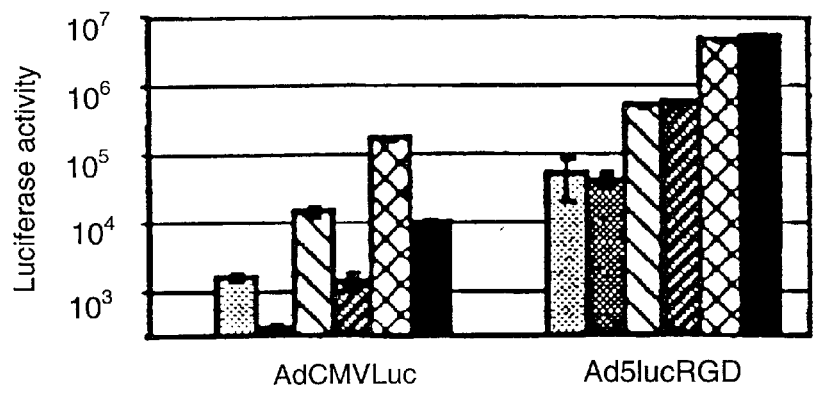

To further investigate the phenomenon of Ad5lucRGD-directed gene delivery, the same strategy was utilized to look into transduction of HUVECs. These cells are relatively difficult to transduce with adenoviral vectors containing wild type fibers. These findings were corroborated with the flow cytometry data, which showed modest levels of CAR expression in HUVECs. Importantly, rather high levels of $\alpha_v\beta_3$ and $\alpha_v\beta_3$ integrins detected in these cells suggested, that HUVECs should be readily transduced with Ad5lucRGD. Although the levels of luciferase activity in HUVEC cells mediated by either virus were considerably lower than those in 293 cells, the experiment revealed striking differences between the transduction profiles demonstrated by these two viruses (FIG. 12B). First, luciferase expression in Ad5lucRGD-transduced cells was about 30-fold higher than in the cells transduced with AdCMV-Luc. Second, the effect of Ad5 fiber knob on AdCMVluc-mediated transduction was less dramatic than in the experiments with 293 cells, consistent with a relative lack of CAR in the HuvECs. Most importantly, recombinant knob protein had no inhibition effect on the levels of luciferase expression directed by Ad5lucRGD.

Figure 12C:
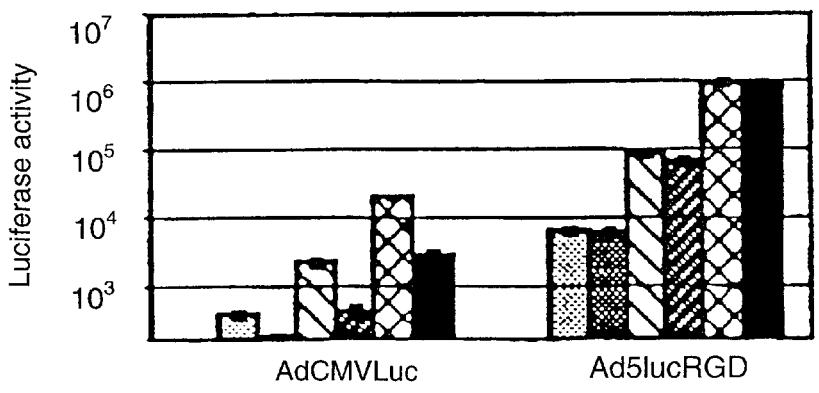

Very similar results were then generated on RD cells, which do not express CAR receptor. The luciferase activity detected in the lysates of AdCMVluc-transduced RD cells was extremely low: at MOI of one pfu/cell it was almost equal to background readings obtained in mock-infected cells (FIG. 12C). Once again, Ad5lucRGD was capable of directing the levels of transgene expression 16- to 47-fold higher than those mediated by AdCMVLuc. This expression was not responsive to inhibition by the fiber knob. These experiments clearly showed that incorporation of the RGD-4C peptide into the fiber of Ad5lucRGD resulted in dramatic changes in the initial steps of virus-to-cell interaction, presumably by creating an alternative cell attachment pathway.

EXAMPLE 25

Ad5lucRGD Demonstrates Increased Efficiencies of Cell Binding Due to Utilization of RGD/Integrin Interaction.

Having established that Ad5CMVluc and Ad5lucRGD demonstrate different efficiencies of gene delivery as well as different profiles of fiber knob-mediated inhibition of transduction, the cell binding profiles of these two viruses was compared. To address this issue, both viruses were labeled with $^{125}I$ and were employed in the virus binding assay on 293, HUVEC and RD cells. This assay was performed under conditions (4° C.) allowing the viruses to bind the cells, but preventing virus internalization.

Figure 13:
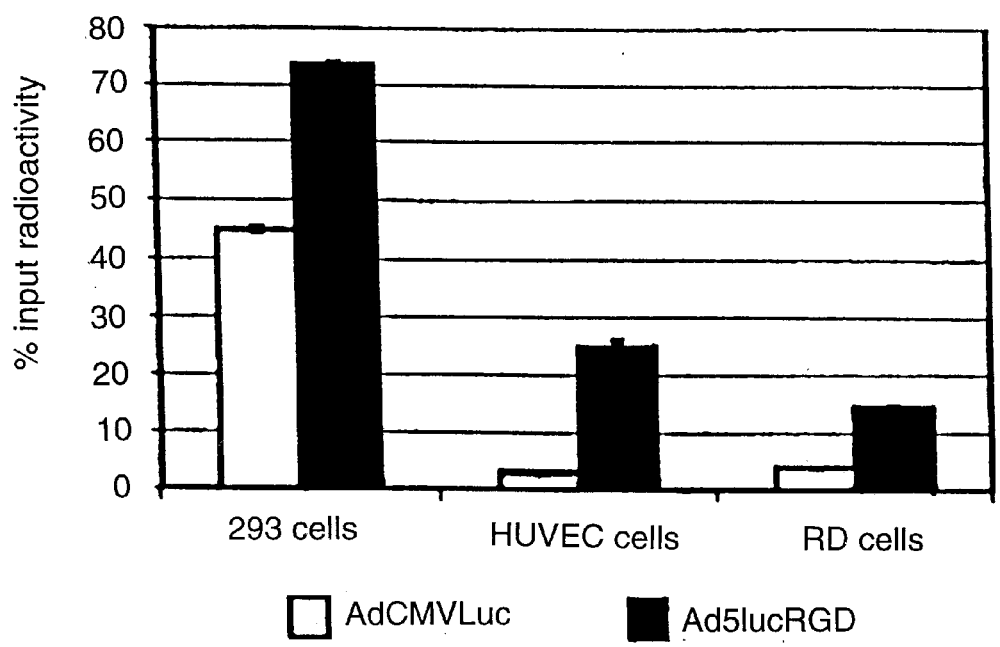
FIG. 13 shows a comparison of binding of $^{125}$I-labeled adenoviruses to 293, HUVEC or RD cells. One hundred µl aliquots of cells in DMEM-Ad medium (DMEM, 20 mM HEPES, 0.5% BSA), $10^6$ cells per aliquot, were incubated for 1 h at 4° C. with 50 µl of $^{125}$I-labeled adenovirus ($10^5$ cpm per sample). The samples were then diluted with 4 ml of PBS containing 0.1% BSA, and the cells were pelleted by centrifugation. Radioactivities of cell pellets were determined in a gamma counter. Data shown are means±SD from an experiment performed in triplicate.

As shown in FIG. 13, binding efficiencies demonstrated by Ad5lucRGD and Ad5CMVluc on CAR-positive 293 cells were similar, while the percentages of labeled Ad5lucRGD virions bound to HUVEC and RD cells were significantly higher than those of Ad5CMVluc virions. Since the goal of incorporating the RGD-containing peptide within the fiber molecule was to allow the virus to utilize cellular integrins as alternative receptors, an assay was conducted in which binding of radiolabeled viruses to the cells was accomplished in the presence of recombinant Ad2 penton base protein. Due to the presence of RGDmotif in the highly mobile loop protrusion identified within its molecule, the penton base is able to bind $\alpha_v\beta_3$ and $\alpha_v\beta_3$ integrins and therefore competes for binding to these cellular receptors with other molecules or macromolecular complexes containing an RGD-motif.

Figure 14A:
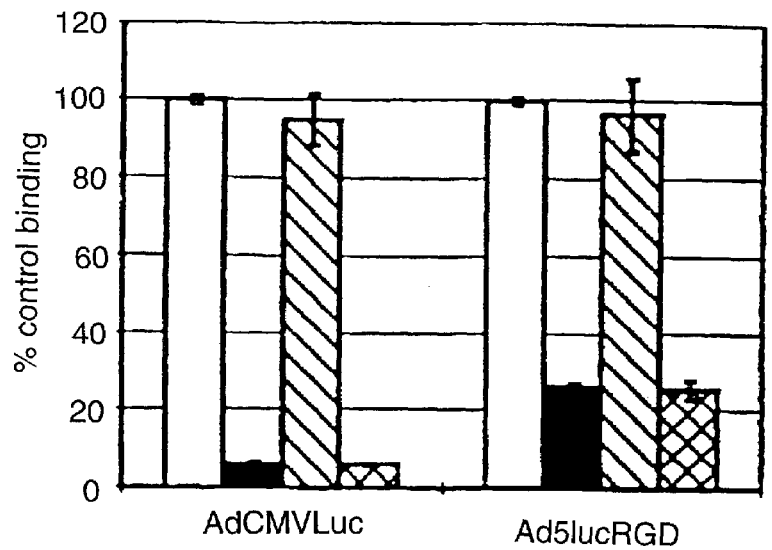
FIG. 14 shows the inhibition of binding of labeled AdCMVLuc and Ad5lucRGD to 293 and HUVEC cells. 293 (14A) or HUVEC (14B) cells were preincubated with DMEM-Ad or DMEM-Ad containing Ad5 fiber knob (100 µg/ml), Ad2 penton base (100 µg/ml) or their combination for 1 h at 4° C. Fifty µl aliquots of $^{125}$I-labeled viruses were then added to the samples. The rest of the procedure is as described in the legend for FIG. 13.
Figure 14B:
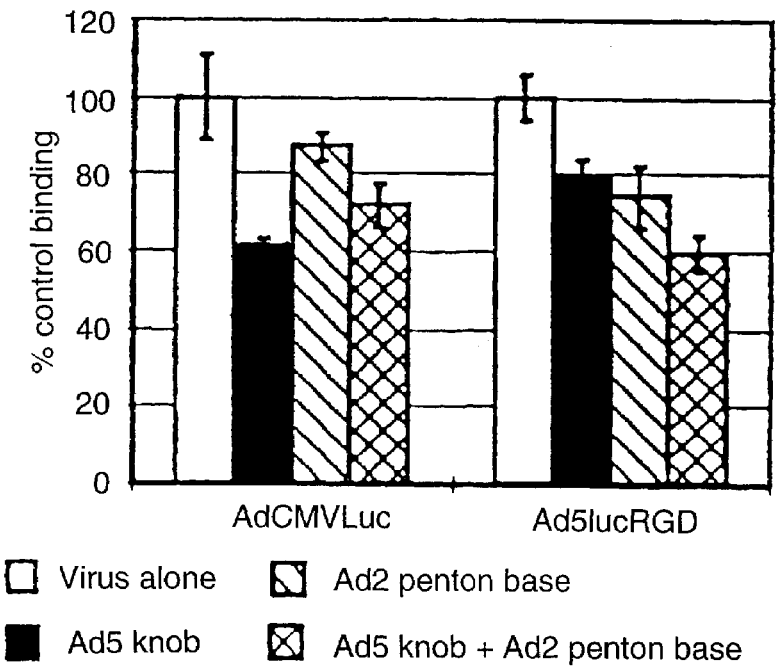

When binding of the viruses to 293 cells was assayed (FIG. 14A), the penton base protein failed to inhibit cell binding of either virus. Whereas the fiber knob protein, alone as well as together with the penton base, blocked 94% of Ad5CMVluc and 75% of Ad5lucRGD binding. The same experiment performed with HUEC cells showed that, once again, the knob protein inhibited binding of Ad5CMVluc particles to a greater extent than that of Ad5lucRGD virions (FIG. 14B). In addition, penton base was capable of decreasing Ad5lucRGD-associated radioactivity bound to these cells by 25%, while its effect on Ad5CMVluc binding was marginal. When used together, both blocking agents caused 40% decrease in Ad5lucRGD binding. Similar results were obtained when these viruses were employed for binding assay on RD cells. Although the penton base did not block binding of Ad5lucRGD to HUVEC cells as efficiently as the knob protein blocked binding of the control virus, its utilization as an integrin-specific inhibitor showed that Ad5lucRGD was capable of using cellular integrins as alternative receptors during the infection process.

EXAMPLE 26

Ad5lucRGD Mediates Enhanced Gene Transfer to Ovarian Cancer Cells

Figures 15A, 15B:
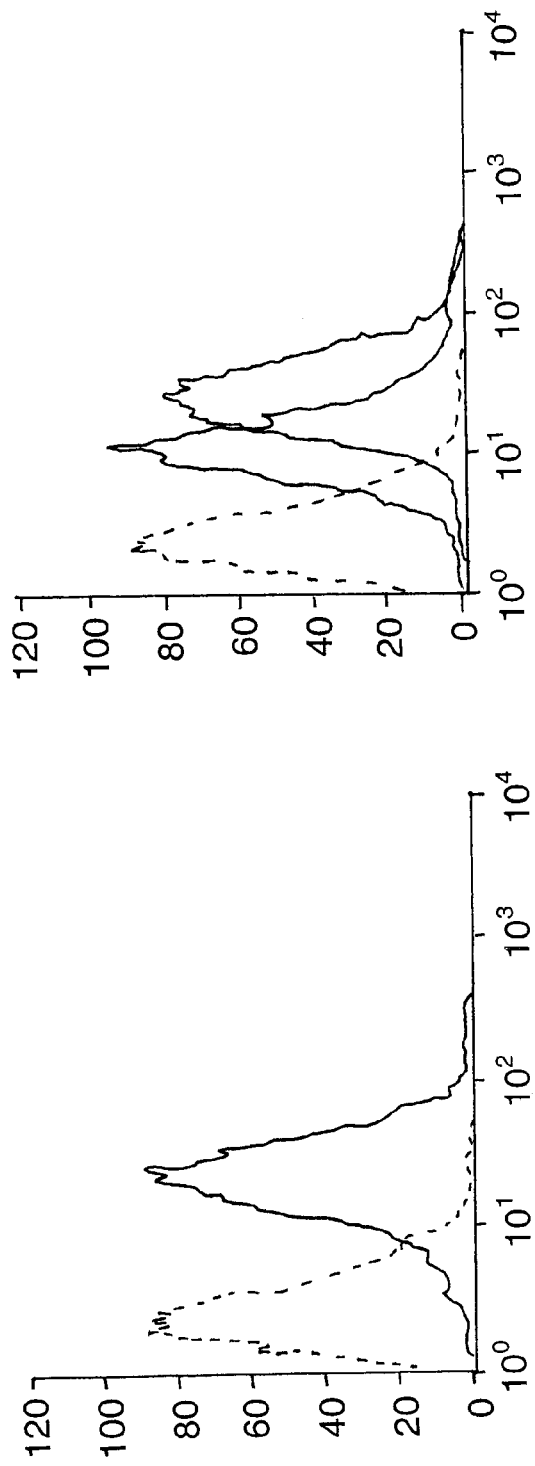
FIG. 15B and FIG. 15D show expression $\alpha_v\beta_3$ (thin line) and $\alpha_v\beta_5$ (heavy line) integrins in SKOV3.ip1 and OV-4 cells, respectively. Negative control is shown by the dotted line.
Figure 15D:
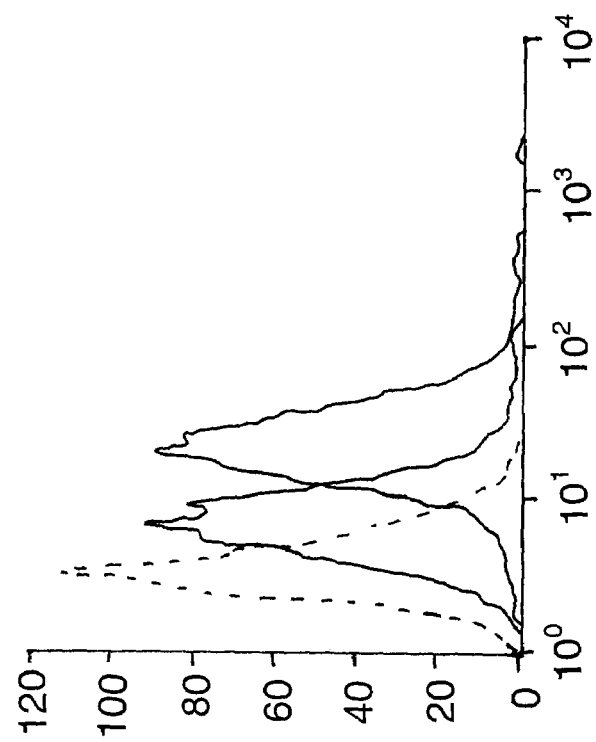
Figure 15C:
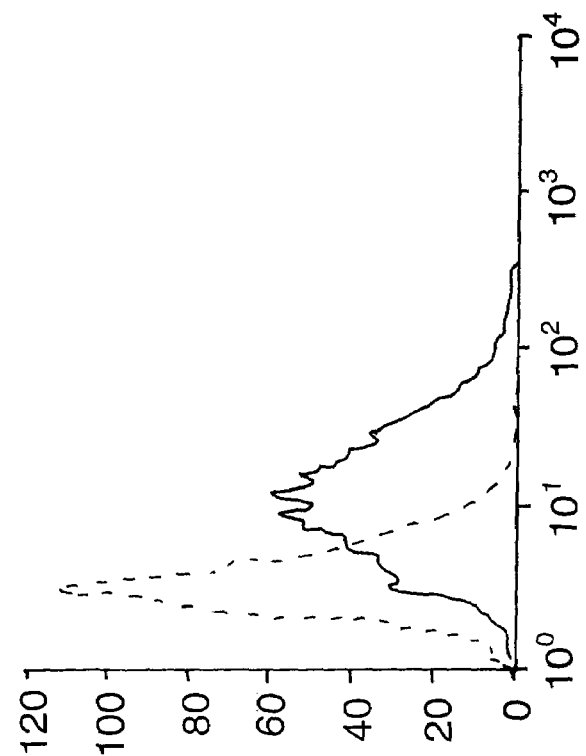
FIG. 15 shows the flow cytometric analysis of human ovarian cancer cells. Expression of CAR, $\alpha_v\beta_3$ and $\alpha_v\beta_5$ integrins in SKOV3.ip1 or OV-4 cells was analyzed by flow cytometry essentially as described in the legend for FIG. 11. CAR expression in SKOV3.ip1, FIG. 15A, and OV-4 cells, FIG. 15C.

Since a number of clinical trials utilizing adenoviral vectors to treat cancer patients via direct in vivo gene delivery are underway, whether the expanded tropism of Ad5lucRGD would render it useful for this type of clinical application was examined. First, the ability of this recombinant vector to deliver genes to cultured human ovarian cancer cells was examined. Characterization of two cell lines, SKOV3.ip1 and OV-4, by flow cytometry showed that they both express moderate-to-high levels of integrins $\alpha_v\beta_3$ and $\alpha_v\beta_3$ (FIGS. 15B and 15D), SKOV3.ip1 expresses a high level of CAR (FIG. 15A), whereas OV-4 is modest CAR expresser (FIG. 15C).

Figure 16A:
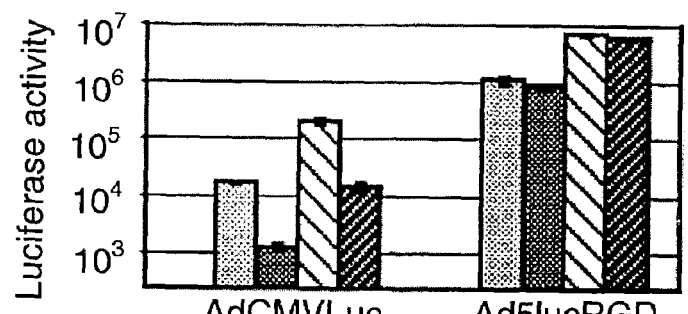
FIG. 16 shows a comparison of the gene transfer efficiencies to cultured ovarian cancer cells mediated by AdCMVLuc and Ad5lucRGD. Human ovarian cancer cells SKOV3.ip1 (16A) and OV-4 (16B) were transduced with AdCMVLuc or Ad5lucRGD at an moi of 1 or 10 pfu/cell essentially as described for 293, HUVEC and RD cells.

Gene transfer experiments utilizing SKOV3.ip1 and OV-4 showed that incorporation of recombinant RGD-containing fiber protein into Ad5lucRGD virion dramatically improved the ability of the virus to efficiently transduce these cells (FIG. 16A). At different MOI tested, Ad5lucRGD-transduced cultures of SKOV3.ip1 cells showed 30- to 60-fold increase in luciferase activity compared to cells transduced with control virus. Interestingly, while the fiber knob blocked over 90% of AdCMVLuc-mediated gene transfer, it could block only 15 to 20% of luciferase activity in Ad5lucRGD-treated cells.

Figure 16B:
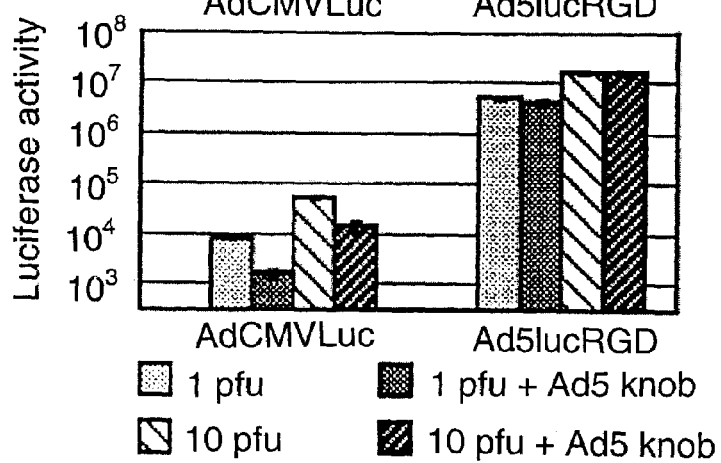

The difference in transduction efficiencies demonstrated by these two viral vectors was even greater, 300- to 600-fold, when OV-4 cells were employed (FIG. 16B). As before, the fiber knob used as an inhibitor of CAR-mediated cell entry didn't have any significant effect on Ad5lucRGD-mediated gene delivery, strongly suggesting that this virus primarily utilizes RGD-integrin interaction in order to bind to OV-4 cells.

Next, the utility of the Ad5lucRGD vector in the context of human ovarian cancer primary cells was evaluated. In this regard, recent human clinical trials have highlighted the disparity between the efficacy of adenoviral vectors in various model systems and in the clinical context, where rather low transduction efficiencies have been noted. These findings suggest the need to improve vector design as a general approach to augment the therapeutic index of the cancer gene therapy strategies. As integrins have been shown to be frequently overexpressed by various epithelial tumors, vector targeting to these cell surface receptors can provide a means to achieve CAR-independent gene transfer.

In experiments, ovarian cancer cells obtained from two patients were treated with both Ad5lucRGD and AdCMV-Luc in the presence or absence of blocking knob protein. The results obtained corroborated previous findings generated with cultured cells. Of note, luciferase readings in the lysates of cells treated with AdCMVLuc were extremely low (FIGS. 17A and 17B), thereby indicating inability of adenoviral vector containing unmodified fibers to efficiently infect ovarian cancer cells. Strong inhibition by the fiber knob on AdCMVLuc-mediated luciferase expression suggests that the fiber-CAR interaction is the only pathway this virus can use to infect this type of cell. In marked contrast, Ad5lucRGD directed levels of transgene expression two to three orders of magnitude higher than those detected in AdCMVLuc-transduced cells. The knob blocked 20% of the gene transfer at MOI of 1 pfu/cell, no effect was observed at MOI of 10 pfu/cell. Thus, the ability to achieve significant enhancement of gene delivery via CAR-independent pathway suggests the general utility of genetic retargeting of adenoviral vectors for efficient tumor transduction.

EXAMPLE 27

Vector-Mediated Gene Transfer to Human Ovarian Cancer Cell Lines Via the Genetically Modified Adenovirus The human ovarian cancer cell lines SKOV3.ip1, CaOV-3 and UCI-101 were infected with either the Ad5lucRGD or Ad5CMVLuc virus. In these gene transfer experiments, a dramatic augmentation of luciferase activity was noted with the modified RCD Ad vector (FIG. 18). At a dose of $3\times10^5$ and $3\times10^6$ PFU, Ad5lucRGD-infected cultures of SKOV3.ip1 cells demonstrated a 4.7- and 7.6-fold increase in luciferase activity, compared to cells infected with the control virus. With the CaOV-3 cells, increases of 244.2- and 471.6-fold was observed and with the UCI-101 cells, the increases were of 2.5- and 4.2-fold.

To determine the mechanistic basis of these augmented levels of gene transfer, blockade of adenoviral internalization via the native entry pathway was achieved by incubation with recombinant fiber knob protein. Competition of binding of the vector to cells with an excess of fiber knob protein blocked 82% and 91% of the AdCMVLuc-mediated luciferase activity in the SKOV3.ip1 cells. In contrast, however, this maneuver blocked only 27% and 39% of the Ad5lucRGD luciferase activity. These results together indicate that the Ad5lucRGD vector utilizes an alternative cell entry pathway for infection. The CaOV-3 cells were infected at a level too low to observe significant blocking with a dose of $3\times10^5$ PFU, although a 55% reduction of AdCMVLuc luciferase activity was observed with the fiber knob blockade at the dose of $3\times10^6$ PFU. In comparison, 0.1% and 42% blockade of the luciferase activity was observed after infection with a dose of $3\times10^5$ and $3\times10^6$ PFU of Ad5lucRGD, respectively. Also, the UCI-101 cultures demonstrated 94% and 97% reduction of AdCMVLuc luciferase activity by the fiber knob block, compared to a much smaller reduction of 28% and 39% of the Ad5lucRGD-encoded luciferase activity. Thus, CAR-independent gene transfer results in a dramatic augmentation of gene transfer into human ovarian cancer cells.

EXAMPLE 28

Vector-Mediated Gene Transfer to Human Ovarian Ascites Samples Via the Genetically Modified Adenovirus The present vector was tested in the more clinically relevant human ovarian ascites sample (Sterman et al., Human Gene Ther., 9:1083, 1998). Of note in this regard, integrins have been shown to be overexpressed by some epithelial tumors (Keely et al., Trends Cell Biol. 8:101, 1998; Sanders et al., Cancer Invest., 16:329, 1998; Liapis et al., Hum. Pathol. 28:443, 1997; Natali et al., Cancer Res., 57:1554, 1997; Pignatelli et al., Hum. Pathol. 23:1159, 1992), making the exploitation of these receptors via the RGD motif a viable alternative route to facilitate highly efficient, CAR-independent gene transfer.

Ovarian cancer ascites samples were infected with both AdCMVLuc and Ad5lucRGD vectors at doses of $3\times10^5$ and $3\times10^6$ PFU and a subset of samples received the blocking fiber knob. The results of these infections were similar to those found in the cultured cell line experiments (FIG. 19). The luciferase activity of the AdCMVLuc infected cells was extremely low in comparison to the Ad5lucRGD infected cells. The levels of augmentation of luciferase activity in the ascites sample #1 were of 64- and 50-fold, and the ascites sample #2 of 44 and 26.1%, respectively. The luciferase activity induced by AdCMVLuc was blocked by 90% infecting in the presence of an excess of fiber knob, again suggesting that the significant enhancement of gene delivery by Ad5lucRGD was obtained via CAR-independent cell entry pathways. In previous studies (Dmitriev et al., J. Virol. 72:9706, 1998), similar augmentation of gene transfer with Ad5lucRGD was demonstrated to ovarian cancer cells. Differences in the magnitude of augmentation noted in the present study, however, may reflect differences between primary tissues originated in different patients. In addition, previously frozen cells were used in the former studies, whereas fresh cells were used in the experiments described here. Results of both studies are compatible with a significant enhancement of adenoviral-mediated gene transfer via alternative cell entry pathways in clinically relevant tissue samples.

EXAMPLE 29

Adenoviral Vector Mediated Gene Transfer to Primary Ovarian Tumor Explants

The most stringent experimental substrate to establish the validity of a vector efficacy score for clinical use is fresh explants, given its consistently higher refractoriness to gene transfer. In this regard, three fresh primary ovarian tumor samples were infected with AdCMVLuc and Ad5lucRGD at a dose of $3\times10^5$ and $3\times10^6$ PFU with the blocking fiber knob. Again, the Ad5lucRGD vector produced increased luciferase activity compared to the AdCMVLuc vector (FIG. 20). Tumor #1 samples had enhanced luciferase activity of 11.1- and 5.7-fold at the doses of Ad indicated, respectively. Tumor #2 showed increments of 1.6- and 2.4-fold in luciferase activity, and tumor #3 had increments of 3.6- and 5.3-fold. The fiber knob blocked the majority of the AdCMVLuc infectious events, but blocked only slightly the Ad5lucRGD infection, confirming once more that CAR-independent gene transfer provided the basis of the observed augmentation in gene transfer efficacy. Thus, in this short-term culture system with a high level of stringency, significant increases in gene transfer were noted.

EXAMPLE 30

Adenoviral Vector Mediated Gene Transfer to Mesothelial Tissue Samples

The analysis of the efficiency of vectors for transducing tumor tissue compared to normal tissue should provide information about the infection differential that may be relevant to human clinical use. In this regard, toxicity and efficacy in the human context would be predicated upon the vector infectivity differential between tumor and nontumor tissues. Therefore, four mesothelial tissue samples obtained from patients operated on for benign gynecological conditions were infected with AdCMVLuc and Ad5lucRGD at doses of $3\times10^5$ and $3\times10^6$ PFU, with fiber knob to block infection. Interestingly, the mesothelial tissue samples expressed low luciferase activity with both the Ad5lucRGD vector (FIG. 21) and with AdCMVLuc. These data suggest that a favorable ratio in the tumor to normal tissue gene transfer will improve the therapeutic index of this novel adenoviral gene therapy vector.

EXAMPLE 31

Adenoviral Vector-Mediated Gene Transfer to Human SCCHN Cell Lines

Based on their high in vivo efficiency, adenoviral vectors have been employed in a variety of cancer gene therapy approaches (Huber & Lazo, Gene Therapy for Neoplastic Diseases, Ann. New York Acad. Sci. Vol 716). Nonetheless, dose-related toxicities and poor in situ transduction rates in human trials have suggested that adenoviral vectors, in their present form, may be suboptimal for this application (Roth & Cristiano, J. Natl. Canc. Inst. 89:21, 1997). To address this issue, we evaluated the efficiency of adenoviral vectors for human SCCHN lines as a gauge of their utility in this disease context. For these studies, a replication-defective adenoviral vector encoding the luciferase reporter gene, AdCMVLuc, was employed. The viral vector was delivered to cells in culture at a fixed multiplicity of infection (moi) of 10 particles/cell and 48 h later, cells were evaluated for luciferase gene expression. In addition, parallel experiments were carried out in the presence of recombinant fiber knob protein. This maneuver achieves blockade of the adenoviral vector's interaction with its target receptor, CAR, providing an index of the degree to which observed gene transfer is mediated through CAR pathways. As a control, the highly infectable human cell line, HeLa, was employed.

In these studies, the control HeLa cell line was highly susceptible to adenoviral vector-mediated gene delivery, as anticipated. Of note, however, the human SCCHN cell lines were significantly less susceptible to adenoviral vector-mediated infection than the control HeLa cells (FIG. 22). In this regard, the observed luciferase activity for FaDu was $4.8\times10^5$ and for SCC-25 was $6.9\times10^5$ RLU/mg protein. These reporter gene magnitudes were 4.0% and 5.7%, respectively, of the levels observed for HeLa. The SCCHN cell line SCC-4 exhibited a slightly higher degree of susceptibility, demonstrating luciferase levels that were 38% of those observed for HeLa. Studies carried out with knob competition exhibited more than 90% blockade in the instances of both the HeLa cells and the SCCHN cell lines. Thus, the observed levels of transduction were accomplished via CAR-dependent pathways. It appeared, based on these studies, that SCCHN cells were significantly less susceptible than HeLa to adenoviral vector-mediated gene transfer. Further, these studies suggested that the major cellular factor involved in adenoviral vector infection of human SCCHN lines was the primary adenoviral receptor, CAR.

The genetically modified adenovirus, Ad5lucRGD encoding the luciferase gene, was employed for transduction of the human SCCHN cell lines. Direct comparison was made in these studies to the non-modified, control virus AdCMVLuc. Application of the Ad5lucRGD to HeLa cells resulted in a 4-fold augmentation in gene transfer compared to the control virus AdCMVLuc (FIG. 23A). Addition of recombinant knob had no significant inhibitory effect on the gene transfer via Ad5lucRGD, confirming that the augmented levels of transgene expression represented transduction which had occurred via non-CAR pathways. Ad5lucRGD was next applied to the human SCCHN cell lines. In these studies, very dramatic augmentation in gene transfer were noted in these otherwise adenovirus-refractory cells. Specifically, the FaDu, SCC-4 and SCC-25 cells show a 35-, 18- and 77-fold enhancement in gene transfer, respectively. Significantly, knob competition had no effect on the gene transfer to these cells accomplished via the Ad5lucRGD vector. Thus, the achievement of CAR-independent gene transfer to SCCHN cells provides a means to overcome CAR deficiency in SCCHN and potentiated a highly augmented level of gene transfer.

EXAMPLE 32

In Situ Hybridization in Adenoviral-Infected SCCHN Cell Lines

In situ hybridization was employed to detect the mRNA transcript of the luciferase gene. To this end, luciferase mRNA was hybridized with a digoxigenin-labeled riboprobe and detected by enzyme cytochemical technique. As a control, uninfected cells of the SCCHN cell line SCC-25 showed no positive signal (FIG. 24A). Infection of these cells with AdCMVLuc at an moi of 250 pfu/cell induced limited positive staining. In contrast, cells infected with Ad5lucRGD at the same moi showed an enhanced signal, indicating an infection frequency of >80%. Relative luciferase activities achieved by these vectors, $4.1 \times 10^7$ and $3.3 \times 10^9$, respectively, were compatible with the results of the in situ hybridization. On the basis of these studies, it is thus apparent that the Ad5lucRGD infects a significantly greater fraction of the target tumor cells. Thus, the expedient of CAR-independent gene transfer allows a dramatic augmentation in both gene transfer levels, as well as transduction frequency in human SCCHN cells. This latter parameter is the key factor which predicts the ultimate utility of any cancer gene therapy approach.

EXAMPLE 33

Gene Transfer to Primary Explants of Human SCCHN

Whereas cell lines provide an index of the tissue specific parameters relevant to gene transfer, the analogy to human tumors is imprecise. In this regard, vector efficiencies in primary material are frequently distinct from those obtained with cell lines. In addition, gene transfer frequencies in human cell lines/murine xenografts models frequently overestimate infection rates ultimately obtainable in the context of human clinical gene therapy trials (Hesdorffer et al., J. Clin. Oncol. 16:165:1988; Bellon et al., Hum. Gene Ther. 8:15, 1997). On this basis, primary human material represents a key substrate for studies to establish the validity of developed vector approaches. In addition, the parallel analysis of targeted vectors in tumor and corresponding normal tissue provide insight as to the infection differential which may be accomplished in human clinical use. This differential may be the key factor which dictates the therapeutic index of a given gene therapy approach. Therefore, the tropism-modified adenoviral vectors were explored in the context of normal buccal mucosa, the normal tissue substrate relevant to SCCHN.

In these studies, primary tumor cells exhibited a relative resistance to the adenoviral vector AdCMVLuc, as compared to the human SCCHN cell lines (FIG. 25). These findings validate the frequently noted disparity in primary and cell line data and highlight the difficulty in achieving meaningful transduction rates to human tumors in situ. These findings were next compared with the Ad5lucRGD virus. Of note, the Ad5lucRGD accomplished augmented gene transfer to this otherwise refractory tumor target. Specifically, augmentations of 2.4- and 5.8-fold were noted in two independent isolates of primary tumor. Competition studies with knob confirmed that the observed augmentations occurred via the achievement of CAR-independent gene transfer. Thus, for fresh primary tumor material, which represents the clinically relevant study substrate for vector analysis, CAR-independent gene transfer allows significant augmentation of gene transfer to human SCCHN tumors. Of further note, no differential between AdCMVLuc and Ad5lucRGD could be noted in normal buccal mucosa (FIG. 25). This important finding predicts that this CAR-independent approach will allow an improved tumor to normal gene transfer differential, and thus, a potentially improved therapeutic study.

EXAMPLE 34

Systemic Targeting Potential of Ad5lucRGD

As the next logical step, the systemic targeting potential of Ad5lucRGD was evaluated, and present data indicate that the RGD motif in the HI loop can facilitate infection in the context of systemic vascular delivery, a key property not previously demonstrated for a targeted adenoviral vector.

To evaluate the systemic transduction properties of Ad5lucRGD, this virus was compared to a first generation adenovirus vector (AdCMVLuc) which has the same CMV-driven luciferase cassette in E1 as Ad5lucRGD, but does not have the RGD modification of the fiber protein. Plaque titering of these viruses was performed simultaneously by the same operator, as well as independently on two separate occasions, to ensure that an equivalent dose of the two vectors (on a plaque forming unit (pfu) basis), was being compared.

Either vector ($10^9$ pfu) was administered by lateral tail vein injection to C57black6 mice, five mice per group. Three days later, the mice were sacrificed and organs (heart, lung, liver, spleen, kidney) were harvested and analyzed for luciferase activity. For each analysis, the entire organ was snap frozen, ground using a mortar and pestle, then cells were lysed in lysis buffer and luciferase activity in the supernatant was measured using a commercial kit (Promega) and a Berthold luminometer. Data were normalized for protein content of the lysates.

Analysis of organ luciferase expression revealed a statistically significant enhancement with Ad5lucRGD compared to AdCMVLuc in the liver, lung, spleen and kidney, the most striking finding being in the latter instance, where there was greater then 50-fold enhancement of expression (FIG. 26). Notably, this high level of enhancement in vivo is comparable to in vitro findings with this vector. In contrast, no enhancement was seen in the heart. For both vectors, the highest level of transgene expression was seen in the liver. Uptake of virus in the liver may relate to circulatory factors in combination with both non-specific and CAR-specific mechanisms (Zinn et al., Gene Ther. 5:798, 1998). In this regard, there is evidence that the levels of mCAR (the murine homologue of human CAR) are found in the mouse liver (Tomko et al., PNAS, 94:3352, 1997). Because Adlu-cRGD retains native tropism in addition to its integrin binding properties, it is perhaps not surprising that hepatic uptake with this vector predominated. In fact, a moderate enhancement of luciferase expression with Ad5lucRGD occurred at this site. Importantly however, assessment of the ratio of luciferase expression in the other organs to the expression in the liver for each individual mouse revealed the differential transduction profile of Ad5lucRGD (FIG. 27). This differential profile indicates that these findings are due to the different biology of the two vectors, and are not attributable to minor variations in the titer of the vector preparations. Thus, these data provide the first evidence that genetic modification of the adenoviral fiber can lead to selective enhancement of transgene expression in the highly stringent context of systemic vascular administration.

Several investigators have found that cellular localization of reporter gene expression following systemic administration of adenovirus is difficult in organs other than the liver due to the predominant sequestration of the vector in this organ (Worgall et al., Hum. Gene Ther. 8:37, 1997). For this reason, in the experiments reported herein, a luciferase reporter gene, followed by light unit detection, was chosen. The high sensitivity of this technique enabled reproducible evaluation of the transgene expression profile of the modified vector at the organ level. In an effort to illustrate transgene expression at the cellular level of resolution, in situ hybridization was performed for luciferase mRNA in the various organs. With both vectors, luciferase mRNA could be detected in hepatocytes (up to 15% of cells using a viral dose of $10^9$ pfu) with no obvious qualitative distinction between the two vectors. As with other cellular detection systems (e.g. the use of a β-galactosidase reporter), however, the limits of sensitivity offered by the hybridization approach meant that the signal for luciferase mRNA was undetectable in organs other than the liver. It is believed that further modifications of the vector to reduce hepatic sequestration will be required to allow adequate cellular resolution of non-hepatic transgene expression using currently available techniques. Importantly, the encouraging demonstration that genetic alterations of adenoviral fiber can greatly improve transgene expression at certain non-hepatic sites after systemic administration provides a stimulus to engineer additional refinements to abolish native tropism.

The data presented herein addresses a key issue in the development of targeted adenoviral vectors. Previously, there have been no reports of the properties of targeted vectors administered systemically. In this study, it is shown that the addition of an RCD motif into the HI loop alters the transgene expression profile of the systemically administered vector, indicating that this region of the vector is potentially an ideal location for the insertion of targeting motifs, and that the attributes of the vector are not undermined by either serum factors or limited motif accessibility. Therefore, this approach, if successfully combined with ablation of native tropism by further modifications, may allow the production of a truly cell-specific vector administerable by the systemic route.

SUMMARY

The present invention describes the generation and characterization of recombinant adenoviral vector containing fibers with an RGD-4C sequence genetically incorporated within the HI loop of the carboxy terminal knob domain. An effort to create such a virus was undertaken in order to demonstrate the utility of the HI loop of the fiber knob as an optimal site for incorporation of short peptide ligands, which would allow the virus to bind to ligand-specific cellular receptors, thereby resulting in altered or expanded tropism of the vector.

The interaction between cellular integrins and various proteins containing an RGD tripeptide is one of the best characterized interactions between macromolecules. This interaction plays an important role in a variety of fundamental biological processes, including cell adhesion and viral infection. In this regard, it has been shown that the RGD motif contained in adhesive proteins such as fibrinectin, vitronectin, collagen, osteopontin, thrombospondin, fibrinogen, laminin and von Willebrand factor allows efficient and specific interaction between these proteins and integrin molecules. It is also known that an RGD motif is present in some viral proteins including the VP1 proteins of the coxsackievirus and the foot-and-mouth disease virus, the penton base protein of the majority of known adenoviruses, the VP7 proteins of the African horse sickness virus and bluetongue virus, the Tat protein of the human immunodeficiency virus, and the glycoprotein H of the herpes simplex virus. In some of these instances this tripeptide has been shown to play an important role in the process of viral infection by mediating primary or secondary interaction between the virion and cell surface localized integrins. Furthermore, genetic incorporation of the RGD-containing sequences into chimeric hepatitis B cores, poliovirus particles, bacteriophage fd and human adenovirus virions allows specific interaction of these viral particles with cellular integrins, thereby resulting in binding of aforementioned structures to cell surface.

The present invention describes a genetic strategy to expand the tropism of recombinant adenovirus vector with respect to cell types which normally are refractory to adenovirus infection. Based on findings disclosed herein the on accessibility of the HI loop localized FLAG peptide, positioning of the RGD-4C peptide in close proximity to the putative cell binding domain localized within the knob of Ad5 fiber protein should make this ligand available for efficient interaction with integrins on the cell membrane. By using an ELISA-based binding assay, direct interaction between the RGD motif of the fiber-RGD protein with purified integrin $\alpha_v\beta_3$ was shown. This key finding provided a rationale for the generation of recombinant adenovirus vector, Ad5lucRGD, containing such fiber-RGD proteins. The data generated with Ad5lucRGD on several cell lines showed that this virus demonstrates profiles of gene transfer significantly different from those by the virus with unmodified fibers. This difference was especially dramatic when CAR-negative cells were utilized for the gene delivery experiments. Investigation of radiolabeled virus binding to the cells in vitro paralleled the gene transfer experiments, thereby supporting the concept of augmented efficiency of transgene expression as a result of more efficient primary interaction between the virus and the target cell.

In order to demonstrate the utility of the newly generated viral vector for clinical applications in the context of gene therapy, Ad5lucRGD was employed for gene delivery to cells isolated from ascites obtained from ovarian cancer patients. In this model, Ad5lucRGD was able to direct levels of transgene expression two to three orders of magnitude higher that those mediated by control virion containing unmodified fibers. These results strongly suggest that recombinant adenoviral vectors containing fibers with genetically incorporated RGD peptides may be of great utility in the context of cancer gene therapy approaches based on in vivo gene delivery. In addition, well-documented overexpression of several types of integrins in tumor vasculature suggests that derivatives of Ad5lucRGD expressing therapeutic genes may be utilized for eradication of tumors via abrogation of their blood supply.

Successful utilization of the RGD tripeptide incorporated into HI loop of adenovirus fiber protein for the purposes of vector retargeting, suggests that other peptide ligands may work just a s well in a context of the fiber molecule. In this regard, the rapidly emerging technology of phage display libraries has proved its utility as a means to identify peptides, which demonstrate the ability to specifically bind to certain molecules on a cell surface in vivo. This high throughput method is based on a capability of small peptide ligands to target a bacteriophage particle to previously characterized as well as to unknown structures on a cell membrane. Recent successes in phage biopanning in an in vivo context strongly suggest that this technology may provide a source of targeting peptides to be used for modification of endogenous tropism of recombinant adenoviral vectors.

Although the utility of small peptides to be incorporated into the HI loop of the fiber knob was demonstrated, the size restrictions of this locale have not been fully defined. In this regard, the compatibility of the HI loop structure with protein ligands of a larger size, such as, for example, single chain antibodies (scFv), would significantly expand the range of potential targeting approaches. Furthermore, incorporation of large polypeptide ligands into the HI loop, which connects β-strands H and I involved in the formation of the cell binding site, may create a steric hindrance, thereby preventing direct interaction of the fiber knob with CAR and resulting in elimination of endogenous tropism of the virus. This, in turn, would result in a new generation of truly retargeted adenoviral vectors, capable of cell-specific gene delivery exclusively via CAR-independent mechanisms.

The following references were cited herein:
1. Bai, et al., 1994. J. Virol. 68:5925-5932.
2. Bai, et al., 1993. J. Virol. 67:5198-5205.
3. Belin, et al., 1993. J. Gen. Virol. 74:1485-1497.
4. Bergelson, et al., 1997. Science 275:1320-1323.
5. Bout, et al., 1994. Gene Ther. 1:385-394.
6. Bout, et al., 1994. Hum. Gene Ther. 5:3-10.
7. Chartier, et al., 1996. J. Virol. 70:4805-4810.
8. Crompton, et al., 1994. J. Gen. Virol. 75:133-139.
9. Crystal, et al., 1994. Nat. Genet. 8:42-51.
10. Csete, et al., 1995. Transplantation 59:263-268.
11. Curiel, et al., 1992. Hum. Gene Ther. 3:147-154.
12. DeMatteo, et al., 1995. Ann. Surg. 222:229-239.
13. Di Guilmi, et al., 1995. Virus Res. 38:71-81.
14. Douglas, et al., 1996. Nat. Biotechnol. 14:1574-1578.
15. Graham, et al., 1977. J. Gen. Virol. 36:59-74.
16. Henry, et al., 1994. J. Virol. 68:5239-5246.
17. Herz, J., & R. D. Gerard. 1993. Proc. Natl. Acad. Sci. USA 90:2812-2816.
18. Hong, J. S. & J. A. Engler. 1991. Virology 185:758-767.
19. Hong, et al., 1997. EMBO J. 16:2294-2306.
20. Huang, et al., 1996. J. Virol. 70:4502-4508.
21. Jaffe, et al., 1992. Nat. Genet. 1:372-378.
22. Jolly, D. 1994. Cancer Gene Ther. 1:51-64.
23. Koivunen, et al., 1994. Peptides in cell adhesion research, in Methods in Enzymology 245:346-369.
24. Koivunen, et al., 1994. J. Cell Biol. 124:373-380.
25. Krasnykh, et al., 1996. J. Virol. 70:6839-6846.
26. Le Gal La Salle, et al., 1993. Science 259:988-990.
27. Louis, et al., 1994. J. Virol. 68:4104-4106.
28. Maeda, et al., 1994. Gastroenterology 106:1638-1644.
29. Maizel, et al., 1968. Virology 36:115-125.
30. Mastrangeli, et al., 1994. Am. J. Physiol. 266:G1146-G1155.
31. Michael, et al., 1995. Gene Ther. 2:660-668.
32. Mitani, 1994. Hum. Gene Ther. 5:941-948.
33. Mittereder, et al., 1996. J. Virol. 70:7498-7509.
34. Novelli, A., & P. A. Boulanger. 1991. Virology 185:365-376.
35. Roelvink, et al., 1996. J. Virol. 70:7614-7621.
36. Siegfried, W. 1993. Exp. Clin. Endocrinol. 101:7-11.
37. Stevenson, et al., 1997. J. Virol. 71:4782-4790.
38. Stevenson, et al., 1995. J. Virol. 69:2850-2857.
39. Tomko, R. P et al. 1997. Proc. Natl. Acad. Sci. USA 94:3352-3356.
40. Trapnell, B., & M. Gorziglia. 1994. Curr. Opin. Biotechnol. 5:617-625.
41. Varga, et al., 1991. J. Virol. 65:6061-6070.
42. Wickham, et al., 1995. Gene Ther. 2:750-756.
43. Wickham, et al., 1994. J. Cell Biol. 127:257-264.
44. Wickham, et al., 1993. Cell 73:309-319.
45. Wickham, et al., 1996. Nat. Biotechnol. 14:1570-1573.
46. Wickham, et al., 1996. J. Virol. 70:6831-6838.
47. Xia, et al., 1995. Top. Microbiol. Immunol. 199:39-46.
48. Xia, et al., 1994. Structure 2:1259-1270.

Any patents or publications mentioned in this specification are indicative of the levels of those skilled in the art to which the invention pertains. These patents and publications are incorporated by reference to the same extent as if each individual publication was individually indicated as incorporated by reference.

One skilled in the art will readily appreciate that the present invention is well adapted to carry out the objects and obtain the ends and advantages mentioned, as well as those inherent therein. The present examples along with the methods, procedures, treatments and molecules described herein are representative of preferred embodiments, are exemplary, and are not limitations on the scope of the invention. Changes therein and other uses will occur to those skilled in the art which are encompassed within the spirit of the invention as defined by the scope of the claims.

What is claimed is:

1. A recombinant Ad5 adenovirus comprising an Ad5 fiber gene modified in the HI loop domain of an Ad5 fiber knob by introduction of a ligand comprising an Arg-Gly-Asp (RGD) peptide into said HI loop domain, wherein the Ad5 fiber gene encoding the Ad5 fiber with the RGD peptide within the HI loop of the knob comprises an annealed duplex of (SEQ ID No. 10) and (SEQ ID No. 11).

2. The recombinant adenovirus of claim 1, wherein said adenovirus can achieve CAR-independent transfer.

3. The recombinant adenovirus of claim 1, wherein said adenovirus further comprises an additional modification to said fiber knob, thereby ablating the native tropism of said adenovirus.

4. The recombinant adenovirus of claim 1, wherein said modified fiber knob retains its ability to trimerize and retains its native biosynthesis profile.

5. The recombinant adenovirus of claim 1, wherein the adenovirus vector encoding said adenovirus further comprises a therapeutic gene.

6. A method of increasing the ability of an adenovirus to transduce a cell, wherein the cell has native adenoviral receptors, comprising the step of: modifying the fiber gene in the HI loop domain of the fiber knob of said adenovirus by introducing a ligand into said HI loop domain thereby generating the adenovirus of claim 1.

7. The recombinant adenovirus of claim 5, wherein said therapeutic gene is the herpes simplex virus-thymidine kinase gene.

8. The method of claim 6, wherein said cell is a tumor cell.

9. The method of claim 6, wherein the adenoviral vector encoding said adenovirus further comprises a therapeutic gene.

10. The method of claim 8, wherein said tumor cell is selected from the group consisting of in vitro, in vivo and ex vivo.

* * * * *